United States Patent
Poulsen et al.

(10) Patent No.: US 10,323,085 B2
(45) Date of Patent: Jun. 18, 2019

(54) METHODS OF TREATING FIBROMYALGIA

(71) Applicant: Teva Pharmaceuticals International GmbH, Jona (CH)

(72) Inventors: Kristian Todd Poulsen, San Francisco, CA (US); David Louis Shelton, Oakland, CA (US); Joerg Zeller, North Wales, PA (US); Ian Machin, Sandwich (GB); Laura Corradini, Sandwich (GB)

(73) Assignee: Teva Pharmaceuticals International GmbH, Jona (CH)

( * ) Notice: Subject to any disclaimer, the term of this patent is extended or adjusted under 35 U.S.C. 154(b) by 0 days.

(21) Appl. No.: 15/968,947

(22) Filed: May 2, 2018

(65) Prior Publication Data
US 2019/0106483 A1    Apr. 11, 2019

Related U.S. Application Data

(60) Continuation of application No. 15/341,610, filed on Nov. 2, 2016, now abandoned, which is a continuation of application No. 15/081,681, filed on Mar. 25, 2016, now abandoned, which is a continuation of application No. 14/612,110, filed on Feb. 2, 2015, now Pat. No. 9,328,167, which is a continuation of application No. 13/892,121, filed on May 10, 2013, now abandoned, which is a continuation of application No. 13/623,206, filed on Sep. 20, 2012, now abandoned, which is a division of application No. 12/920,621, filed as application No. PCT/IB2009/050852 on Mar. 3, 2009, now Pat. No. 8,293,239.

(60) Provisional application No. 61/033,558, filed on Mar. 4, 2008.

(51) Int. Cl.
| | | |
|---|---|---|
| *A61K 39/395* | (2006.01) | |
| *C07K 16/18* | (2006.01) | |
| *C07K 16/22* | (2006.01) | |
| *A61K 45/06* | (2006.01) | |
| *C07K 16/26* | (2006.01) | |
| *A61K 39/00* | (2006.01) | |

(52) U.S. Cl.
CPC .......... *C07K 16/18* (2013.01); *A61K 39/3955* (2013.01); *A61K 45/06* (2013.01); *C07K 16/26* (2013.01); *A61K 2039/505* (2013.01); *C07K 2317/21* (2013.01); *C07K 2317/24* (2013.01); *C07K 2317/34* (2013.01); *C07K 2317/51* (2013.01); *C07K 2317/56* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,816,567 | A | 3/1989 | Cabilly et al. |
| 5,116,964 | A | 5/1992 | Capon et al. |
| 5,500,362 | A | 3/1996 | Robinson et al. |
| 5,545,806 | A | 8/1996 | Longberg et al. |
| 5,545,807 | A | 8/1996 | Surani et al. |
| 5,569,825 | A | 10/1996 | Longberg et al. |
| 5,625,126 | A | 4/1997 | Longberg et al. |
| 5,633,425 | A | 5/1997 | Longberg et al. |
| 5,661,016 | A | 8/1997 | Longberg et al. |
| 5,750,373 | A | 5/1998 | Garrard et al. |
| 5,821,337 | A | 10/1998 | Carter et al. |
| 5,851,556 | A | 12/1998 | Breton et al. |
| 5,932,215 | A | 8/1999 | De Lacharriere et al. |
| 5,935,586 | A | 8/1999 | De Lacharriere et al. |
| 5,938,586 | A | 8/1999 | De Lacharriere et al. |
| 5,981,568 | A | 11/1999 | Kunz et al. |
| 6,063,768 | A | 5/2000 | First |
| 6,168,809 | B1 | 1/2001 | De Lacharriere et al. |
| 6,180,370 | B1 | 1/2001 | Queen et al. |
| 6,313,097 | B1 | 11/2001 | Eberlein et al. |
| 6,344,438 | B1 | 2/2002 | De Lacharriere et al. |
| 6,344,449 | B1 | 2/2002 | Rudolf et al. |
| 6,509,014 | B1 | 1/2003 | De Lacharriere et al. |
| 6,521,609 | B1 | 2/2003 | Doods et al. |
| 6,552,043 | B1 | 4/2003 | Patchett et al. |
| 6,586,458 | B1 | 7/2003 | Plachetka |
| 6,737,056 | B1 | 5/2004 | Presta |
| 6,767,056 | B2 | 5/2004 | Presta |
| 7,109,214 | B2 | 9/2006 | Zimmer et al. |
| 7,384,930 | B2 | 6/2008 | Chaturvedula et al. |
| 7,479,488 | B2 | 1/2009 | Mueller et al. |
| 7,772,224 | B2 | 8/2010 | Paone et al. |

(Continued)

FOREIGN PATENT DOCUMENTS

| | | |
|---|---|---|
| CA | 2563687 | 11/2005 |
| CN | 1308676 | 5/2001 |

(Continued)

OTHER PUBLICATIONS

U.S. Appl. No. 13/621,981, filed Sep. 18, 2012, Poulsen et al.
U.S. Appl. No. 13/623,206, filed Sep. 20, 2012, Poulsen et al.
U.S. Appl. No. 13/835,394, filed Mar. 25, 2013, Zeller et al.
U.S. Appl. No. 14/612,117, filed Feb. 2, 2015, Zeller et al.
U.S. Appl. No. 15/909,787, filed Mar. 1, 2018, Burstein.
U.S. Appl. No. 15/909,895, filed Mar. 1, 2018, Burnstein.
U.S. Appl. No. 60/753,044, filed Dec. 22, 2005, Benschop et al.
"Emerging Concepts in GPCR Research and Their Implications for Drug Discovery," Wiley Handbook of Current and Emerging Drug Therapies vol. 1-4: 369-386, 2007, 18 pages.

(Continued)

*Primary Examiner* — Christine J Saoud
*Assistant Examiner* — Jon M Lockard
(74) *Attorney, Agent, or Firm* — Fish & Richardson P.C.

(57) ABSTRACT

The invention relates to an anti-CGRP antibody for use in the prevention and/or treatment of chronic pain and/or symptoms of chronic pain, and to a method of treating and/or preventing chronic pain and/or symptoms of chronic pain using an anti-CGRP antibody.

18 Claims, 10 Drawing Sheets

Specification includes a Sequence Listing.

(56) References Cited

U.S. PATENT DOCUMENTS

| | | |
|---|---|---|
| 8,007,794 B2 | 8/2011 | Zeller et al. |
| 8,168,592 B2 | 5/2012 | Gegg, Jr. et al. |
| 8,293,239 B2 | 10/2012 | Poulsen et al. |
| 8,298,536 B2 | 10/2012 | Poulsen et al. |
| 8,586,045 B2 | 11/2013 | Zeller et al. |
| 8,597,649 B2 | 12/2013 | Zeller et al. |
| 8,734,802 B1 | 5/2014 | Zeller et al. |
| 9,102,731 B2 | 8/2015 | Boone et al. |
| 9,115,194 B2 | 8/2015 | Zeller et al. |
| 9,266,951 B2 | 2/2016 | Zeller et al. |
| 9,328,167 B2 | 5/2016 | Poulsen et al. |
| 9,328,168 B2 | 5/2016 | Zeller et al. |
| 9,340,614 B2 | 5/2016 | Zeller et al. |
| 9,346,881 B2 | 5/2016 | Zeller et al. |
| 9,365,648 B1 | 6/2016 | Zeller et al. |
| 9,884,907 B2 | 2/2018 | Zeller et al. |
| 9,884,908 B2 | 2/2018 | Zeller et al. |
| 9,890,210 B2 | 2/2018 | Zeller et al. |
| 9,890,211 B2 | 2/2018 | Zeller et al. |
| 2001/0036946 A1 | 11/2001 | Rudulf et al. |
| 2002/0162125 A1 | 10/2002 | Salmon et al. |
| 2002/0164707 A1 | 11/2002 | Adamou et al. |
| 2003/0069231 A1 | 4/2003 | Rudolf et al. |
| 2003/0194404 A1 | 10/2003 | Greenfeder et al. |
| 2003/0236282 A1 | 12/2003 | Hurnaurs et al. |
| 2004/0132716 A1 | 7/2004 | Rudolph et al. |
| 2005/0183700 A1 | 8/2005 | Dolker |
| 2005/0227968 A1 | 10/2005 | Lustenberger et al. |
| 2005/0234054 A1 | 10/2005 | Mueller et al. |
| 2005/0272955 A1 | 12/2005 | Zimmer et al. |
| 2006/0183700 A1 | 8/2006 | Vater et al. |
| 2007/0244099 A1 | 10/2007 | Rudolph et al. |
| 2008/0004261 A1 | 1/2008 | Gutirrez et al. |
| 2009/0220489 A1 | 9/2009 | Zeller et al. |
| 2010/0172895 A1 | 7/2010 | Boone et al. |
| 2011/0054150 A1 | 3/2011 | Poulsen et al. |
| 2011/0257371 A1 | 10/2011 | Poulsen et al. |
| 2012/0009192 A1 | 1/2012 | Zeller et al. |
| 2013/0216535 A1 | 8/2013 | Zeller et al. |
| 2013/0295087 A1 | 11/2013 | Poulsen et al. |
| 2013/0295088 A1 | 11/2013 | Poulsen et al. |
| 2014/0147438 A1 | 5/2014 | Zeller et al. |
| 2015/0050267 A1 | 2/2015 | Zeller et al. |
| 2015/0291690 A1 | 10/2015 | Zeller et al. |
| 2015/0307607 A1 | 11/2015 | Bigal et al. |
| 2015/0361171 A1 | 12/2015 | Zeller et al. |
| 2015/0361172 A1 | 12/2015 | Zeller et al. |
| 2015/0361173 A1 | 12/2015 | Zeller et al. |
| 2015/0376286 A1 | 12/2015 | Boone et al. |
| 2016/0168244 A1 | 2/2016 | Zeller et al. |

FOREIGN PATENT DOCUMENTS

| | | |
|---|---|---|
| CN | 1671711 | 9/2005 |
| EP | 0212432 | 3/1987 |
| EP | 1031350 | 8/2000 |
| EP | 1556020 | 7/2005 |
| EP | 1770091 | 4/2007 |
| JP | H07196700 A | 8/1995 |
| JP | H08268874 A | 10/1996 |
| JP | 2007523870 | 8/2007 |
| JP | 2009515942 | 4/2009 |
| RU | 2329062 | 7/2008 |
| WO | WO 1991/000737 | 1/1991 |
| WO | WO 1994/021665 A1 | 9/1994 |
| WO | WO 1995/05468 A1 | 2/1995 |
| WO | WO 1996/004928 A1 | 2/1996 |
| WO | WO 1996/33735 A1 | 10/1996 |
| WO | WO 1997/009046 A1 | 3/1997 |
| WO | WO 1997/041223 A1 | 11/1997 |
| WO | WO 1998/003534 A1 | 1/1998 |
| WO | WO 1998/008630 | 3/1998 |
| WO | WO 1998/009630 A1 | 3/1998 |
| WO | WO 1998/011128 A1 | 3/1998 |
| WO | WO 1998/056779 A1 | 12/1998 |
| WO | WO 1999/058572 A1 | 11/1999 |
| WO | WO 2000/018764 A1 | 4/2000 |
| WO | WO 2001/027160 | 4/2001 |
| WO | WO 2003/027252 | 4/2003 |
| WO | WO 2003/093472 A2 | 11/2003 |
| WO | WO 2003/104236 A1 | 12/2003 |
| WO | WO 2004/003019 A2 | 1/2004 |
| WO | WO 2004/014351 A2 | 2/2004 |
| WO | WO 2004/050683 A2 | 6/2004 |
| WO | WO 2004/082602 A2 | 9/2004 |
| WO | WO 2004/082605 A2 | 9/2004 |
| WO | WO 2004/082678 A1 | 9/2004 |
| WO | WO 2004/083187 A1 | 9/2004 |
| WO | WO 2004/087649 A2 | 10/2004 |
| WO | WO 2004/091514 A2 | 10/2004 |
| WO | WO 2004/092166 A2 | 10/2004 |
| WO | WO 2004/092168 A1 | 10/2004 |
| WO | WO 2004/097421 | 11/2004 |
| WO | WO 2005/009962 A1 | 2/2005 |
| WO | WO 2005/041757 | 5/2005 |
| WO | WO 2005/100360 A1 | 10/2005 |
| WO | WO 2006/077212 A1 | 7/2006 |
| WO | WO 2007/025212 A2 | 3/2007 |
| WO | WO 2007/025286 A2 | 3/2007 |
| WO | WO 2007/035906 A2 | 3/2007 |
| WO | WO 2007/048026 A2 | 4/2007 |
| WO | WO 2007/054809 A2 | 5/2007 |
| WO | WO 2007/061676 A2 | 5/2007 |
| WO | WO 2007/076336 A1 | 7/2007 |
| WO | WO 2008/011190 A1 | 1/2008 |
| WO | WO 2008/097824 | 8/2008 |
| WO | WO 2009/055350 | 4/2009 |
| WO | WO 2009/109908 A1 | 9/2009 |
| WO | WO 2009/109911 A1 | 9/2009 |

OTHER PUBLICATIONS

"Guidance for Industry—Estimating the Maximum Safe Starting Dose in Initial Clinical Trials for Therapeutics in Adult Healthy Volunteers," U.S. Department of Health and Human Services, Food and Drug Administration, Center for Drug Evaluation and Research (CDER), Jul. 2005, 30 pages.
"Guidelines for the Management of Rheumatoid Arthritis," Arthritis and Rheumatism vol. 46, No. 2:328-346, Feb. 2002, 19 pages.
"Physician's Desk Reference," PDR, 58 Edition, 2004, 39 pages.
"Physician's Desk Reference," PDR, 59 Edition, 2005, 28 pages.
Abbott, "Astrocyte-endothelial interactions and blood-brain barrier permeability", Journal of Anatomy 200(6):629-638, Jun. 2002, 10 pages.
Abbott, "Chapter 15: Comparative Physiology of the Blood-Brain Barrier", Physiology and Pharmacology of the Blood-Brain Barrier, pp. 371-396, 1992, 26 pages.
Abbott, "Evidence for bulk flow of brain interstitial fluid: significance for physiology and pathology", Neurochemistry International 45(4):545-552, Sep. 2004, 8 pages.
Abstracts of the XII Congress of the International Headache Society, IHC 2005, Oct. 9-12, 2005, Cephalalgia 25:923, Oct. 9-12, 2005, 3 pages.
Adam et al., "Severity of mucosal inflammation as a predictor for alterations of visceral sensory function in a rat model," Pain 123(1-2):179-86, Jul. 2006, 8 pages.
Adams et al., "Monoclonal antibody therapy of cancer", Nature Biotechnology 23(9):1147-1157, Sep. 2005, 11 pages.
Adelman et al., "Comparison of rizatriptan and other triptans on stringent measures of efficacy," Neurology vol. 57, 1377-83, Oct. 2001, 8 pages.
Adwanikar et al., "Spinal CGRP1 receptors contribute to supraspinally organized pain behavior and pain-related sensitization of amygdala neurons," Pain 132(1-2):53-66, Nov. 2007, 14 pages.
Afridi et al., "Glyceryl trinitmte triggers premonitory symptoms in migraineurs", Pain 110:675-680, Aug. 2004, 6 pages.
Afridi et al., "Verapamil and lymphomatoid papulosis in chronic cluster headache", Journal of Neurology 251:473-475, Apr. 2004, 3 pages.
Aggarwal, "Signalling pathways of the TNF superfamily: a double-edged sword," Natural Review of Immunol., vol. 3, 745-756, Sep. 2003, 12 pages.

(56) References Cited

OTHER PUBLICATIONS

Ahmed et al., "Capsaicin effects on substance P and CGRP in rat adjuvant arthritis," Regulatory Peptide, 1995, 55: 85-102.

Alm and Basbaum, "Where do triptans act in the treatment of migraine?" Pain 115: 1-4, May 2005, 4 pages.

Aiyar et al., "A cDNA encoding the calcitonin gene-related peptide type 1 receptor," the Journal of Biological Chemisty, vol. 271, No. 19, May 1996, 6 pages.

Aiyar et al., "Pharmacology of SB-273779, a nonpeptide calcitonin gene-related peptide 1 receptor antagonist," J Pharmacolog Exp Therap 296(3):768-775, 2001, 8 pages.

Akerman and Goadsby, "Topiramate inhibits cortical spreading depression in rat and cat: impact in migraine aura", Neuroreport 16:1383-1387, Aug. 2005, 5 pages.

Akerman et al., "Oxygen inhibits neuronal activation in the trigeminocervical complex after stimulation of trigeminal autonomic reflex but not during direct dural activation of trigeminal afferents," Headache 49; 1131-1143, Sep. 2009, 13 pages.

Akerman et al., "The effect of adrenergic compounds on neurogenic dural vasodilation", European Journal of Pharmacology 424(1):53-58, Aug. 2001, 6 pages.

Akerman et al., "The effect of adrenergic compounds on neurogenic vasodilation of dural meningeal vessels," Cephalalgia 20: 281-283, Jul. 2000, 2 pages.

Akerman et al., "The effect of anti-migraine compounds on nitric oxide induced dilation of dural meningeal vessels", European Journal of Pharmacology 452:223-228, Oct. 2002, 6 pages.

Akerman et al., "Topiramate inhibits trigeminovascular activation: an intravital microscopy study", British Journal of Pharmacology 146:7-14, Sep. 2005, 8 pages.

Alberts et al., "Molecular Biology of the Cell," p. G-34, 4th Edition, Garland Science, Taylor & Francis Group, New York, 2002, 5 pages.

Alexander et al., "Calcitonin, amylin, CGRP and adrenomedullin," British Journal of Pharmacology, 158(Suppl. 1), Nov. 2009, 2 pages.

Al-Lazikani et al., "Standard conformations for the canonical structures of immunoglobulins," J Mol Biol 273(4):927-948, Nov. 7, 1997, 22 pages.

Allt et al., "Is the pial microvessel a good model for blood-brain barrier studies?" Brain Research Reviews, vol. 24:67-76, Jun. 1997, 10 pages.

Almagro and Strohl, "Antibody engineering. humanization, affinity maturation, and selection technique," Therapeutic Monoclonal Antibodies Chapter 13, pp. 311-334, 2009, 24 pages.

Amara et al., "Expression in brain of a messenger RNA encoding a novel neuropeptide homologous to calcitonin gene-related peptide," Science 229(4718):1094-1097, Sep. 13, 1985, 4 pages.

Ambalavanar et al., "Deep tissue inflammation upregulates neuropeptides and evokes nociceptive behaviors which are modulated by a neuropeptide antagonist," Pain 120(1-2):53-68, Jan. 2006, 16 pages.

American College of Rheumatology Subcommittee on Rheumatoid Arthritis Guidelines, "Guidelines for the management of rheumatoid arthritis: 2002 update," Arthritis & Rheumatism, 2002, 46(2): 328-346.

An, "Therapeutic Monoclonal Antibodies From Bench to Clinic," Wiley Chapter 31, pp. 711-762, 2009, 55 pages.

Andrew et al., "Monoclonal antibodies distinguishing alpha and beta forms of calcitonin gene-related peptide," J Immunol Methods 134(1):87-94, Nov. 6, 1990, 8 pages.

Annequin et al., "Last-Minute Poster Presentations", Cephalalgia 25:1189-1205, Dec. 2005, 7 pages.

Antonaci et al., "Recent advances in migraine therapy," Springer Plus 2016, No. 5, 637, May 2016, 14 pages.

Arfors et al., "Microvascular transport of macromolecules in normal and inflammatory conditions", Acta Physiol Scand Suppl., 463:93-103, 1979, 11 pages.

Armour et al., "Pharmacological characterization of receptor-activity-modifying proteins (RAMPs) and the human calcitonin receptor", J Pharmacol Toxicol 42: 217-224, Dec. 1999, 8 pages.

Armour et al., "Recombinant human IgG molecules lacking Fcγ receptor I binding and monocyte triggering activities," Eur J lmmunol 29(8):2613-2624, Aug. 1999, 12 pages.

Arndt et al., "CGRP Antagonism—A Valid New Concept for the Treatment of Migraine Pain," Neuropeptides vol. 38, No. 2-3, Apr./Jun. 2004, 6 pages.

Arulmani et al., "Calcitonin gene-related peptide and its role in migraine pathophysiology," Eur J Pharmacol 500(1-3):315-330, Oct. 1, 2004, 16 pages.

Arulmani et al., "Lack of effect of the adenosine A1 receptor agonist, GR79236, on capsaicininduced CGRP release in anaesthetized pigs," Cephalalgia 25(11):1082-1090, Nov. 2005, 9 pages.

Arulmozhi et al., "Migraine: current concepts and emerging therapies," Vascul Pharmacol 43(3):176-187, Sep. 2005, 12 pages.

Asahina et al., "Specific induction of cAMP in Langerhans cells by calcitonin gene-related peptide: Relevance to functional effects," Proceed Nat Acad Sci USA 92(18):8323-8327, Aug. 1995, 5 pages.

Ashina et al., "Calcitonin gene-related peptide levels during nitric oxide-induced headache in patients with chronic tension-type headache," Eur J Neurol 8(2):173-178, Mar. 2001, 6 pages.

Ashina et al., "Evidence for increased plasma levels of calcitonin gene-related peptide in migraine outside of attacks," Pain 86(1-2):133-138, May 2000, 6 pages.

Ashina et al., "Plasma levels of calcitonin gene-related peptide in chronic tension-type headache," Neurology 55(9):1335-1340, Nov. 2000, 6 pages.

Ashina, "Calcitonin Gene-Related Peptide in Tention-Type Headache," The Scientific World 2:1527-1531, Jun. 2002, 6 pages.

Ashkenazi et al., "Headache management for the pain specialist," Regional Anethesia and Pain Medicine, vol. 29, No. 5, Sep.-Oct. 2004, 14 pages.

Ashkenazi et al., "The evoling management of migraine," Current Opinion in Neurology, Jun. 2003, 5 pages.

Askenazi et al., "Botulinum toxin and other new approached to migraine therapy," Annual Review of Medicine, vol. 55, Feb. 2004, 14 pages.

Aubree-Lecat et al., "Influence of Barrier-Crossing Limitations on the Amount of Macromolecular Drug Taken up by its Target", Journal of Pharmacokinetics and Biopharmaceutics 21 1 75-98, Feb. 1993, 24 pages.

Avastin (bevacizumab), "Prescribing Information," Feb. 2004, 27 pages.

Avastin® (bevacizumab) EMA, "Scientific Discussion," EMEA 2005, 61 pages.

Ayata et al., "Suppression of cortical spreading depression in migraine prophylaxis", Annals of Neurology 59(4):652-661, Apr. 2006, 10 pages.

Aziz, "Visceral hypersensitivity: fact or fiction," Gastroenterology 131(2):661-664, Aug. 2006, 4 pages.

Bahra et al., "Oral zolmitriptan is effective in the acute treatment of cluster headache," presented in part at the annual meeting of the American Academy of Neurology, Apr. 17-24, 1999, Neurology 54:1832-1839, May 2000, 8 pages.

Balint and Larrick, "Antibody engineering by parsimonious mutagenesis," Gene 137(1):109-118, Dec. 1993, 10 pages.

Ballabh et al., "The Blood-brain barrier: an overview—structure regulation and clinical implications," Neurobiology of Disease, vol. 16(1), 1-13, Jun. 2004, 13 pages.

Bard et al., "Peripherally administered antibodies against amyloid beta-peptide enter the central nervous system and reduce pathology in a mouse model of Alzheimer disease," Nat Med 6(8):916-919, Aug. 2000, 4 pages.

Benemei et al., "CGRP receptors in the control of pain and inflammation," Current Opinion in Pharmacology, 9:9-14, Feb. 2009, 6 pages.

Bennett et al., "Alleviation of mechanical and thermal allodynia by CGRP(8-37) in a rodent model of chronic central pain," Pain 86(1-2):163-175, May 2000, 13 pages.

Bergerot et al., "Animal models of migraine: looking at the component parts of a complex disorder", European Journal of Neuroscience 24(6):1517-1534, Sep. 2006, 18 pages.

Bexxar (131 I-tositumomab), "Prescribing Information," Corixa Corporation and GlaxoSmithKline, Jun. 2003, 49 pages.

(56) References Cited

OTHER PUBLICATIONS

Bigal et al., "Emerging drugs for lnigraine prophylaxis and treatment," MedGenMed 8(2): 31, May 4, 2006, 12 pages.
Bigal et al., "Migraine in the Triptan Era: Lessons From Epidemiology, Pathophysiology, and Clinical Science", Headache 49:S21-S33, Feb. 2009, 13 pages.
Bigal et al., "Migraine in the Triptan Era: Progresses achieved, lessons learned and future developments," Arquivos de Neuro-Psiquiatria 67(2-B):559-569, Jun. 2009, 11 pages.
Bigal et al., "New Migraine preventive options: an update with pathophysiological considerations," Rev Hosp Clin Fae Med Sao Paulo 57(6):293-298, Nov.-Dec. 2002, 6 pages.
Bird et al., "Single-chain antigen-binding proteins," Science 242(4877):423-426, Oct. 21, 1988, 5 pages.
Bjarnadottir, "Comprehensive repertoire and phylogenetic analysis of the G protein-coupled receptors in human and mouse", Genomics 88(3):263-273, Sep. 2006, 11 pages.
Boel et al., "Functional human monoclonal antibodies of all isotypes constructed from phage display library-derived single-chain Fv antibody fragments," Journal of Immunology Methods, vol. 236(1-2), May 2000, 14 pages.
Boerner et al., "Production of antigen-specific human monoclonal antibodies from in vitro-primed human splenocytes," J Immunol 147(1):86-95, Jul. 1, 1991, 10 pages.
Bolay et al., "Intrinsic brain activity triggers trigeminal meningeal afferents in a migraine model," Nature medicine 8(2):136, Feb. 2002, 7 pages.
Bousser and Welch, "Relation between migraine and stroke," Lancet Neurology, vol. 4, Sep. 2005, 10 pages.
Bowen et al., "Tumor necrosis factor-alpha stimulation of calcitonin gene-related peptide expression and secretion from rat trigeminal ganglion neurons," J Neurochem 96(1):65-77, Jan. 2006, 13 pages.
Boyce and Hill, "Substance P ($NK_1$) Receptor Antagonists—Analgesics or Not?" Handbook of Experimental Pharmacology Stress, Immunology and Behaviour, 2004, 23 pages.
Brain and Edvinsson, "Chapter 16: Calcitonin Gene-Related Peptide and Other Peptides," The Headaches, Third Edition, pp. 159-164, 2006, 8 pages.
Brain and Grant, "Vascular actions of calcitonin gene-related peptide and adrenomedullin," Physiol Rev 84(3):903-934, Jul. 2004, 32 pages.
Brain et al., "CGRP receptors: a headache to study, but will antagonists prove therapeutic in migraine?", Trends in Pharmaceutical Sciences 23(2): 51-53, Feb. 2002, 3 pages.
Brain et al., "Calcitonin Gene-Related Peptide is a Potent Vasodilator," Nature vol. 313: 54-56, Jan. 1985, 3 pages.
Brain, "Calcitonin gene-related peptide (CGRP) antagonists: blockers of neuronal transmission in migraine," Brit J Pharmacol 142(7):1053-1054, Aug. 2004, 2 pages.
Brandes et al., "Topiramate for Migraine Prevention," J Am Med Assoc 291(8):965-973, Feb. 25, 2004, 9 pages.
Breeze et al., "Solution structure of human calcitonin gene-reglated peptide by 1H NMR and distance geometry with retrained molecular dynamics," BioChemistry, vol. 30(2): 575-82, Jan. 1991, 8 pages.
Brekke and Sandlie, "Therapeutic Antibodies for Human Diseases at the Dawn of the Twenty-First Century," Nature Reviews, Drug Discovery, vol. 2, Jan. 2003, 11 pages.
British National Formulary, "British National Formulary, 52nd Edition," pp. 234-239, BMJ Publishing Group with RPS Publishing, Sep. 2006, 8 pages.
Brody et al., "Aptamers as therapeutic and diagnostic agents," Reviews in Molecular Biotechnology 74(1):5-13, Mar. 2000, 9 pages.
Brorson et al., "Mutational analysis of avidity and fine specificity of anti-levan antibodies," J Immunol 163(12):6694-6701, Dec. 15, 1999, 9 pages.
Brown and Morice, "Clinical Pharmacology of Vasodilator Peptides", Journal of Cardiovascular Pharmacology 10 Suppl 12:S82-87, Feb. 1987, 6 pages.

Bruera et al., "Cancer pain," JAMA 290(18):2476-2479, Nov. 12, 2003, 4 pages.
Braggemann et al., "Comparison of the Effector Functions of Human Immunoglobulins Using a Matched Set of Chimeric Antibodies," Journal of Exp. Med. 166: 1351-1361, Nov. 1987, 11 pages.
Brummell et al., "Probing the combining site of an anti-carbohydrate antibody by saturation-mutagenesis: role of the heavy-chain CDR3 residues," Biochemistry, 32(4):1180-1187, Feb. 2, 1993, 2 pages.
Buckley et al., "The partial inhibition of inflammatory responses induced by capsaicin using the Fab fragment of a selective calcitonin gene-related peptide antiserum in rabbit skin," Neuroscience 48(4):963-968, Jun. 1992, 6 pages.
Burks et al., "In vitro scanning saturation mutagenesis of an antibody binding pocket," Proc Natl Acad Sci USA 94(2):412-417, Jan. 21, 1997, 6 pages.
Burstein and Jakubowski, "Analgesic Triptan Action in an Animal Model of Intracranial Pain: A Race against the Development of Central Sensitization," Ann Neurol 55(1):27-36, Jan. 2004, 8 pages.
Burstein et al., "Defeating Migraine Paine with Triptans: A Race against the Development of Cutaneous Allodynia," Ann Neurol 55(1):19-26, Jan. 2004, 8 pages.
Buzzi and Moskowitz, "The Pathophysiology of Migraine: Year 2005," Journal of Headache Pain, vol. 6, pp. 105-111, Jun. 2005, 7 pages.
Buzzi et al., "The antimigraine drug, sumatriptan (GR43175), selectively blocks neurogenic plasma extravasation from blood vessels in dura mater," British Journal of Pharmacology, 99(1):202-206, Jan. 1990, 5 pages.
Bylund and Toews, "Radioligand Binding Methods: Practical Guide and Tips," Invited Review, American J. Physiological, 265: L421-L429, Nov. 1993, 9 pages.
Byrne, "Chapter 6: Neuromuscular and Synaptic Transmission," in Essential Medical Physiology, 3rd Edition, Elsevier Academic Press, Amsterdam, 2003, 28 pages.
Cady and Dodick, "Diagnosis and Treatment of Migraine," Mayo Clinical Proceedings, vol. 77, Mar. 2002, 7 pages.
Caekebeke et al., "The antimigraine drug sumatriptan increases blood flow velocity in large cerebral arteries during migraine attacks," Neurology, vol. 42, 1522-26, Aug. 1992, 6 pages.
Capel et al., "Heterogeneity of human IgG Fc receptors," Immunomethods 4(1):25-34, Feb. 1994, 10 pages.
Caraceni et al., "Pain measurement tools and methods in clinical research in palliative care: recommendations of an Expert Working Group of the European Association of Palliative Care," J Pain Symptom Manage 23(3):239-255, Mar. 2002, 17 pages.
Cardarelli et al., "Binding to CD20 by Anti-B 1 antibody or F(ab')(2) is Sufficient for Induction of Apoptosis in B-Cell Lines," Cancer Immunol. Immunother. 51: 15-24, Mar. 2002, 10 pages.
Carter et al., "Humanization of an Anti-p185HER2 Antibody for Human Cancer Therapy," Proceedings of the National Academy of Sciences of the United States of America, vol. 89, May 1992, 5 pages.
Carter, "Potent antibody therapeutics by design," Nature Reviews Immunology 6(5):343-57, May 2006, 20 pages.
Carter, "Improving the Efficacy of Antibody-Based Cancer Therapies," Nature Reviews Cancer, vol. 1, Nov. 2001, 12 pages.
Casset et al., "A peptide mimetic of an anti-CD4 monoclonal antibody by rational design," Biochem Biophys Res Commun 307(1):198-205, Jul. 18, 2003, 8 pages.
Catty, "Antibodies vol. 1: A practical approach," Chapter 1-4, Practical Approach Series, 1988, 90 pages.
Catty, "Antibodies vol. II: A Practical Approach," Chapter 4: ELISA and related enzyme immunoassays, 1989, 60 pages.
Cervero et al., "Visceral pain," Lancet 353(9170):2145-2148, Jun. 19, 1999, 4 pages.
Chakder and Rattan, "[$Tyr^0$]-Calcitonin Gene-Related Peptide 28-37 (Rat) as a Putative Antagonist of Calcitonin Gene-Related Peptide Response son Opossum Internal Anal Sphincter Smooth Muscle," J Pharm and Exper Therapeutics, 1990, 253(1): 200-206.

(56) References Cited

OTHER PUBLICATIONS

Chapman, "PEGylated antibodies and antibody fragments for improved therapy: a review," Advanced Drug Deliv. Rev., vol. 54(4): 531-545, Jun. 2002, 15 pages.
Chapman, "Therapeutic antibody fragments with prolonged in vivo half-lives," Nature America, Nature BioTechnology, vol. 17, Aug. 1999, 4 pages.
Chen et al., "Generation and analysis of random point mutations in an antibody CDR2 sequence: many mutated antibodies lose their ability to bind antigen," J Exp Med 176(3):855-866, Sep. 1992, 12 pages.
Chen et al., "Selection and analysis of an optimized anti-VEGF antibody: crystal structure of an affinity-matured Fab in complex with antigen," J Mol Biol 293(4):865-881, Nov. 5, 1999, 17 pages.
Chen et al., "Use of Constitutive G Protein-Coupled Receptor Activity for Drug Discovery," Molecular Pharmacology 57(1):125-134, Jan. 2000, 10 pages.
Chen, "Enhancement and destruction of antibody function by somatic mutation: unequal occurrence is controlled by V gene combinatorial associations", EMBO Journal 14(12):2784-2794, Jun. 1995, 11 pages.
Chester and Hawkins, "Clinical Issues in Antibody Design," Trends Biotechnol. vol. 13: 294-300, Aug. 1995, 7 pages.
Chiba et al., "Calcitonin gene-related peptide receptor antagonist human CGRP-(8-37)," American Journal of Physiology: Endocrine and Metabolism, vol. 256:E331-35, Feb. 1989, 7 pages.
Chothia et al., "Conformations of immunoglobulin hypervariable regions," Nature 342(6252):877-883, Dec. 21-28, 1989, 7 pages.
Cittadini et al., "Effectiveness of intranasal zolmitriptan in acute cluster headache. A randomized, placebo-controlled, double-blind crossover study", Archives of Neurology 63:1537-1542, Nov. 2006, 6 pages.
Clynes et al., "Fc receptors are required in passive and active immunity to melanoma," Proc Natl Acad Sci USA 95(2):652-656, Jan. 20, 1998, 5 pages.
Cole et al., "The EBV-hybridoma technique and its application to human lung cancer," Monoclonal Antibodies and Cancer Therapy 27:77-96, 1985, 20 pages.
Cole et al., "Human IgG2 Variants of Chimeric Anti-CD3 are Nonmitogenic to T cells," J. Immunol. 159: 3613-3621, 1997, 10 pages.
Colman, "Effects of amino acid sequence changes on antibody-antigen interactions," Res Immunol 145(1):33-36, Jan. 1994, 4 pages.
Conner et al., "Characterization of CGRP Receptor Binding", Current Protocols in Pharmacology 24:1-30, Sep. 2004, 11 pages.
Conner et al., "Interaction of calcitonin-gene-related peptide with its receptors," Biochem Soc Trans 30(4):451-455, Aug. 2002, 5 pages.
Connor et al., "GR205171 Clinical Study Group: Clinical evaluation of a novel, potent, CNS penetrating NK receptor antagonist in the acute treatment of migraine," Cephalalgia 18, 1998, 1 page.
Connor et al., "Interaction of calcitonin-gene-related peptide with its receptors," Biochemical Scoeity Transactions, vol. 30, Part 4, Aug. 2002, 5 pages.
Correia, "Stability of IgG isotypes in serum," mAbs 2(3):221-232, May/Jun. 2010, 12 pages.
Covell et al., "Pharmacokinetics of monoclonal immunoglobulin G1, F(ab')2, and Fab' in mice," Cancer Res 46(8):3969-3978, Aug. 1986, 10 pages.
Creamer et al., "Pain Mechanisms in Osteoarthritis of the Knee: Effect of Intraarticular Anesthetic," J Rheumtology, 1996, 23(6): 1031-1036.
Cruickshank et al., "β-Adrenoreceptor-Blocking Agents and the Blood-Brain Barrier," Clinical Science, pp. 453s-455s, vol. 59, Dec. 1980, 3 pages.
Cumberbatch et al., "Differential effects of the 5HT 1B/1D receptor agonist naratriptan on trigeminal versus spinal nociceptive responses," Cephalalgia 18:659-663, Dec. 1998, 5 pages.

Cumbethatch et al., "Dural vasodilation causes a sensitization of rat caudal trigeminal neurones in vivo that is blocked by a 5-HT$_{1B/1D}$ agonist," British Journal of Pharmacology 126:1478-1486, 1999, 9 pages.
Cumberbatch et al., "Reversal of behavioral and electrophysiological correlates of experimental peripheral neuropathy by the NK1 receptor antagonist GR205171 in rats," Neuropharmacology 37:1535-1543, Dec. 1998, 9 pages.
Cumberbatch et al., "Rizatriptan has central antinociceptive effects against durally evoked responses", European Journal of Pharmacology 328:37-40, Jun. 1997, 4 pages.
Cumberbatch et al., "The effects of 5-HT1A, 5-HT1B and 5-HT1D receptor agonists on trigeminal nociceptive neurotransmission in anaesthetized rats", European Journal of Pharmacology 362(1):43-46, Nov. 1998, 4 pages.
Cutrer et al., "Priorities for triptan treatment attributes and the implications for selecting an oral triptan for acute migraine: a study of US primary care physicians (the TRIPSTAR Project)", Clinical Therapeutics 26:1533-1545, Sep. 2004, 13 pages.
D.H.E. 45 and Migranal (dihydroergotamine mesylate, USP), "Prescribing Information," Novartis, N5-929 S-032 S-033, Jul. 31, 2002, 37 pages.
D'Amico et al., "When should "chronic migraine" be considered "refractory" to pharmacological prophylaxis?" Neurol Sci Suppl. 1:S55-S58, 2008, 4 pages.
Dahlof et al., "Within-patient consistency of response of rizatriptan for treating migraine," Neurology vol. 55, 1511-1516, Nov. 2000, 7 pages.
D'Amico and Tepper, "Prophylaxis of migraine: general principles and patient acceptance", Neuropsychiatric Disease and Treatment 4(6):1155-1167, Dec. 2008, 14 pages.
Davies and Riechmann, "Affinity improvement of single antibody VH domains. residues in all three hypervariable regions affect antigen binding," Immunotechnology 2(3):169-179, Sep. 1996, 11 pages.
Davis et al., "Fundamentals of Neurologic Disease," pp. 204-207, Demos Medical Publishing Inc., 2005, 6 pages.
Davis et al., "The Tortuous Road to an Ideal CGRP function blocker for the treatment of migraine", Current Topics in Medicinal Chemistry 8(16):1468-1479, Nov. 2008, 12 pages.
Davletov et al., "Beyond BOTOX: advantages and lilnitations of individual botulinum neurotoxins," Trends Neurosci 28(8):446-452, Aug. 2005, 7 pages.
De Felice et al., "Opiate-induced persistent pronociceptive trigeminal neural adaptations: potential relevance to opiate-induced medication overuse headache," Cephalalgia 29(12):1277-1284, May 2009, 9 pages.
De Haas et al., "Fc gamma receptors of phagocytes," J Lab Clin Med 126(4):330-341, Oct. 1995, 12 pages.
De Pascalis et al., "Grafting of "abbreviated" complementarity-determining regions containing specificity-determining residues essential for ligand contact to engineer a less immunogenic humanized monoclonal antibody," J Immunol 169(6):3076-3084, Sep. 15, 2002, 9 pages.
De Prado et al., "CGRP receptor antagonists: a new frontier of anti-migraine medications," Drug Discovery Today: Therapeutic Strategies, Nervous System Disorders, vol. 3, No. 4, Winter 2006, 5 pages.
De Vries et al., "Genetic biomarkers of migraine," Headache, Jul.-Aug. 2006, 10 pages.
Dechant et al., "IgA antibodies for cancer therapy," Critical Review in Oncology/Hematology vol. 39, Jul.-Aug. 2001, 9 pages.
Deckert-Schluter et al., "Crucial role of TNF receptor type-1 (p55), but not of TNF receptor type-2 (p75) in murine toxoplasmosis," Journal of Immunology, vol. 160: 3427-3436, Jul. 1990, 11 pages.
Declaration of Dr. Jes Olesen No. 3 regarding EP1957106, dated Jun. 12, 2017, 20 pages.
Delafoy et al., "Interactive involvement of brain derived neurotrophic factor, nerve growth factor, and calcitonin gene related peptide in colonic hypersensitivity in the rat," Gut 55(7):940-945, Jul. 2006, 6 pages.
Deleu, "Guidelines for the prevention of migraine," Saudi Med J 20(7):495-500, Jul. 1999.

(56) References Cited

OTHER PUBLICATIONS

Delves et al, "Chapter 3: Antibodies," in Roitt's Essential Immunology, Blackwell Publishing, 2006, 24 pages.
Denekas et al., "Inhibition of stimulated meningeal blood flow by a calcitonin gene-related peptide binding mirror-image RNA oligonucleotide," Brit J Pharmacol 148(4):536-543, Jun. 2006, 8 pages.
Dennis et al., "hCGRP8-37: a calcitonin gene-related peptide antagonist revealed calcitonin gene-related peptide receptor heterogeneity in brain and periphery," Journal of Pharmacology Exp. Ther. vol. 254(1), Jul. 1990, 6 pages.
Dennis et al., "Structure-Activity Profile of Calcitonin Gene-Related Peptide in Peripheral and Brain Tissues. Evidence for Receptor Multiplicity," The Journal of Pharmacology and Experimental Therapeutics 251(2):718-725, 1989, 8 pages.
Dhondt et al., "Pain Threshold in Patients with Rheumatoid Arthritis and Effect of Manual Oscillations," Scand J Rheumatol, 1999, 28: 88-93.
Di Angelantonio et al., "A Novel Class of Peptides with Facilitating Action on Neuronal Nicotinic Receptors of Rat Chromaffin Cells in Vitro: Functional and Molecular Dynamic Studies," Molecular Pharmacology 61(1):43-54, 2002, 12 pages.
Diener et al., "RPR100893, a Substance-P antagonist, is not effective in the treatment of migraine attacks," Cephalalgia, vol. 23, Apr. 2003, 3 pages.
Djavadi-Ohaniance et al., "Chapter 4: Measuring Antibody Affinity in Solution," in Antibody Engineering: A Practical Approach 77-117, 1st ed. 1996, 42 pages.
Dockray et al., "Immunoneutralization studies with calcitonin gene-related peptide," Ann N Y Acad Sci 657:258-267, Jun. 30, 1992, 10 pages.
Dodick and Silberstein, "Central sensitization theory of migraine: clinical implications," Headache, Nov. 2006, 10 pages.
Dodick et al., "Botulinum neurotoxin for the treatment of migraine and other primary headache disorders," Clinics in Dermatology, Apr. 2004, 6 pages.
Dodick et al., "Cardiovascular tolerability and safety of triptans: a review of clinical data," Headache, May 2004, 11 pages.
Dodick et al., "Cluster Headache," Cephalalgia, Nov. 2000, 17 pages.
Dodick et al., "Consensus Statement: Cardiovascular Safety Profile of Triptans (5-HT1B/1D Agonists) in the Acute Treatment of Migraine," Headache 44(5):414-425, May 2004, 12 pages.
Dodick et al., "Is there a preferred triptan?" Headache, Jan. 2002, 7 pages.
Dodick et al., "Predictors of migraine headache recurrence: a pooled analysis from the eletriptan database," Headache, vol. 48(2), 184-193, Feb. 2008, 10 pages.
Dodick et al., "Prioritizing treatment attributes and their impact on selecting an oral triptan: results from the TRIPSTAR project," Current Pain and Headache Reports 8:435-442, Dec. 2004, 8 pages.
Doenicke et al., "Possible benefit of GR43175, a novel 5-HT1-like receptor agonist, for the acute treatment of severe migraine," Lancet vol. 331 No. 8598, Jun. 11, 1988, 3 pages.
Dong et al., "Calcitonin gene-related peptide can be selected as a predictive biomarker on progression and prognosis of knee osteoarthritis," International Orthopaedics, Mar. 2015, 7 pages.
Doods et al., "Pharmacological profile of BIBN4096BS, the first selective small molecule CGRP antagonist," Brit J Pharmacol 129(3):420-423, Feb. 2000, 4 pages.
Doods, "Development of CGRP antagonists for the treatment of migraine," Current Opinion in Investigation Drugs, Sep. 2001, 8 pages.
Dressler et al., "Botulinum toxin: mechanisms of action," Eur Neurol 53(1):3-9, 2005, 6 pages.
Drossman et al., "Functional Bowel Disorders, a multicenter comparison of health status and development of illness severity index," Digestive Diseases and Sciences 40(5):986-995, May 1995.
Dufner et al., "Harnessing phage and ribosome display for antibody optimisation," Trends Biotechnol 24(11):523-529, Nov. 2006, 7 pages.

Durham and Russo, "Regulation of Calcitonin Gene-Related Peptide Secretion by a Serotonergic Antimigraine Drug," Journal of Neuroscience, vol. 19, pp. 3423-3429, May 1, 1999, 7 pages.
Durham et al., "CGRP-receptor antagonists—a fresh approach to migraine therapy?" N Eng J Med 350(11):1073-1075, Mar. 11, 2004, 3 pages.
Durham, "Calcitonin Gene-Related Peptide (CGRP) and Migraine," Emerging Neural Theories of Migraine Pathogenesis, Headache 46(1): S3-S8, Jun. 2006, 6 pages.
Durham, "CGRP receptor antagonists: A new choice for acutre treatment of migraine?" Current Opinion in Investigational Drugs 5(7):731-735, Jul. 2004, 5 pages.
Durham, "Inhibition of Calcitonin Gene-Related Peptide Function: A Promising Strategy for Treating Migraine," Headache 38(8):1269-1275, Sep. 2008, 7 pages.
Duvernoy and Risold, "The circumventricular organs: An atlas of comparative anatomy and vascularization," Brain Research Reviews vol. 56(1), Nov. 2007, 29 pages.
Ebersberger et al., "Release of Substance P, Calcitonin Gene-Related Peptide and Prostaglandin E2 from Rat Dura Mater Enchephali Following Electrical and Chemical Stimulation in Vitro," Neuroscience, vol. 89(3):901-907, Mar. 1999, 7 pages.
Edelmayer et al., "Medullary pain facilitating neurons mediate allodynia in headache-related pain," Ann Neurol 65(2):184-193, Feb. 2009, 22 pages.
Edvinsson and Goadsby, "Neuropeptides in migraine and cluster headache," Cephalalgia vol. 14, 1994, 8 pages.
Edvinsson and Hargreaves, "Chapter 31: CGRP Involvement in Migraines," in The Headaches, Third Edition, pp. 289-299, 2006, 13 pages.
Edvinsson and Tfelt-Hansen, "The blood-brain barrier in migraine treatment," Cephalalgia 28(12):1245-1258, Dec. 2008, 14 pages.
Edvinsson and Uddman, "Neurobiology in primary headaches," Brain Res Rev 48(3):438-456, Jun. 2005, 19 pages.
Edvinsson et al. "Characterisation of the effects of a non-peptide CGRP receptor antagonist in SK-N-MC cells and isolated human cerebral arteries," European Journal of Pharmacology 415:39-44, 2001, 6 pages.
Edvinsson et al., "Amylin localisation effects on cerebral arteries and on local cerebral blood flow in the cat," Scientific World Journal, vol. 1: 168-180, May 2001, 14 pages.
Edvinsson et al., "Calcintonin Gene-Releated Peptide (CGRP) in Cerebrovascular Disease," Scientific World Journal, vol. 2, May 30, 2002, 7 pages.
Edvinsson et al., "Effect of the CGRP receptor antagonist BIBN4096BS in human cerebral., coronary and omental arteries and in SK-N-MC cells," Eur J Pharmacol 434(1-2):49-53, Jan. 2, 2002, 5 pages.
Edvinsson et al., "Inhibitory effect of BIBN4096BS, CGRP8-37, a CGRPantibody and an RNA-Spiegelmer on CGRP induced vasodilatation in the perfused and non-perfused rat middle cerebral artery," Brit J Pharmacol 150(5):633-640, Mar. 2007, 8 pages.
Edvinsson et al., "Innervation of the human middle meningeal artery immunohistochemistry, ultrastructure, and role of endotherlium for vasomotility," Peptides vol. 19(7), 1998, 13 pages.
Edvinsson, "Blockade of CGRP receptors in the intracranial vasculature: a new target in the treatment of headache," Cephalalgia 24:611-622, 2004, 12 pages.
Edvinsson, "CGRP blockers in migraine therapy: where do they act?" Brit J Pharmacol 155(7):967-969, Dec. 2008, 3 pages.
Edvinsson, "Clinical Data on the CGRP Antagonist BIBN4096BS for Treatment of Migraine Attacks," CNS Drug Reviews 11(1):69-76, Mar. 2005, 8 pages.
Edvinsson, "New therapeutic target in primary headaches—blocking the CGRP receptor," Expert Opinion Ther Targets 7(3):377-338, Jun. 2003, 7 pages.
Edvinsson, "Novel migraine therapy with calcitonin gene-regulated peptide receptor antagonists", Expert Opinion on Therapeutic Targets 11(9):1179-1188, Sep. 2007, 11 pages.
Ekbom et al., "Treatment of Acute Cluster Headache with Sumatriptan," New England Journal of Medicine, vol. 325(5), Aug. 1, 1991, 5 pages.
Elgert, "Immunology: Understanding the Immune System," 1st Edition, 58-78, Wiley-Liss Inc, 1996, 24 pages.

(56) References Cited

OTHER PUBLICATIONS

Elshourbagy et al., "Molecular cloning and characterization of the porcine calcitonin gene-related peptide receptor," Endocrinology 139(4):1678-1683, Apr. 1998, 6 pages.
Emilien and Maloteaux, "Current Therapeutic Uses and Potential of β-Adrenoreceptor Agonists and Antagonists," European Journal of Clinical Pharmacology, vol. 53, pp. 389-404, Feb. 1998, 16 pages.
Encyclopedia of Pain, "C," Schmidt and Willis (Eds.), 2007, 187-526.
EP Opposition, "Declaration of Dr. John Bradley," EP Opposition of Appln. No. 09716779.5, dated Sep. 30, 2018, 27 pages.
Escott and Brain, "Effect of a calcitonin gene-related peptide antagonist ($CGRP_{8-37}$) on skin vasodilatation and oedema induced by stimulation of the rat saphenous nerve," Brit J Pharmacol 110(2):772-776, Oct. 1993, 5 pages.
Escott et al., "Trigeminal ganglion stimulation increases facial skin blood flow in the rat: a major role for calcitonin gene-related peptide," Brain Res 669(1):93-99, Jan. 9, 1995, 7 pages.
Evers et al., "EFNS guideline on the drug treatment of migraine—report of an EFNS task force," European Journal of Neurology 13:560-572, Jun. 2006, 13 pages.
Evidence of Publication Date of Edvinsson, CNS Drug Reviews 11(1):69-76, 2005, 1 page.
Extended European Search Report issued in European Application No. 18192502.5 dated Dec. 4, 2018, 12 pages.
Fanciullacci et al., "Increase in plasma calcitonin gene-related peptide from the extracerebral circulation during nitroglycerin-induced cluster headache attack," Pain 60(2):119-123, Feb. 1995, 5 pages.
Faraci et al., "Vascular responses of dura mater," American Journal of Physiology, Jul. 1989, 5 pages.
Felson et al., "The American College of Rheumatology preliminary core set of disease activity measures for rheumatoid arthritis clinical trials. The Committee on Outcome Measures in Rheumatoid Arthritis Clinical Trials," Arthritis Rheum 36(6):729-740, Jun. 1993, 12 pages.
Felson et al., "The Association of Bone Marrow Lesions with Pain in Knee Osteoartritis," Annals of Internal Medicine, Apr. 2001, 134(7): 541-549.
Feniuk et al., "The selective carotid arterial vasoconstrictor action of GR43175 in anaesthetized dogs," British Journal of Pharmacology 96(1):83-90, Jan. 1989, 8 pages.
Fernihough et al., "Regulation of calcitonin gene-related peptide and TRPV1 in a rat model of osteoarthritis," Neuroscience Letters, 2005, 388: 75-80.
Ferrara et al., "Discovery and Development of Bevacizumab, an Anti-VEGF Antibody for Treating Cancer," Nature Review Drug Discovery, vol. 3: 391-400, May 2004, 10 pages.
Ferrari et al., "5-HT1 receptors in migraine pathophysiology and treatment," European Journal of Neurology vol. 2(1):5-21, Mar. 1995, 17 pages.
Ferrari et al., "Acute treatment of migraine attacks," Current Opinion in Neurology, 8(3):237-4, Jun. 1995, 6 pages.
Ferrari et al., "Cerebral blood flow during migraine attacks without aura and effect of sumatriptan," Arch Neurol vol. 135-139, Feb. 1995, 5 pages.
Ferrari et al., Clinical and experimental effects of sumatriptan in humans. Trends in Pharmacol Sci 14:129-133, Apr. 1993, 5 pages.
Ferrari et al., "Clinical effects and mechanism of action of sumatriptan in migraine," Clinical Neurology and Neurosurgery, 94(suppl):S73-S77, 1992, 5 pages.
Ferrari et al., "Combinatie van een triptaan met een NSAID bij migraine," Ned Tijdsch Geneeskd, 151, 36, Sep. 2007, 2 pages.
Ferrari et al., "Efficacy of ICS 205-930, a novel 5-Hydroxytlyptamine3 (5HT3) receptor antagonist, in the prevention of migraine attacks. A complex answer to a simple question," Pain vol. 45:283-291, Jun. 1991, 9 pages.
Ferrari et al., "From molecules to migraine patient," proceedings of the 2nd International Congress of the European Headache Federation in Liege, Jun. 1994, Cephalalgia Oct. 1995, 43 pages.

Ferrari et al., "Methionine-Enkephalin in migraine and tension headache. Differences between classic migraine, common migraine and tension headache, and changes during attacks," presented in part at the 6th International Migraine Symposium, Oct. 1986, Headache 30:160-164, 1990, 5 pages.
Ferrari et al., "Monoamine oxidase, phenosulphotransferase and serotonin metabolism in common and classic migraine and tension headache," Cephalalgia 7,suppl.6:144-146, 1987, 3 pages.
Ferrari et al., "Neuro-excitatory plasma aminoacids are elevated in migraine," Neurology 40:1582-1586, Oct. 1990, 5 pages.
Ferrari et al., "Oral sumatriptan: effect of a second dose, incidence and treatment of headache recurrences," Cephalalgia 14:330-338, Oct. 1994, 9 pages.
Ferrari et al., "Oral triptans (serotonin 50HT 1B/1D agonists) in acute migraine treatment: a meta-analysis of 53 trials," The Lancet 358(9294):1668-175, Nov. 2001, 8 pages.
Ferrari et al., "Plasma aminoacids in common and classic migraine and tension headache," Cephalalgia vol. 7, suppl.6:246-247, 1987, 2 pages.
Ferrari et al., "Release of platelet Met-enkephalin, but not serotonin, in migraine. A platelet-response unique to migraine patients?" Journal of the Neurological Sciences, vol. 93:51-60, Oct. 1989, 10 pages.
Ferrari et al., "Sumatriptan in the treatment of migraine," Neurology 1993;43(suppl 3):S43-47, Jun. 1993, 6 pages.
Ferrari et al., "The genetics of migraine: implication for treatment approaches," J Neural Transm Suppl. (63):111-27, 2002, 18 pages.
Ferrari et al., "The use of multiattribute decision models in evaluating triptan treatment options in migraine," J Neurology 252:1026-1032, Sep. 2005, 7 pages.
Ferrari et al., "Triptan medications to treat acute migraine," Lancet vol. 359: 1152-53, Mar. 30, 2002, 1 page.
Ferrari et al., "Triptans (serotonin, 5-HT 1B/1D agonists) in migraine: detailed results and methods of a meta-analysis of 53 trials," Cephalalgia 22(8):633-658, Oct. 2002, 26 pages.
Ferrari, "Should we advise patients to treat migraine attacks early: methodologic issues," European Neurology, vol. 53, suppl 1, May 3, 2005, 5 pages.
Ferrari, "311C90: Increasing the options for therapy with effective acute antimigraine 5HT1B/1D receptor agonists," Neurology, Mar. 1997, 4 pages.
Ferrari, "Current perspectives on effective migraine treatments: are small clinical differences important for patients?" Drugs of Today (Barc) vol. 39 Suppl D:37-41, 2003, 4 pages.
Ferrari, "From genetics to prophylaxis," Cephalalgia 17(suppl 17):2-5, Jun. 1997, 4 pages.
Ferrari, "How to assess and compare drugs in the management of migraine: success rates in terms of response and recurrence," Cephalalgia, 19 Suppl 23:2-8, Mar. 1999, 7 pages.
Ferrari, "Migraine," Lancet, vol. 351, Apr. 4, 1998, 9 pages.
Ferrari, "Rizatriptan: a new milestone in migraine treatment. Introduction," Cephalalgia 20 Suppl 1:1, Nov. 2000, 19 pages.
Ferrari, "Should we advise patients to treat migraine attacks early?" Cephalalgia, Nov. 2004, 3 pages.
Ferrari, "The clinical effectiveness of 311C90 in the acute treatment of migraine," Eur Neurol 36(suppl 2):4-7, 1996, 4 pages.
Ferrari, "Treatment of migraine attacks with sumatriptan: The Subcutaneous Sumatriptan International Study Group," the New England Journal of Medicine, vol. 325:316-321, Aug. 1, 1991, 6 pages.
Ferro et al., "A comparison of the contractile effects of 5-hydroxytryptamine, sumatriptan and MK-462 on human coronary artery in vitro," British Journal of Pharmacology 40(3):245-251, Sep. 1995, 7 pages.
Fischer et al., "The Nonpeptide Calcitonin Gene-Related Peptide Receptor Antagonist BIBN4096BS Lowers the Activity of Neurons with Meningeal Input in the Rat Spinal Trigeminal Nucleus," J Neurosci 25(25):5877-5883, Jun. 22, 2005, 7 pages.
Fitzgibbon and Loeser, "Section 1: Assessment and Diagnosis. Causes of Pain in the Cancer Patient," Cancer Pain, 2010, p. 18.
Flower, "Modelling G-protein-coupled receptors for drug design," Biochimica et Biophysica Acta 1422: 207-234, Nov. 1999, 28 pages.

(56) References Cited

OTHER PUBLICATIONS

Flynn et al., "The Johns Hopkins White Papers: Arthritis," Johns Hopkins Medicine, 2007, 72 pages.
Foord and Craig, "Isolation and characterisation of a human calcitonin-gene-related-peptide receptor," European Journal of Biochemistry 170 1-2 373-9, Dec. 1987, 7 pages.
Foord et al., "New methods for researching accessory proteins," Journal of Molecular Neuroscience, vol. 26, Issue 2-3, Jun. 2005, 12 pages.
Foote et al., "Antibody Framework Residues Affecting the Conformation of the Hypervariable Loops," Journal of Molecular Biology, vol. 224, Mar. 1992, 13 pages.
Forster and Dockray, "The role of calcitonin gene-related peptide in gastric mucosal protection in the rat," Exp Physiol 76(4):623-626, Jul. 1991, 4 pages.
Foulkes et al., "Differential vasodilator profile of calcitonin gene-related peptide in porcine large and small diameter coronary artery rings," European Journal of Pharmacology, 201, 143-149, Aug. 1991, 7 pages.
Francis et al., "The irritable bowel severity scoring system: a simple method of monitoring irritable bowel syndrome and its progress," Aliment Pharmacol Ther 11(2):395-402, Apr. 1997, 8 pages.
Friend et al., "Phase I Study of an Engineered Aglycosylated Humanized CD3 Antibody in Renal Transplant Rejection," Transplantation vol. 68, No. 11, Dec. 15, 1999, 6 pages.
Fries et al., "The dimensions of health outcomes: the health assessment questionnaire, disability and pain scales," J Rheumatol 9(5):789-793, Sep.-Oct. 1982, 6 pages.
Frobert et al. "A sensitive sandwich enzyme immunoassay for calcitonin gene-related peptide (CGRP): characterization and application," Peptides 20(2):275-284, Feb. 1999, 10 pages.
Gallai et al., "Vasoactive peptide levels in the plasma of young migraine patients with and without aura assessed both interictally and ictally," Cephalalgia 15(5):384-390, Oct. 15, 1995, 7 pages.
Gardiner et al., "Antagonistic effect of Human α-CGRP [8-37] on the in vivo regional haemodynamic actions of human α-CGRP," Biochemical and Biophysical Research Communications 171(3):938-943, Sep. 28, 1990, 6 pages.
Gardiner et al., "Haemodynamic effects of human α-calcitonin gene-related peptide following administration of endothelin-1 or NG-nitro-L-arginine methyl ester in conscious rats," British Journal of Pharmacology 103(1):1256-662, May 1991, 7 pages.
Gardiner et al., "Regional haemodynamic effects of calcitonin gene-related peptide," American Journal of Physiology-Regulatory, Integrative and Comparative Physiology 256(2):R332-R338, Feb. 1989, 7 pages.
Gardiner et al., "Regional haemodynamic effects of human α- and β-calcitonin gene-related peptide in conscious Wistar rats," British Journal of Pharmacology 98(4):1225-132, Dec. 1989, 8 pages.
Garg and Balthasar, "Investigation of the Influence of FcRn on the distribution of IgG to the brain," The AAPS Journal, vol. II, No. 3 553-557, Sep. 2009, 5 pages.
Garlick and Renkin, "Transport of large molecules from plasma to interstitial fluid and lymph in dogs," American Journal of Physiology vol. 219, No. 6, Dec. 1970, 11 pages.
Gavilondo and Larrick, "Antibody Engineering at the Millennium," BioTechniques 29: 128-145, Jul. 2000, 15 pages.
Gay et al., "Interleukin-6 genetic ablation protects from trinitrobenzene sulfonic acid-induced colitis in mice," NeuroImmunoModulation 13(2):114-121, 2006, 8 pages.
GE Healthcare, "Biacore Sensor Surface Handbook," BR-1005-71 Edition AB, 2005, 100 pages.
Geerligs et al., "The influence of different adjuvants on the immune response to a synthetic peptide comprising amino acid residues 9-21 of herpes simplex virus type 1 glycoprotein D.," Journal of Immunological Methods, vol. 124, 95-102, Nov. 1989, 8 pages.
Geppetti et al., "CGRP and migraine: neurogenic inflammation revisited," J Headache Pain 6(2):61-70, Apr. 2005, 10 pages.

Ghatta et al., "Calcitonin gene related peptide: Understanding its role," Indian Journal of Pharmacology, vol. 36, Issue 5, Oct. 2004, 7 pages.
Giffin et al., "Effect of the adenosine A 1 receptor agonist GR79236 on trigeminal nociception with blink reflex recordings in healthy human subjects," Cephalalgia 23(4):287-292, May 2003, 6 pages.
Gijsman et al., "Dihydoergotamine nasal spray," Neurology 45:397-98, Feb. 1995, 2 pages.
Gijsman et al., "Double-blind, placebo-controlled, dose-finding study of rizatriptan (MK-462) in the acute treatment of migraine," Cephalalgia 17:647-51, Oct. 1997, 9 pages.
Gijsman et al., "Pharmacokinetic and pharmacodynamic profile of oral and intravenous meta-chlorophenylpiperazine in healthy volunteers," J Clin Psychopharmacol 1998;18:289-95, Aug. 1998, 14 pages.
Goadsby and Boes, "Chronic daily headache," J Neurol Neurosurg Psychiatry 72(Suppl II):ii2-ii5, Jun. 2002, 4 pages.
Goadsby and Boes, "New daily persistent headache," Journal of Neurology Neurosurgery Psychiatry 72(Suppl II): ii6-ii9, Jun. 2002, 4 pages.
Goadsby and Edvinsson, "Human in vivo Evidence for Trigeminovascular Activation in Cluster Headache:-Neuropeptide Changes and Effects of Acute Attacks Therapies," Brain vol. 117: 427-434, 1994, 8 pages.
Goadsby and Edvinsson, "The Trigeminovascular System and Migraine: Studies Characterizing Cerebrovascular and Neuropeptide Changes Seen in Humans and Cats," Annals of Neurology, 33(1): 48-56, Jan. 1993, 9 pages.
Goadsby and Hargreaves, "Refractory Migraine and Chronic Migraine: Pathophysiological Mechanisms", Headache 48:799-804, 2008, 8 pages.
Goadsby and Kernick, "Chapter 4: The migraine attack," in Headache: A Practical Manual (Oxford Care Manuals) 2009, 18 pages.
Goadsby and Ramadan, "Potential New Drugs for Acute and Prophylactic Treatment of Migraines," The Headaches, 3rd Edition, Chapter 60, 569-576, 2006, 8 pages.
Goadsby et al., "Chapter 6: Treatment of headache and prophylaxis," in The Effective of Management written by Andrew Dowson, Aesculapius Medical Press, 1999, 16 pages.
Goadsby et al., "Chapter 61: Migraine," in Diseases of the Nervous System: Clinical Neuroscience and Therapeutic Principles, Third Edition, vol. I, 2002, 9 pages.
Goadsby et al., "Extracranial vasodilatation mediated by vasoactive intestinal polypeptide (VIP)," Brain Research 329(1-2):285-288, Mar. 1985, 4 pages.
Goadsby et al., "Mechanisms and Management of Headache," CMENeurology—I, Journal of Royal College of Physicians of London, vol. 33, No. 3, pp. 228-234, May-Jun. 1999, 7 pages.
Goadsby et al., "Migraine—Current Understanding and Treatment," N Eng J Med 346(4):257-270, Jan. 24, 2002, 14 pages.
Goadsby et al., "Towards a definition of intractable headache for use in clinical practice and trails," Cephalalgia, vol. 26: 1168-1170, Sep. 2006, 3 pages.
Goadsby et al., "Treatment of a Migraine," New England Journal of Medicine, vol. 347, No. 10, Sep. 5, 2002, 3 pages.
Goadsby et al., "Tripstar: Prioritizing triptan treatment attributes in migraine management," Acta Neurologica Scandinavica 110:137-143, Sep. 2004, 7 pages.
Goadsby et al., "Vasoactive peptide release in the extracerebral circulation of humans during migraine headache," Ann Neurol 28(2):183-187, Aug. 1990, 5 pages.
Goadsby, "Advances in the understanding of headache," British Medical Bulletin 73-74:83-92, Jan. 2005, 10 pages.
Goadsby, "Calcitonin Gene-Related Peptide Antagonists as Treatments of Migraine and Other Primary Headaches," Drugs 65(18):2557-2567, Dec. 2005, 11 pages.
Goadsby, "Can we Develop Neurally Acting Drugs for the Treatment of Migraine?" Nat Rev Drug Discov 4:741-750, Sep. 2005, 10 pages.
Goadsby, "Chapter 55: Primary neurovascular headache," in Textbook of Pain Wall and Melzack Neurovascular Headache, pp. 851-874, 2006, 24 pages.

(56) References Cited

OTHER PUBLICATIONS

Goadsby, "Cortical Spreading Depression—Better Understanding and More Questions," Journal of Neurophysiol. vol. 97, Apr. 4, 2007, 1 page.
Goadsby, "Efficacy and safety of topiramate for the treatment of chronic migraine: a randomized, double-blind placebo-controlled trial", Headache 47(2):170-180, Feb. 2007, 11 pages.
Goadsby, "Eletriptan in acute migraine: a double-blind, placebo-controlled comparison to sumatriptan," Neurology 54:156-163, Jan. 2000, 8 pages.
Goadsby, "Migraine Pathophysiology," Headache vol. 45(Suppl. 1), Apr. 2005, 11 pages.
Goadsby, "Migraine, Aura, and Cortical Spreading Depression: Why are we still talking about it?" Annals of Neurology 49(1):4-6, Jan. 2001, 3 pages.
Goadsby, "Migraine: emerging treatment options for preventive and acute attack therapy," Expert Opinion on emerging drugs 11(3):419-427, Sep. 2006, 9 pages.
Goadsby, "New directions in migraine research," Journal of Clinical Neuroscience 9:116, Jul. 2002, 6 pages.
Goadsby, "New targets in the acute treatment of headache," Curr Opin Neurol 18(3):283-288, Jun. 2005, 6 pages.
Goadsby, "Pathophysiology of cluster headache: a trigeminal autonomic cephalgia," Lancet Neurology 1:251-257, 2002, 7 pages.
Goadsby, "Pathophysiology of Migraine", Neurol Clin 27:335-360, May 2009, 6 pages.
Goadsby, "Post-triptan Era for the Treatment of Acute Migraine," Current Pain and Headache Reports 8(5):393-398, Oct. 2004, 6 pages.
Goadsby, "Recent advances in the diagnosis and management of migraine," BMJ 332:25-29, Jan. 7, 2006, 5 pages.
Goadsby, "Recent advances in understanding migraine mechanisms, molecules and therapeutics," Trends in Molecular Medicine 13(1):39-44, Jan. 2007, 6 pages.
Goadsby, "The vascular theory of migraine—a great story wrecked by the facts," Brain: A Journal of Neurology, 132:6-7, Jan. 2009, 2 pages.
Goadsby, "Trigeminal autonomic cephalalgias (TACs)", Acta Neurologica Belgica 101:10-19, Mar. 2001, 10 pages.
Goadsby, Silberstein, Dodick, "Chronic Daily Headache for Clinicians," Chapters 1-6, 11, 18, Jul. 2005, 112 pages.
Goldstein et al., "Ineffectiveness of neurokinin-1 antagonist in acute migraine: a crossover study," Cephalagia, Nov. 1997, 11 pages.
Goldstein et al., "Lanepitant, an NK-1 antagonist, in migraine prevention," Cephalalgia vol. 21, Mar. 2001, 5 pages.
Goldstein et al., "Selective seratonin 1F (5-HT1F) receptor agonist LY334370 for acute migraine a randomised controlled trial," Lancet vol. 358, Oct. 13, 2001, 5 pages.
Goldstein et al., "Biological Efficacy of a Chimeric Antibody to the Epidermal Growth Factor Receptor in a Human Tumor Xenograft Model," Clinical Cancer Research, vol. 1: 1311-1318, Nov. 1995, 9 pages.
Goyal and Hirano, "The enteric nervous system," Mechanism of Disease, Review Article, The New England Journal of Medicine 334(17):1106-1115, Apr. 25, 1996, 10 pages.
Graham et al., "Mechanism of migraine headache and action of ergotamine tartrate," Arch NeurPhsych, vol. 39 Issue 4, Apr. 1938, 27 pages.
Green et al., U.S. Appl. No. 60/753,004, filed Dec. 22, 2005, 18 pages.
Grennan and Jayson, "Rheumatoid arthiritis," Textbook of Pain pp. 397-407, 1994, 15 pages.
Gupta et al., "Antibodies against G-protein coupled receptors: novel uses in screening and drug development," Comb Chem High Throughput Screen 11(6): 463-467, Jul. 2008, 9 pages.
Gupta et al., "Improvement of the closed cranial window model in rats by intracarotid infusion of signalling molecules implicated in migraine," Cephalalgia 30(1):27-36, Apr. 28, 2009, 10 pages.

Gupta et al., "Intravital microscopy on a closed cranial window in mice: a model to study trigeminovascular mechanisms involved in migraine," Cephalalgia 26:1294-12303, Nov. 2006, 10 pages.
Guyer et al., "Immunoglobulin binding by mouse intestinal epithelial cell receptors," J Immunol 117(2):587-593, Aug. 1976, 8 pages.
Haan et al., "Lisinopril heeft geen relevant preventief effect bij migraine," Ned Tijdsch Geneeskd, vol. 15, 755, 2001, 3 pages.
Hakala et al., "Modelling constrained calcitonin gene-related peptide analogues," Protein Eng 9(2):143-148, Feb. 1996, 6 pages.
Hamann and Berger, "Chapter 12: Mylotarg—The First Antibody-Targeted Chemotherapy Agent," in: Pagé M. (eds) Tumor Targeting in Cancer Therapy. Cancer Drug Discovery and Development. Humana Press, Totowa, NJ. 2002, 16 pages.
Hargreaves and Shepheard, "Pathophysiology of Migraine—New Insights," Can. J. Neurol. Sci 26(3): S12-S19, Nov. 1999, 8 pages.
Hargreaves, "New Migraine and Pain Research," American Headache Society 47(Suppl 1):S26-S43, Apr. 2007, 18 pages.
Harlow, "Using Antibodies: A Laboratory Manual," Chapters 1, 2, 11, Cold Spring Harbor Laboratory Press, 1999, 64 pages.
Hasbak et al., "Investigation of GCRP Receptors and Peptide Pharmacology in Human Coronary Arteries: Characterization with a Nonpeptide Antagonist," the Journal of Pharmacology and Experimental Therapeutics, vol. 304: 326-33, Jan. 2003, 9 pages.
Hay et al., "A comparison of the actions of BIBN4096BS and $CGRP_{8-37}$ on CGRP and adrenomedullin receptors expressed on SK-N-MC, L6, col. 29 and Rat 2 cells," Brit J Pharmacol 137(1):80-86, Sep. 2002, 7 pages.
Hay et al., "CGRP modulation by RAMPS," Pharmacology and Therapeutics 109:173-197, 2006, 25 pages.
Hay et al., "Determinants of 1-Piperidinecarboxamide, N-[2-[[5-Amino-1-[[4-(4-pyridinyl)-1-piperazinyl]carbonyl]pentyl]amino]-1-[(3,5-dibromo-4-hydroxyphenyl)methyl]-2-oxoethyl]-4-(1,4-dihydro-2-oxo-3(2H)-quinazolinyl) (BIBN4096BS) Affinity for Calcitonin Gene-Related Peptide and Amylin Receptors—The Role of Receptor Activity Modifying Protein 1," Mol Pharmacol 70(6):1984-1991, Dec. 2006, 8 pages.
Hay et al., "International Union of Pharmacology. LXIX. Status of the Calcitonin Gene-Related Peptide Subtype 2 Receptor," Pharmacological Reviews 60(2):143-145, 2008, 3 pages.
Hay et al., "Pharmacological Discrimination of Calcitonin Receptor: Receptor Activity-Modifying Protein Complexes," Mol Pharmacol 67(5):1655-1665, May 2005, 11 pages.
Haydon and Carmignoto, "Astrocyte Control of Synaptic Transmission and Neurovascular Coupling," Physiological Reviews 86(3):1009-1031, Jul. 2006, 23 pages.
Haywood et al., "Vasculature of the normal and arthritic synovial joint," Histology and Histopathology, Cellular Molecular Biology, vol. 16: 277-284, Jan. 2001, 8 pages.
Hefti et al., "Abstract 778: RN624 (Anti-NGF) reduces pain and improves function in subjects with moderate to severe pain from osteoarthritis of the knee," J Pain, Apr. 2006, 7(4): Supplement S45.
Hepp et al., "Systematic Review of Migraine Prophylaxis Adherence and Persistence", Journal of Managed Care Pharmacy 20(1):22-33, Jan. 2004, 12 pages.
Herceptin® (trastuzumab) Prescribing Information, Genentech Inc, Sep. 1998, 2 pages.
Hershey et al., "Investigation of the species selectivity of a nonpeptide CGRP receptor antagonist using a novel pharmacodynamic assay," Regulatory Peptides 127(1):71-77, Apr. 2005, 7 pages.
Herzenberg et al., "Chapter 12: Antibody-Antigen Binding: Structure-Function Relationships Viewed at Atomic Scale Resolution," in Weir's Handbook of Experimental Immunology—vol. I: Immunochemistry and Molecular Immunology, 2007, 49 pages.
Herzenberg et al., "Weir's Handbook of Experimental Immunology—vol. IV: The Integrated Immune System," 1997, 121 pages.
Hilairet et al., "Protein-protein Interaction and not Glycosylation Determines the Binding Selectivity of Heterodimers between the Calcitonin Receptor-like Receptor and the Receptor Activity-modifying Proteins," Journal of Biological Chemistry, Aug. 2001, 8 pages.
Hill and Oliver, "Neuropeptide and Kinin Antagonists," HEP 177: 181-216, 2006, 36 pages.

(56) References Cited

OTHER PUBLICATIONS

Hill, "New Targets for Analgesic Drugs," Chapter 36, proceedings of the 10th World Congress on Pain, Progress in Pain Research and Management 24: 419-436, 2003, 18 pages.
Hill, "$NK_1$ (substance P) receptor antagonists—why are they not analgesic in humans?," TiPS 21:244-246, Jul. 2000, 3 pages.
Hinton et al., "An Engineered human IgG1 Antibody with Longer Serum Half-Life," The Journal of Immunology, Jan. 2006, 11 pages.
Ho et al., "Efficacy and tolerability of MK-0974 (telcagepant), a new oral antagonist of calcitonin gene-related receptor, compared with zolmitriptan for acute migraine: a randomised, placebo-controlled, parallel-treatment trial," Lancet vol. 372: 2115-2123, Dec. 2008, 9 pages.
Hoare, Mechanisms of peptide and nonpeptide ligand binding to Class B G-protein-coupled receptors, Drug Discovery Today 10(6):417-427, Mar. 2005, 11 pages.
Hoff et al., "A breathtaking headache," Journal of Neurology and Neurosurgery Psychiatry, vol. 75: 506-509, Apr. 2004, 6 pages.
Hogue et al., "Pathophysiology and first-line treatment of osteoarthritis," Ann Pharmacother 36(4):679-686, Apr. 2002, 8 pages.
Holm et al., "Functional mapping and single chain construction of the anti-cytokeratin 8 monoclonal antibody TS1," Mol Immunol 44(6):1075-1084, Feb. 2007, 10 pages.
Holman et al., "Human alpha- and beta-CGRP and rat alpha-CGRP are coronary vasodilators in the rat," Peptides 7(2):231-235, Mar.-Apr. 1986, 5 pages.
Holt et al., "Anti-serum albumin domain antibodies for extending the half-lives of short lived drugs," Protein Engineering, Design and Selection, vol. 21(5): 283-288, May 2008, 6 pages.
Holt et al., "Domain antibodies: proteins for therapy," Trends Biotechnol 21(11):484-490, Nov. 2003, 7 pages.
Hong et al., "Pharmacological coupling and functional role for CGRP receptors in the vasodilation of rat pial arterioles," Am J Phsyiol 270(1):H317-H323, Jan. 1, 1996, 6 pages.
Hong et al., "Pharmacological evidence that calcitonin gene-related peptide is implicated in cerebral autoregulation," Am J Physiology—Heart Circ Physiol 266(1):H11-H16, 1994, 6 pages.
Honore et al., "Murine models of inflammatory, neuropathic and cancer pain each generates a unique set of neurochemical changes in the spinal cord and sensory neurons," Neuroscience 98(3):585-598, 2000, 14 pages.
Hoogenboom and Winter, "By-passing immunisation. Human antibodies from synthetic repertoires of germline VH gene segments rearranged in vitro," J Mol Biol 227(2):381-388, Sep. 20, 1992, 8 pages.
Hopkins, "The druggable genome," Nature Reviews: Drug Discovery, Nature Publishing Group, vol. 1, Sep. 2002, 4 pages.
Hruby, "Designing Peptide Receptor Agonists and Antagonists," Nat Rev Drug Discov 1:835-858, Nov. 2002, 14 pages.
Hu et al., "A new view of Starling's hypothesis at the microstructural level," Microvascular Research Vo. 58:281-304, Nov. 1999, 24 pages.
Hubbard et al., "Identification of the epitopes of calcitonin gene-related peptide (CGRP) for two anti-CGRP monoclonal antibodies by 2D NMR," Protein Science 6: 1945-1952, Sep. 1997, 8 pages.
Huls et al., "Antitumor Immune Effector Mechanisms Recruited by Phage Display-derived Fully Human IgG1 and IgA1 Monoclonal Antibodies," Cancer Research vol. 59, Nov. 15, 1999, 8 pages.
Humphrey et al., "Chapter 32: Consistency of pain relief over multiple migraine attacks following treatment with rizatriptan & Chapter 40: Clinical efficacy and tolerability of the triptans—discussion summary," in The Triptans—Novel Drugs for Migraine, Oxford University Press, 2001, 12 pages.
Humphrey et al., "Preclinical Studies on the Anti-Migraine Drug, Sumatriptan," Eur. Neurol., vol. 31, No. 5, pp. 282-290, 1991, 9 pages.
Humphrey et al., "Serotonin and Migraine," Annals N.Y. Acad. Science, vol. 600, Issue 1, pp. 587-600, Oct. 1990, 14 pages.
Humphrey et al., "GR43175, a selective agonist for the 5-HT1-like receptor in dog isolated saphenous vein," Br. J. Pharmacol. 94, 1123-1132, Aug. 1988, 10 pages.
Huston et al., "Protein engineering of antibody binding sites: recovery of specific activity in an anti-digoxin single-chain Fv analogue produced in *Escherichia coli*," Proc Natl Acad Sci USA 85(16):5879-5883, Aug. 1988, 5 pages.
Idusogie et al., "Mapping of the C1q binding site on rituxan, a chimeric antibody with a human IgG1 Fc," J Immunol 15;164(8):4178-84, Apr. 15, 2000.
International Classification of Diseases and Related Health Problems: Version for 2005 (ICD), 10 pages.
International Classification of Diseases and Related Health Problems: Version for 2006 (ICD), 10 pages.
International Preliminary Report on Patentability in Application No. PCT/IB2006/003181, dated May 14, 2008, 9 pages.
International Search Report and Written Opinion in Application No. PCT/IB2006/003181, dated May 9, 2007, 14 pages.
International Search Report and Written Opinion in Application No. PCT/IB2009/050849, dated Jul. 31, 2009, 6 pages.
International Search Report and Written Opinion in Application No. PCT/IB2009/050852, dated Jul. 29, 2009, 12 pages.
Iovino et al., "Safety, Tolerability and Pharmacokinetics of BIBN 4096 BS, the First Selective Small Molecule Calcitonin Gene-Related Peptide Receptor Antagonist, Following Single Intravenous Administration in Healthy Volunteers," Cephalalgia, 24: 645-656, Aug. 2004, 12 pages.
Irie et al., "Phase I pilot clinical trial for human IgM monoclonal antibody to ganglioside GM3 in patients with metastatic melanoma," Cancer Immunol. Immunother vol. 53, Feb. 2004, 8 pages.
Janeway and Travers, "Immunobiology: The Immune System in Health and Disease, Second Edition," Chapter 2, 3 and 12, Current Biology Ltd./Garland Publishing Inc., 1996, 134 pages.
Janeway and Travers, Immunobiology: The Immune System in Health and Disease, Garland Publishing. p. G-2, 1994, 3 pages.
Janeway et al., "Immunobiology, 5th Edition: The Immune Systems in Health and Disease," pp. 123-154, Garland Publishing, Taylor and Francis Group, 2001, 35 pages.
Janeway et al., "Immunobiology, 5th Edition: The Immune Systems in Health and Disease," pp. 341-380, Garland Publishing, Taylor and Francis Group, 2001, 44 pages.
Janeway et al., "Immunobiology, 5th Edition: The Immune Systems in Health and Disease," pp. 626-627, Garland Publishing, Taylor and Francis Group, 2001, 5 pages.
Janeway et al., "Immunobiology, 5th Edition: The Immune Systems in Health and Disease," pp. 93-122 Garland Publishing, Taylor and Francis Group, 2001, 34 pages.
Jang et al., "The structural basis for DNA binding by an anti-DNA autoantibody," Mol Immunol 35(18):1207-1217, Dec. 1998, 11 pages.
Jefferis, "Antibody terapeutics: isotype and glycoform selection," Expert Opinion Biol Ther, vol. 7, No. 9, 1401-1413, Sep. 2007, 13 pages.
Jefferis, "Glycosylation of recombinant antibody therapeutics," Biotechnology Progress, American Institute of Chemical Engineers 21(1):11-16, Jan. 1, 2005, 6 pages.
Jefferis, "The antibody paradigm: present and future development as a scaffold for biopharmaceutical drugs", Biotechnology and Genetic Engineering Reviews 26:1-42, Jul. 2009, 43 pages.
Jhee, "Pharmacokinetics and pharmacodynamics of the triptan antimigraine agents: a comparative review," Drug Disposition, Pharmacokinet, vol. 40, Issue 3, Feb. 2001, 17 pages.
Johnstone et al., "The Effect of Temperature on the Binding Kinetics and Equilibrium Constants of Monoclonal Antibodies to Cell Surface Antigens," Molecular Immunology, vol. 27, No. 4, Apr. 1990, 7 pages.
Jones et al., "Replacing the Complementarity-Determining Regions in a Human Antibody with Those from a Mouse," Nature vol. 321, May 29, 1986, 4 pages.
Juhasz et al., "NO-induced migraine attack: strong increase in plasma calcitonin gene-related peptide (CGRP) concentration and negative correlation with platelet serotonin release," Pain 106(3):461-470, Dec. 2003, 10 pages.

(56) References Cited

OTHER PUBLICATIONS

Juhl et al., "Effect of two novel CGRP-binding compounds in a closed cranial window rat model," Europ J Pharmacol 657(1-2):117-124, Jul. 12, 2007, 8 pages.
Julia and Bueno, "Tachykininergic mediation of viscerosensitive responses to acute inflammation in rats: role of CGRP," Am J Physiol 272(1 Pt 1):G141-G146, Jan. 1997, 6 pages.
Kajekar et al., "Effect of a 5-HT1 receptor agonist, CP-122,288, on oedema formation induced by stimulation of the rat saphenous nerve," British Journal of Pharmacology 115(1):1-2, May 1995, 2 pages.
Kaneko, et al. [Visceral hypersensitivity]. Nihon Rinsho, vol. 64, No. 8:1446-51, Aug. 2006, (in Japanese), 8 pages.
Kar et al., "Increased calcitonin gene-related peptide (CGRP), substance P, and EYKephalin immunoreactivities in dorsal spinal cord and loss of CGRP-immunoreactive motoneurons in arthritic rats depend on intact peripheral nerve supply," J Mol Neurosci 3(1):7-18, 1991, 12 pages.
Katz et al., "Measurement of pain," Surg Clin North Am 79(2):231-252, Apr. 1999, 12 pages.
Kaube et al., "Inhibition by sumatriptan of central trigeminal neurons only after blood-brain barrier disruption," British Journal of Pharmacology 109 788-792, Jul. 1993, 5 pages.
Kawamura et al., "Antinociceptive effect of intrathecally administered antiserum against calcitonin gene-related peptide on thermal and mechanical noxious stimuli in experimental hyperalgesic rats," Brain Res 497(1):199-203, Sep. 11, 1989, 5 pages.
Keller et al., "Lack of Efficacy of the Substance P (Neurokinin) Receptor) Antagonist Aprepitant in the Treatment of Major Depressive Disorder," Biological Psychiatry 59(3):216-223, Feb. 2005, 8 pages.
Kelley, "Thermodynamics of Protein-Protein Interaction Studied by Using BIAcore and Single-Site Mutagenesis," Methods: A companion to methods in Enzymology, vol. 6, Issue 2, 111-120, Jun. 1994, 10 pages.
Kenakin and Onaran, "The ligand paradox between affinity and efficacy: can you be there and not make a difference?" TRENDS in Pharmaceutical Sciences 23(6): 275-280, Jun. 2002, 6 pages.
Kenakin, "Drug Efficacy at G Protein-Coupled Receptors," Annu Rev Pharmacol Toxicol 42: 349-379, 2002, 33 pages.
Kenakin, "Efficacy of G-protein-coupled receptors," Nature Reviews, Drug Discovery, vol. 1, Macmillan Magazines, Feb. 2002, 8 pages.
Kenakin, "G-Protein Coupled Receptors as Allosteric Machines," Receptors and Channels 10: 51-60, 2004, 10 pages.
Kenakin, "Principles: Receptor Theory in Pharmacology," TRENDS in Pharmacological Sciences 25(4) 186-224, Apr. 2004, 7 pages.
Kenney et al., "Influence of adjuvants on the quantity, affinity, isotype and epitope specificity of murine antibodies," Journal of Immunological Methods, 121, 157-166, Jul. 1989, 10 pages.
Kernick et al., "Cluster headache in primary care: unmissable, underdiagnosed and undertreated," British Journal of General Practice, 56(528):486-487, Jul. 2006, 2 pages.
Kettleborough et al., "Humanization of a Mouse Monoclonal Antibody by CDR-Grafting: The Importance of Framework Residues on Loop Conformation," Protein Engineering, vol. 4, No. 7, Oct. 1991, 11 pages.
Khazaeli et al., "Human Immune Response to Monoclonal Antibodies," Journal of Immunotherapy, 15: 42-52, Jan. 1994, 11 pages.
Kim et al., "Antibody Engineering for the Development of Therapeutic Antibodies," Molecules and Cells, vol. 20, No. 1, Aug. 2005, 13 pages.
Kipriyanov and Le Gall, "Generation and Production of Engineered Antibodies," Molecular Biotechnology, vol. 26, Jan. 2004, 22 pages.
Kipriyanov, "Generation of antibody molecules through antibody engineering," Methods Mol Biol 207:3-25, 2003, 23 pages.
Knauf et al., "Relationship of effective molecular size to systemic clearence in rats of recombinant interleukin-2 chemical modified with water-soluable polymers," The Journal of Biological Chemistry, vol. 263, No. 29, Issue of Oct. 15, 1988, 7 pages.

Knight et al., "4991W93 inhibits release of calcitonin gene-related peptide in the cat but only at doses with 5HT1B/1D receptor agonist activity," Neuropharmacology 40:520-525, Mar. 2001, 6 pages.
Knight et al., "Pharmacodynamic Enhancement of the Anti-Platelet Antibody Fab Abciximab by Site-Specific Pegylation," Platelets 15(7), Nov. 2004, 11 pages.
Knudsen et al., "Chapter 5: Morphology, Physiology and Pathophysiology of the brain barrier," in Basic Mechanisms of Migraine, 1988.
Kobayashi et al., "Tryptophan H33 plays an important role in pyrimidine (6-4) pyrimidone photoproduct binding by a high-affinity antibody," Protein Eng 12(10):879-884, Oct. 1999, 6 pages.
Kohler and Milstein, "Continuous cultures of fused cells secreting antibody of predefined specificity," Nature 256(5517):495-497, Aug. 7, 1975, 3 pages.
Kosek and Ordeberg, "Lack of pressure pain modulation by heterotopic noxious conditioning stimulation in patients with painful osteoarthritis before, but not following, surgical pain relief," Pain, 2000, 88: 69-78.
Kraljevic et al., "Accelerating drug discovery," European Molecular Biology Organization (EMBO) reports, 5(9): 837-842, Sep. 2004, 6 pages.
Krogsgaard-Larsen et al., "Textbook of Drug Design and Discovery," p. 7-8, Taylor and Francis, 2002, 4 pages.
Kruit et al., "Brain stem and cerebellar hyperintense lesions in migraine," Stroke 37:1109-1112, Feb. 2006, 4 pages.
Kruit et al., "Iron accumulation in deep brain nuclei in migraine: a population-based magnetic resonance imaging study," Cephalalgia 29:351-359, Mar. 2009, 14 pages.
Kruit et al., "Migraine as a Risk Factor for Subclinical Brain Lesions," JAMA vol. 291: 427-434, Jan. 28, 2004, 8 pages.
Kruit et al., "Migraine as a risk factor for white matter lesions, silent infarctions, and ischemic stroke: the evidence for a link," Headache Currents, vol. 2, No. 3:62-71, Jun. 2005, 9 pages.
Kruit et al., "MRI findings in migraine," Revue Neurologique 161,6/7:661-666, 2005, 5 pages.
Kruuse et al., "Plasma levels of cAMP, cGMP and CGRP in sildenafil-induced headache," Cephalalgia 24(7):547-553, Jul. 2004, 7 pages.
Kumar et al., "Molecular cloning and expression of the Fabs of human autoantibodies in *Escherichia coli*. Determination of the heavy or light chain contribution to the anti-DNA/-cardiolipin activity of the Fab," J Biol Chem 275(45):35129-35136, Nov. 10, 2000, 8 pages.
Kuraishi et al., "Antinociception induced in rats by intrathecal administration of antiserum against calcitonin gene-related peptide," Neurosci Lett 92(3):325-329, Oct. 17, 1988, 5 pages.
Kurosawa et al., "Increase of meningeal blood flow after electrical stimulation of rat dura mater encephali: mediation by calcitonin gene-related peptide," British Journal of Pharmacology 114:1397-1402, Apr. 1995, 6 pages.
Kurth et al., "Migraine and Rish of Cardiovascular Disease in Women," JAMA vol. 296(3), Jul. 19, 2006, 10 pages.
Kussie, "A single engineered amino acid substitution changes antibody fine specificity", J Immunol 152(1):146-152, Jan. 1994, 7 pages.
Lassen et al., "CGRP may play a causative role in migraine," Cephalalgia 22(1):54-61, Feb. 2002, 8 pages.
Lassen et al., "Comorbidity," Poster Presentations, Cephalagia 23:581-762, 2003, 1 page.
Lassen et al., "Involvement of calcitonin gene-related peptide in migraine: regional cerebral blood flow and blood flow velocity in migraine patients," J Headache Pain 9(3):151-157, Jun. 2008, 7 pages.
Lassen et al., "Nitric oxide synthase inhibition in migraine," Lancet, vol. 349, Feb. 1997, 2 pages.
Laukkanen et al., "Hevein-specific recombinant IgE from human single-chain antibody phage display libraries," Journal of Immunological Methods, vol. 278:271-281, Jul. 2003, 11 pages.
Launer et al., "The prevalence and characteristics of migraine in a population-based cohort, the GEM study," Neurology vol. 53: 537-542, Aug. 1999, 17 pages.
Lauritzen, "Pathophysiology of the migraine aura: The spreading depression theory," Oxford University Press, Feb. 1994, 12 pages.

(56) References Cited

OTHER PUBLICATIONS

Léger et al., "Humanization of a Mouse Antibody against Human Alpha-4 Integrin: A Potential Therapeutic for the Treatment of Multiple Sclerosis," Human Antibodies vol. 8: 3-16, Mar. 1, 1997, 14 pages.
Lenzer et al., "FDA advisers warn: COX2 inhibitors increase risk of heart attack and stroke," BMJ, vol. 330, Feb. 26, 2005, 1 page.
Levine and Taiwo, "Inflammatory pain," Textbook of Pain, pp. 45-56, 1994, 17 pages.
Levy et al., "Calcitonin Gene-Related Peptide Does Not Excite or Sensitize Meningeal Nociceptors: Implications for the Pathophysiology of Migraine," Annal Neurol 58(5):698-705, Nov. 2005, 8 pages.
Levy et al., "Disruption of communication between peripheral and central trigeminovascular neurons mediates the antimigraine action of 5HT1B/1D receptor agonists," PNAS 101(12):4274-4279, Mar. 23, 2004, 6 pages.
Levy et al., "Octreotide is not effective in the acute treatment of migraine," Cephalalgia 25:48-55, Jan. 2005, 8 pages.
Li and Schwartz, "The TNFa transgenic mouse model of inflammatory arthritis," Springer Seminars in Immunopathology, Aug. 2003, 15 pages.
Li et al., "Calcitonin gene-related peptide stimulation of nitric oxide synthesis and release from trigeminal ganglion glial cells," Brain Res 1196:22-32, Feb. 27, 2008.
Lin et al., "Preclinical pharmacokinetics, interspecies scaling and tissue distribution of a humanized monoclonal antibody against vascular endothelial growth factor," Journal of Pharmacology and Experimental Therapeutics, 288:371-378, Jan. 1999, 8 pages.
Lipinski et al., "Experimental and computational appraoches to estimate solubility and permeability in drug discovery and development settings," Advanced Drug Delivery Reviews, vol. 23: 3-25, Jan. 1997, 24 pages.
Lipton and Stewart, "Acute migraine therapy: do doctors understand what patients with migraine want from therapy," Headache vol. 39, Suppl. 2: S20-S26, Aug. 1999, 7 pages.
Lipton et al., "Classification of primary headaches," Journal of Neurology, vol. 63, Views and Reviews, Aug. 2004, 9 pages.
Lipton et al., "Double-blind clinical trials of oral triptans versus other classes of acute migraine medication," Cephalalgia 24:321-332, May 2004, 12 pages.
Lipton et al., "How treatment priorities influence triptan preferences in clinical practice: perspectives of migraine sufferers, neurologists, and primary care physicians," Current Medical Research and Opinion 21:413-424, Mar. 2005, 12 pages.
Lipton et al., "Migraine practice patterns among neurologists," Neurology, Jun. 2004, 7 pages.
Lipton et al., "Migraine prevalence, disease burden, and the need for preventive therapy", Neurology. 68(5):343-9, Jan. 30, 2007, 8 pages.
Lipton et al., "Migraine. Identifying and removing barriers to care," Neurology vol. 44, Suppl. 4, S63-S68, Jun. 1994, 6 pages.
Lipton et al., "Moving Forward—Essential Questions for the Next 10 Years," Headache 49:S43-S46, Feb. 2009, 4 pages.
Lipton et al., "The role of headache-related disability in migraine management," Neurology 56(Supp 1):535-542, 2001, 8 pages.
Lipton et al., "Treatment preferences and the selection of acute migraine medications: results from a population-based survey," Journal of Headache Pain, vol. 5, Issue 2, Aug. 2004, 8 pages.
Lipton et al., "Why headache treatment fails?" Neurology 60:1064-1070, Apr. 2003, 7 pages.
Lipton, "CGRP antagonists in the acute treatment of migraine", The Lancet Neurology 3:332, Jun. 2004, 1 page.
Little and Smith, "Animal Models of Osteoarthritis," Current Rheumatology Reviews, 2008, 4.
Little et al., "Of mice and men: hybridoma and recombinant antibodies," Immunol Today 21(8):364-370, Aug. 2000, 7 pages.
Lodish et al., "Molecular Cell Biology," 5th Edition, W.H. Freeman and Company, pp. 537-539, 2004, 4 pages.
Longmore et al., "5-HT1D receptor agonists and human coronary artery reactivity in vitro crossover comparisons of 5-HT and sumatriptan with rizatriptan and L-741,519," Br J Clin Pharmacol 42:431-441, 1996, 11 pages.
Longmore et al., "Comparison of the vasoconstrictor effects of the selective 5-HT1D-receptor agonist L-775,606 with the mixed 5-HT1B/1D-receptor agonist sumatriptan and 5-HT in human isolated coronary artery," J Clin Pharmacol 49:126-131, 2000, 6 pages.
Longmore et al., "Effects of two truncated forms of human calcitonin-gene related peptide: implications for receptor classification," European Journal of Pharmacology 265:53-59, Nov. 1994, 7 pages.
Longstreth et al., "Functional bowel disorders," Gastroenterology 130(5):1480-1491, Apr. 2006, 15 pages.
Louis et al., "Antibodies to calcitonin-gene related peptide reduce inflammation induced by topical mustard oil but not that due to carrageenin in the rat," Neurosci Lett 102(2-3):257-260, Jul. 31, 1989, 4 pages.
Louis et al "Immunization with Calcitonin Gene-Related Peptide Reduces the Inflammatory Response to Adjuvant Arthritis in the Rat," Neuroscience, 1990, 39(3): 727-731.
Louis et al., "The role of substance P and calcitonin gene-related peptide in neurogenic plasma extravasation and vasodilatation in the rat," Neuroscience 32(3):581-586, 1989, 6 pages.
Luykx et al., "Are migraineurs at increased risk of adverse drug responses?: A meta-analytic comparison of topiramate-related adverse drug reactions in epilepsy and migraine," Clinical Pharmacology & Therapeutics, vol. 85, No. 3, Mar. 2009, 6 pages.
Ma et al., "Colocalization of CGRP with 5-HT 1B/1D receptors and substance P in trigeminal ganglion neurons in rats," European Journal of Neuroscience 13:2099-2104, Jun. 2001, 6 pages.
MaassenVanDenBrink et al., "5-HT1B-receptor polymorphism and clinical response to sumatriptan," Headache, vol. 38:288-91, Apr. 1998, 4 pages.
MaassenVanDenBrink et al., "Augmented contraction of the human isolated coronary artery by sumatriptan: a possile role for endogenous thromboxane," British Journal of Pharmacology, vol. 119:855-62, Nov. 1996, 8 pages.
MabCampath® (alemtuzumab), "Scientific Discussion," EMEA 2005, 22 pages.
MacCallum et al., "Antibody-antigen interactions: contact analysis and binding site topography," J Mol Biol 262(5):732-745, Oct. 11, 1996, 14 pages.
MacEwan, "TNF receptor subtype signaling differences and cellular consequences," Cell Signal vol. 14, 477-492, Jun. 2002, 16 pages.
Maini and Feldmann, "How Does Infliximab Work in Rheumatoid Arthritis?" Arthritis Research, vol. 4, Suppl. 2, Mar. 27, 2002, 7 pages.
Malik et al., "Research Submission—Acute migraine treatment: patterns of use and satisfaction in clinical population," Headache, May 2006, 8 pages.
Mallee et al., "Receptor activity-modifying protein 1 determines the species selectivity of nonpeptide CGRP receptor antagonists," J Biol Chem 277(16):14294-14298, Apr. 19, 2002, 8 pages.
Manack et al., "The Evolution of Chronic Migraine: Classification and Nomenclature", Headache 49:1206-1213, Sep. 2009, 8 pages.
Mankarious et al., "The half-lives of IgG subclasses and specific antibodies in patients with primary immunodeficiency who are receiving intravenously administered immunoglobulin," J Lab of Clinical Medicine, vol. 112, No. 5, Nov. 1988, 7 pages.
Mantyh et al., "Molecular Mechanisms of Chronic Pain," Nature Reviews: Cancer, Mar. 2002, 2: 201-209.
Marks et al., "By-passing immunization Human antibodies from V-gene libraries displayed on phage," J Mol Biol 222(3):581-597, Dec. 5, 1991, 17 pages.
Marks et al., "By-passing immunization: building high affinity human antibodies by chain shuffling," Biotechnol 10(7):779-783, Jul. 1992, 17 pages.
Marquez de Prado and Russo, "CGRP receptor antagonists: A new frontier of anti-migraine medications," Drug Discov Today Ther Strateg 3(4):593-597, 2006, 8 pages.
Marshall et al., "Human and rat alpha-CGRP but not calcitonin cause mesenteric vasodilatation in rats," Eur J Pharmacol 123(2):217-222, Apr. 16, 1986, 6 pages.

(56) References Cited

OTHER PUBLICATIONS

Martinelletti et al., "The Global Campaign (GC) to reduce the burden of headache worldwide: The international team for specialist education (ITSE)," Journal of Headache Pain, vol. 6(4), Jul. 20, 2005, 3 pages.
Mason et al., "Release of the Predicted Calcitonin Gene-Related Peptide from Cultured Rat Trigeminal Ganglion Cells," Nature vol. 308: 653-655, Apr. 1984, 3 pages.
Matharu and Goadsby, "Trigeminal autonomic cephalalgias," J Neurol Neurosurf Psychiatry 72)Suppl II):ii19-ii26, 2002, 8 pages.
Matharu et al., "Verapamil-induced gingival enlargement in cluster headache," Journal of Neurology, Neruosurgery, and Psychiatry 76:124-127, Jan. 2005, 4 pages.
May et al., "EFNS guidelines on the treatment of cluster headache and other trigeminalautonomic cephalalgias," European Journal of Neurology 13:1066-1077, Oct. 2006, 12 pages.
May et al., "PET and MRA findings in cluster headache and MRA in experimental pain," Neurology 55:1328-1335, Nov. 2000, 8 pages.
May, "Cluster headache: pathogenesis, diagnosis, and management," Lancet 366:843-855, 2005, 13 pages.
Maynard and Georgiou, "Antibody Engineering," Annu. Rev. Biomed. Eng. 2: 339-376, 2000, 38 pages.
McCafferty et al., "Phage antibodies: filamentous phage displaying antibody variable domains," Nature 348(6301):552-554, Dec. 6, 1990, 3 pages.
McCarthy et al., "Osteoarthritis," Textbook of Pain, pp. 387-395, 1994, 15 pages.
McCulloch et al., "Calcitonin gene-related peptide: Functional role in cerebrovascular regulation," Proc Natl Acad Sci USA 83:5731-5735, Aug. 1986, 5 pages.
McDougall, "Review: Arthritis and pain: Neurogenic origin of joint pain," Arthritis Research & Therapy vol. 8:220, Nov. 10, 2006, 10 pages.
McLatchie et al., "RAMPs regulate the transport and ligand specificity of the calcitoninreceptor-like receptor," Nature 393(6683):333-339, May 28, 1998, 7 pages.
Medhurst et al., "A rat model of bone cancer pain," Pain 96(1-2):129-140, Mar. 2002, 12 pages.
Meenan et al., "The arthritis impact measurement scales. Further investigations of a health status measure," Arthritis Rheum 25(9):1048-1053, Sep. 1982, 6 pages.
Mense, "Pathophysiology of low back pain and the transition to the chronic state—experimental data and new concepts," Schmerz 15(6):413-417, Dec. 2001, Article in German, 5 pages.
Merck manual., Pain, 17th Ed. p. 1367, #167. (in Japanese with Engish translation), 1999, 5 pages.
Merskey et al., "Classification of Chronic Pain, Descriptions of Chronic Pain Syndromes and Definitions of Pain Terms," IASP Task Force on Taxonomy 1994. 2nd Edition. 238 pages.
Messlinger et al., "Abstracts of the XII Congress of the International Headache Society/ IHC 2005," Cephalalgia, Believe in Headache Relief, IHC 2005 Kyoto, Oct. 2005, 193 pages.
Messlinger et al., "Inhibition of neurogenic blood flow increases in the rat cranial dura mater by a CGRP-binding Spiegelmer," Cephalalgia 25:923, Oct. 2005, 3 pages.
Messlinger et al., "Poster—Inhibition of neurogenic blood flow increases in the rat cranial dua mater by a CGRP-binding Spiegelmer," Cephalalgia 25:923, Oct. 2005, 1 page.
Mogil et al., "Variable sesitivity to noxious heat is mediated by differential expression of the CGRP gene," PNAS, Sep. 2005, 102(36): 12938-12943.
Morara et al., "Calcitonin Gene-Related Peptide Receptor Exprssion in the Neurons and Glia of Developing Rat Cerebellum: An Autoradiographic and Immunohistochemical Analysis," Neuroscience 100(2):381-391, 2000, 11 pages.
Morell et al., "Metabolic properties of IgG subclasses in man," J Clin Invest 49(4):673-680, Apr. 1970, 8 pages.

Moreno et al., "Efficacy of the non-peptide antagonist BIBN4096BS in blocking CGRP-induced dilations in human and bovine cerebral arteries," Neuropharmacology 42(4):568-576, Mar. 2002, 9 pages.
Morrison et al., "Chimeric human antibody molecules: Mouse antigen-binding domains with human constant region domains," Proceedings of the National Academy of Science, USA, vol. 81(21), Nov. 1984, 5 pages.
Moskowitz, "Interpreting vessel diameter changes in vascular headaches," Cephalalgia, Feb. 1992, 3 pages.
Moskowitz, "Neurogenic versus vascular mechanisms of sumatriptan and ergot alkaloids in migraine", Trends in Pharmacological Sciences 13(8):307-311, Aug. 1992, 5 pages.
Mulderry et al., "Differential expression of alpha-CGRP and beta-CGRP by primary sensory neurons and enteric autonomic neurons of the rat," Neuroscience 25(1):195-205, Apr. 1988, 11 pages.
Mullins et al., "Characterization of a calcitonin gene-related peptide (CGRP) receptor on mouse bone marrow cells," Regul Pept 49(1):65-72, Nov. 19, 1993 (Abstract only), 1 page.
Nakamura-Craig and Gill, "Effect of neurokinin a, substance P and calcitonin gene related peptide in peripheral hyperalgesia in the rat paw," Neurosci Lett 124(1):49-51, Mar. 11, 1991, 3 pages.
Nestorov, "Clinical pharmacokinetics of tumor necrosis factor antagonists," The Journal of Rheumatology 74:13-18, Mar. 2005, 7 pages.
Neugebauer et al., "Calcitonin Gene-Related Peptide is involved in the Spinal Processing of Mechanosensory Input from the Rat's Knee Joint and in the Generation and Maintenance of Hyperexcitability of Dorsal Horn Neurons during Development of Acute Inflammation," Neuroscience, 1996, 71(4): 1095-1109.
Nilsson et al., "Placebo response rates in cluster headache trials, a review," Cephalalgia 23:504-510, Sep. 2003, 7 pages.
Norman et al., "A placebo-controlled, in-clinic study to explore the preliminary safety and efficacy of intravenous L-758,298 (a prodrug of the NK1 receptor antagonist L-754,030) in the acute treatment of migraine," Cephalalgia 18, Poster Presentations, 1998, 1 page.
Nyholt et al., "A high-density association screen of 155 ion transport genes for involvement with common migraine," Human Molecular Genetics, 17: 3318-3331, Nov. 2008, 14 pages.
O'Connell et al., "On the role of the C-terminus of α-calcitonin-gene-related peptide (αCGRP) The Structure of des-phenylalaninamide$^{37}$-αCGRP and it's interatction with the CGRP receptor," Biochem J 291:205-210, 1993, 6 pages.
Odink et al., "F229: Plasma aminoacids in common and classic migraine and tension headache," Neurochemistry Int., 13,suppl. 1:155-56, 1988, 1 pages.
Olesen (and the First Headache Classification Subcommittee Members), "The International Classification of Headache Disorders: 2rd Edition," Blackwell Publishing, 2004, 150 pages.
Olesen and Goadsby, "The Headaches: Third Edition," Chapters 2, 9, 10, 16, 22, 28, 30, 31, 33, 47, 48, 49, 50-60, 2005, 259 pages.
Olesen and Hargreaves, "CGRP Involvement in Migraines," The Headaches, Lippincott Williams & Wilkins, Chapter 31, pp. 289-299, Oct. 1, 2005, 13 pages.
Olesen et al., "Brief Report—New appendix criteria open for a broader concept of chronic migraine," Cephalalgia 26: 742-746, Jun. 2006, 5 pages.
Olesen et al., "Calcitonin gene-related peptide receptor antagonist BIBN 4096 BS for the acute treatment of migraine," N Eng J Med 350(11):1104-1110, Mar. 11, 2004, 7 pages.
Olesen et al., "Origin of pain in migraine: evidence for peripheral sensitisation," Lancet Neruol 8(7):679-690, Jul. 2009, 12 pages.
Olesen et al., "Timing and Topography of Cerebral Blood Flow, Aura, and the Headache during Migraine Attacks," Ann Neurol. vol. 28, No. 6, Dec. 1990, 8 pages.
Olesen et al., "S26 CGRP Antagonism as a New Therapeutic Principle in Acute Migraine," Neuropeptides 38: 110-131, No. 2-3, Apr./Jun. 2004, 6 pages.
Olesen, "Chapter 11: Chronic migraine," in Classification and Diagnosis of Headache Disorders, Oxford University Press 2005, 8 pages.
Olesen, "In-depth characterization of CGRP receptors in human intracranial arteries," European Journal of Pharmacology, vol. 481, Nov. 2003, 10 pages.

(56) References Cited

OTHER PUBLICATIONS

Olesen, "The treatment of acute migraine," Rev Neurol (Paris) 161(6-7):679-680, Jul. 2005, 2 pages.

Oliver et al., "Immunohistochemical Localization of Calcitonin Receptor-Like Receptor and Receptor Activity-Modifying Proteins in the Human Cerebral Vasculature," Journal of Cerebral Blood Flow & Metabolism 22: 620-629, May 2002, 10 pages.

Oliver et al., "Distribution of novel CGRP1 receptor and adrenomedullin receptor mRNAs in the rat central nervous system," Molecular Brain Research 57: 149-154, Jun. 1998, 6 pages.

Oliver et al., "Regional and cellular localization of calcitonin gene-related peptide-receptor component protin mRNA in the guinea-pig central nervous system," Molecular Brain Research 66: 201-210, Mar. 1999, 6 pages.

Ophoff et al., "P/Q-type Ca2+ channel defects in migraine, ataxia and epilepsy," Trends in Pharmacological Sciences vol. 19:121-127, Apr. 1998, 7 pages.

Ophoff et al., "The impact of pharmacogenetics for migraine," European Journal of Pharmacology, vol. 413:1-10, Februrary 2001, 10 pages.

Oshinsky et al., "Episodic dural stimulation in awake rats: a model for recurrent headache," Headache 47(7):1026-1036, Jul.-Aug. 2007, 17 pages.

Overington et al., "How many drug targets are there?" Nature Reviews: Drug Discovery 5(12):993-996, Dec. 2006, 4 pages.

Owen, "Pregabalin: its efficacy, safety and tolerability profile in fibrommyalgia syndrome," Drugs of Today (Barcelona, Spain), vol. 43, No. 12, Dec. 2007, 7 pages.

Pacharinsak et al., "Animal models of cancer pain," Comp Med 58(3):220-233, Jun. 2008, 14 pages.

Parameswaran et al., "Activation of multiple mitogen-activation protein kinases by recombinant calcitonin gene-related peptide receptor," European Journal of Pharmacology, vol. 389(2-3): 125-30, Feb. 2000, 6 pages.

Pardridge, "CNS Drug Design Based on Principles of Blood-Brain Barrier Transport," Journal of Neurochemistry, vol. 70 No. 5, 1781-1792, May 1998, 12 pages.

Pardridge, "The Blood-Brain Barrier: Bottleneck in Brain Drug Development," NeuroRx: The Journal of American Society for Experimental NeuroTherapeutics, vol. 2, Jan. 3-14, 2005, 12 pages.

Park et al., "Alteration of cancer pain-related signals by radiation. proteomic analysis in an animal model with cancer bone invasion," Int J Radiation Oncol Biol Phys 61(5):1523-1534, Apr. 2005, 12 pages.

Parsons et al., "Tonabersat (SB-220453) a novel benzopyran with anticonvulsant properties attenuates trigeminal nerve-induced neurovascular reflexes," British Journal of Pharmacology 132:1549-1557, Apr. 2001, 9 pages.

Paulus et al., "Analysis of improvement in individual rheumatoid arthritis patients treated with disease-modifying antirheumatic drugs, based on the findings in patients treated with placebo. The Cooperative Systematic Studies of Rheumatic Diseases Group," Arthritis Rheum 33(4):477-484, Apr. 1990, 8 pages.

Paus and Winter, "Mapping epitopes and antigenicity by site-directed masking", PNAS 103 (24):9172-9177, Jun. 13, 2006, 6 pages.

Peroutka, "Neurogenic Inflammation and Migraine: Implications for Therapeutics," Mol Interv 5(5):304-311, Oct. 2005, 8 pages.

Peskar et al., "A monoclonal antibody to calcitonin gene-related peptide abolishes capsaicin-induced gastroprotection," Eur J Pharmacol 250(1):201-203, Nov. 30, 1993, 3 pages.

Petersen et al., "BIBN4096BS Antagonizes Human α-calcitonin Gene Related Peptide-induced Headache and Extracerebral Artery Dilatation," Clin Pharmacol Ther 77(3):202-213, Mar. 7, 2005, 12 pages.

Petersen et al., "Effect of hypotension and carbon dioxide changes in an improved genuine closed cranial window rat model," Cephalalgia 25(1):23-29, Jan. 2005, 7 pages.

Petersen et al., "Inhibitory effect of BIBN4096BS on cephalic vasodilatation induced by CGRP or transcranial electrical stimulation in the rat," Brit J Pharmacol 143(6):697-704, Nov. 2004, 8 pages.

Petersen et al., "Presence and function of the calcitonin gene-related peptide receptor on rat pial arteries investigated in vitro and in vivo," Cephalalgia 25(6):424-432, Jun. 2005, 9 pages.

Petersen et al., "The CGRP-antagonist, BIBN4096BS does not affect cerebral or systemic haemodynamics in healthy volunteers," Cephalalgia 25(2):139-147, Feb. 2005, 9 pages.

Petersen et al., "The effect of the nonpeptide CGRP-antagonist, BIBN4096BS on human-alpha CGRP induced headache and hemodynamics in healthy volunteers," Cephalagia 23:725, 2003, 1 page.

Pfizer.com [online], "Pfizer and Lilly receive FDA fast track designation for Tenezumab," Jun. 13, 2017, http://www.pfizer.com/news/press-release/press-release-detail/pfizer_and_lilly-receive_fda_fast_track_designation-for_tanezumab, 4 pages.

Pietrobon, "Migraine: New Molecular Mechanisms," The Neuroscientist 11(4):373-386, Aug. 2005, 14 pages.

Pilgrim, "Methodology of Clinical Trials of Sumatriptan in Migraine and Cluster Headache," European Neurology 31(5):295-299, 1991, 5 pages.

Plourde et al., "Calcitonin gene-related peptide in viscerosensitive response to colorectal distension in rats," Am J Physiol 273(1 Pt 1):G191-G196, Jul. 1997, 7 pages.

Poduslo et al., "Macromolecular permeability across the blood-nerve and blood-brain barriers," PNAS, vol. 91:5705-5709, Jun. 1994, 5 pages.

Pollack, "F.D.A. Approves a Multiple Sclerosis Drug," New York Times, Nov. 24, 2004, 4 pages.

Poyner et al., "CGRP receptors: beyond the CGRP(1)-CGRP(2) subdivision," Trends in Pharmacological Sciences, vol. 22, No. 5, May 2001, 1 page.

Poyner et al., "International Union of Pharmacology. XXXII. The Mammalian Calcitonin Gene-Related Peptides, Adrenomedullin, Amylin, and Calcitonin Receptors," Pharmacological Reviews 54(2):233-246, Jun. 2002, 14 pages.

Poyner et al., "Structural determinants for binding to CGRP receptors expressed by human SK-N-MC and Col 29 cells: studies with chimeric and other peptides," Brit J Pharmacol 124(8):1659-1666, Aug. 1998, 8 pages.

Poyner et al., "The CGRP Family: Calcitonin Gene-Related Peptide (CGRP), Amylin and Adrenomedullin," Molecular Biology Intelligence Unit 10, Chapters 1-7, and 15-16, 2000, 88 pages.

Poyner, "Calcitonin Gene-Related Peptide: Multiple actions, multiple receptors," Pharmacology & Therapeutics 56(1):23-51, Feb. 1992, 29 pages.

Presta, "Selection, Design, and Engineering of Therapeutic Antibodies," Journal of Allergy and Clinical Immunology, vol. 116, Issue 4, 731-736, Oct. 2005, 6 pages.

Prewett et al., "The biologic effects of C225, a chimeric monoclonal antibody to the EGFR, on human prostate carcinoma," J Immunother Emphasis Tumor Immunol 19(6):419-427, Nov. 1996, 9 pages.

Projan et al., "Small Molecules for Small Minds? The Case for Biologic Pharmaceuticals," Expert Opinion Biol. Ther. 4:1345-1350, Aug. 2004, 7 pages.

Purves et al., "Neuroscience: Third Edition," pp. 763-773, Sinauer Associates, Inc., 2004, 14 pages.

Qiao and Grider, "Up-regulation of calcitonin gene-related peptide and receptor tyro side kinase TrkB in rat bladder afferent neurons following TNBS," Experimental Neurology, vol. 204, Apr. 2004, 13 pages.

Queen et al., "A Humanized Antibody that Binds to the Interleukin 2 Receptor," Proceedings of the National Academy of Sciences of the United States of America, vol. 86: 10029-10033, Dec. 1989, 5 pages.

Rader et al., "Chemically Programmed Monoclonal Antibodies for Cancer Therapy: Adaptor Immunotherapy Based on a Covalent Antibody Catalyst," Proc. Natl. Acad. Science. USA, vol. 100, No. 9, pp. 5396-5400, Apr. 29, 2003, 5 pages.

(56) References Cited

OTHER PUBLICATIONS

Ramadan and Buchanan, "New and future migraine therapy," Pharmacology and Therapeutics, 112(1):199-212, Oct. 2006, 14 pages.
Rang, "Pharmacology: 5th Edition," Chapters 2, 3, 9 ,13, 31, Elsevier Science Limited, 2003, 76 pages.
Rapp et al., "Botulinum Toxin Type A Inhibits Cacitonin Gene-Related Peptide Release from Isolated Rat Bladder," Journal of Urology, American Urological Association, vol. 175, No. 1138-1142, Mar. 2006, 5 pages.
Ravetch et al., "Fc receptors," Annu Rev Immunol 9:457-492, 1991, 36 pages.
Ray and Wolff, "Experimental Studies of Headache," Archives of Surgery, vol. 41, No. 4, Oct. 1940, 44 pages.
Reff et al., "Depletion of B Cells in vivo by a Chimeric Mouse Human Monoclonal Antibody to CD20," Blood vol. 83, No. 2, 435-445, Jan. 15, 1994, 12 pages.
Reichert et al., "Monoclonal Antibody Successes in the Clinic," Nature Biotechnology 23(9): 1073-1078, Sep. 2005, 6 pages.
Reinshagen et al., "Calcitonin gene-related peptide mediates the protective effect of sensory nerves in a model of colonic injury," J Pharmacol Exp Ther 286(2):657-661, Aug. 1998, 5 pages.
Remicade (infliximab), "Prescribing Information," 5007 & 5090 Combined (clean copy): FDA Revisions on Dec. 13, 2004, 32 pages.
Reuter et al., "Experimental models of migraine," Funct Neurol 15(53):9-18, 2000, 10 pages.
Rist et al., "CGRP 27-37 analogues with high affinity to the CGRP1 receptor show antagonistic properties in a rat blood flow assay," Regul. Pept. vol. 79: 153-58, Feb. 1999, 8 pages.
Rist et al., "From Micromolar to Nanomolar Affinity: A Systematic Approach to Identify the Binding Site of CGRP at the Human Calcitonin Gene-Related Peptide 1 Receptor," J. Med. Chem. 41: 117-123, Jan. 1998, 7 pages.
Ritter et al., "A Textbook of Clinical Pharmacology: 4th Edition," Chapters 16, 22, 24, Oxford University Press, 1999, 25 pages.
RituxanTM (rituximab) Prescribing Information, Nov. 1997, 2 pages.
Rizzoli, "Synaptic Vesicle Pools," Nature Reviews: Neuroscience, vol. 6, Jan. 2005, 13 pages.
Roon et al., "Bovine isolated middle cerebral artery contractions to antimigraine drugs," Naunyn-Schmiedeberg's Arch Pharmacol vol. 360:591-596, Nov. 1999, 6 pages.
Roon et al., "No Acute Antimigraine Efficacy of CP-122,288, a Highly Potent Inhibitor of Neurogenic Inflammation. Results of Two Randomized, Double-Blind, Placebo-Controlled Clinical Trials," Ann Neurol 47(2):238-241, Feb. 2000, 4 pages.
Roon et al., "Pharmacokinetic profile of alniditan nasal spray during and outside migraine attacks," Br J Clin Pharmacol vol. 47:285-290, Mar. 1999, 6 pages.
Rovero et al., "CGRP Antagonist Activity of Short C-Terminal Fragments of Human aCGRP, CGRP(23-37) and CGRP(19-37)," Peptides 13(5):1025-1027, Sep.-Oct. 1992, 3 pages.
Rozen, "Cluster headache: diagnosis and treatment," Curr Pain Headache Rep 9:135-140, 2005, 6 pages.
Rudikoff et al., "Single amino acid substitution altering antigen-binding specificity," Proc Natl Acad Sci USA 79(6):1979-1983, Mar. 1982, 5 pages.
Saito and Koshino, "Distribution of Neuropeptides in Synovium of the Knee with Osteoarthritis," Clinical Orthopaedics and Related Research, Jul. 2000, 376: 172-182.
Saleh et al., "Phase I trial of the chimeric anti-GD2 monoclonal antibody ch14.18 in patients with malignant melanoma," Hum Antibodies Hybridomas 3(1):19-24, Jan. 1992, 6 pages.
Salman et al., "An Improved Protocol for Coupling Synthetic Peptides to Carrier Proteins for Antibody Production Using DMF to Solubilize Peptides," Journal of Biomolecular Techniques 18:173-176, Jul. 2007, 4 pages.
Salmon et al., "Altered neuroadaptation in opiate dependence and neurogenic inflammatory nociception in αCGRP-deficient mice," Nature Neuroscience, Apr. 2001, 4(4): 357-358.
Sanchez del Rio et al., "How to pick optimal acute treatment for migraine headache," Current Pain and Headache Reports, vol. 5, Apr. 2001, 9 pages.
Sandborn and Yednock, "Novel Approaches to Treating Inflammatory Bowel Disease: Targeting Alpha-4 Integrin," The American Journal of Gastroenterology, vol. 98, No. 11, Nov. 2003, 11 pages.
Sandor, "Nervous control of the cerebrovascular system: doubt and facts," Neurochemistry International 35:237-259, 1999, 23 pages.
Santora et al., "Characterization of Noncovalent Complexes of Recombinant Human Monoclonal Antibody and Antigen Using Cation Exchange, Size Exclusion Chromatography, and BIAcore," Analytical Biochemistry, 299: 119-129, Dec. 2001, 11 pages.
Saper et al., "DHE in the Pharmacotheraphy of Migraine Potential for a Larger Role," Headache vol. 46(Suppl. 4), Nov. 2006, 9 pages.
Sarchielli et al., "Sensitization, glutamate, and the link between migraine and fibromyalgia," Current Pain and Headache Reports OCT, vol. 11, No. 5, Oct. 2007, 9 pages.
Saxena et al., "5HT1-like receptor agonists and the pathophysiology of migraine," Trends Pharmacol Sci vol. 10,5:200-204, May 1989, 5 pages.
Saxena et al., "Effects of tertatolol, a β-adrenoceptor antagonist with agonist affinity at 5-HT1A receptors, in an animal model of migraine: comparison with propanolol and pindolol," European Journal of Pharmacology, 220, Sep. 1992, 8 pages.
Saxler et al., "Localization of SP- and CGRP-immunopositive nerve fibers in the hip joint of patients with painful osteoarthritis and of patients with painless failed total hip arthroplasties," Eur J Pain, 2007, 11: 67-74.
Schaible et al., "Mechanisms of pain in arthritis," Ann N Y Acad Sci 966:343-354, Jun. 2002, 16 pages.
Scher et al., "Cardiovascular risk factors and migraine. The GEM population-based study," Neurology 64:614-620, Feb. (2 of 2) 2005, 7 pages.
Schmitz et al., "Frontal lobe structure and executive function in migraine patients," Neuroscience Letters, 1;440(2):92-6, Aug. 2008, 5 pages.
Schoenen et al., "Neurophysical features of the migrainous brain," Features of the Migrainous Brain, Neurol Sci, vol. 27, S77-S81, May 2006, 5 pages.
Schoenen et al., "No effect of eletriptan administration during the aura phase of migraine," European Journal of Neurology, vol. 11, 671-677, Oct. 2004, 7 pages.
Schoenen et al., "When should triptans be taken during a migraine attack?" Leading Article, CNS Drugs, vol. 15(8), Aug. 2001, 5 pages.
Schoonman et al., "Chapter 1: the prevalence of premonitory symptoms in migraine: a questionnaire study in 461 patients," Cephalalgia 26:1209-1213, 2006, 8 pages.
Schoonman et al., "Chapter 3: Normobaric hypoxia and nitroglycerin as trigger factors for migraine," Cephalalgia, vol. 26(7):816-9, Jul. 2006, 8 pages.
Schoonman et al., "Gabapentin in Migraine Prophylaxis: Is it Effective and Well Tolerated?" Headache, vol. 42, Issue 3, Mar. 2002, 1 page.
Schoonman et al., "Is stress a trigger factor for migraine?" Psychoneuroendocrinology 32(5):532-538, Jun. 2007, 7 pages.
Schoonman et al., "Magnetic resonance angiography of the human middle meningeal artery: implications for migraine," Journal of Magnetic Resonance Imagining, 24:918-921, Oct. 2006, 4 pages.
Schoonman et al., "Migraine headache is not associated with cerebral or meningeal vasodilatation—a 3T magnetic resonance angiography study," Brain 131:2192-2200, Aug. 2008, 9 pages.
Schueren et al., "Reproductivity of the capsaicin-induced dermal blood flow response as assessed by laser Doppler perfusion imaging," Br J Clin Pharmacol 64(5):580-590, 2007, 11 pages.
Schulman et al., "Defining Refractory Migraine and Refractory Chronic Migraine: Proposed Criteria From the Refractory Headache Special Interest Section of the American Headache Society", Headache 48:778-782, 2008, 6 pages.
Schytz et al., "PACAP38 induces migraine-like attacks in patients with migraine without aura," Brain, vol. 132 (part 1): 16-25, Jan. 2009, 10 pages.

(56) References Cited

OTHER PUBLICATIONS

Scimemi and Beato, "Determining the Neurotransmitter Concentration Profile at Active Synapses", Molecular Neurobiology 40(3): 289-306, Oct. 2009, 18 pages.
Scott et al., "Sumatriptan and cerebral perfusion in healthy volunteers," British Journal of Clinical Pharmacology 33(4):401-404, Apr. 1992, 4 pages.
seekingalpha.com [online], "Teva Pharmaceutical Industries (TEVA) Q3 2017 Results—Earnings Call Transcript," available on or before Nov. 2, 2017, retrieved on Dec. 11, 2018, retrieved from URL: <https://seekingalpha.com/article/4119613-teva-pharmaceutical-industries-teva-q3-2017-results-earnings-call-transcript#question-answer-session>, 3 pages.
Seifert et al., "Chapter 7: (Patho)physiological and Therapeutic Relevance of Constitutive Activity and Inverse Agonism at G Protein-Coupled Receptors" in G-Protein-Coupled Receptors as Drug Targets: Analysis of Activation and Constitutive Activity, vol. 24, 2006, 11 pages.
Seon et al., "Isolation, Structure, Synthesis, and Activity of a New Member of the Calcitonin Gene-related Peptide Family from Frog Skin and Molecular Cloining of Its Precursor," The Journal of Biological Chemistry 275(8):5934-5940, 2000, 8 pages.
Seong et al., "Radiation-induced alteration of pain-related signals in an animal model with bone invasion from cancer," Ann N Y Acad Sci 1030:179-186, Dec. 2004, 8 pages.
Shapiro and Goadsby, "The long drought the dearth public funding for headache research," Cephalalgia, vol. 27, Sep. 2007, 4 pages.
Shaw et al., "The effect of monoclonal antibodies to calcitonin gene-related peptide (CGRP) on CGRP-induced vasodilatation in pig coronary artery rings," Brit J Pharmacol 106:196-198, 1992, 3 pages.
Shawket et al., "Prolonged effect of CGRP in Raynaud's patients: a double-blind randomised comparison with prostacyclin," Br J Clin Pharmac 32:209-213, 1991, 5 pages.
Shawket et al., "Selective Suprasensitivity to Calcitonin-Gene-Related Peptide in the Hands in Raynaud's Phenomenon," The Lancet 1354-1385, Dec. 9, 1989, 4 pages.
Sheets et al., "Efficient construction of a large nonimmune phage antibody library: the production of high-affinity human single-chain antibodies to protein antigens," Proc Natl Acad Sci USA 95(11):6157-6162, May 26, 1998, 7 pages.
Shepheard et al., "Possible antimigraine mechanisms of action of the 5HT1F receptor agonist LY334370," Cephalalgia 19:851-858, Dec. 1999, 8 pages.
Shepherd and Dean, "Monoclonal Antibodies: A Practical Approach," Chapters 1, 2, 12, 13, 20, 21, Oxford University Press, Jul. 13, 2000, 151 pages.
Shields and Goadsby, "Seritonin receptors modulate trigeminovascular responses in ventroposteromedial nucleus of thalamus: a migraine target?" Neurobiology of Disease 23:491-501, Sep. 2006, 11 pages.
Shields et al, "Inhibition of Allergic Reactions with Antibodies to IgE," International Archives for Allergy and Immunology, 107: 308-312, May-Jun. 1995, 5 pages.
Sigma-Aldrich, "Biochemicals & Reagents for Life Science Research," pp. 350-352, 2004, 7 pages.
Silberstein et al., "Advances in the understanding of the pathophysiology headache," Neurology, vol. 42(suppl.2): 6-10, Mar. 1992, 5 pages.
Silberstein et al., "Botulinum toxin type A for the prophylactic treatment of chronic daily headache: a randomized, double-blind, placebo-controlled trial," Mayo Clinic Proceedings, Sep. 2005, 12 pages.
Silberstein et al., "Chapter 5: Pathophysiology of Headache, Chapter 6: Genetics of Headache, Chapter 9: Migraine—Diagnosis and Treatment & Chapter 12: Cluster Headache—Diagnosis, Management and Treatment," in Wolff s Headache and other head pain: Seventh Edition, Oxford Press 2001, 180 pages.
Silberstein et al., "CNS effects of sumatriptan and rizatriptan," Cephalalgia, Jan. 2004, 2 pages.
Silberstein et al., "Efficacy and Safety of Topiramate for the Treatment of Chronic Migraine: A Randomized, Double-Blind, Placebo-Controlled Trial," Headache 170-180, Feb. 2007, 11 pages.
Silberstein et al., "From migraine mechanisms to innovative therapeutic drugs," Neurology, vol. 64 (Suppl 2), May 2005, 3 pages.
Silberstein et al., "Migraine: preventive treatment," Cephalalgia, vol. 22, Sep. 2002, 22 pages.
Silberstein et al., "Preventive treatment of migraine," Neurology, 60(Suppl 2):S38-S44, 2003, 7 pages.
Silberstein et al., "Removing barriers to appropriate migraine treatment: formulary limitations and triptan package size," Headache, Oct. 2005, 5 pages.
Silberstein et al., "Section 2: Primary Headache Disorders, Chapter 6: Migraine: diagnosis and treatment," in Headache in Primary Care, Isis Medical Media, 1999, 32 pages.
Silberstein, "Cardiovascular risk factors associated with migraine," Lancet Neurol, Jul. 2005, 2 pages.
Silberstein, "Chronic migraine: diagnosis and management strategy," Reviews in Neuological Diseases, vol. 1, No. 3, Summer 2004, 6 pages.
Silberstein, "Current Preventive Therapy: Preventive treatment mechanism," Headache Currents, vol. 3, No. 5, Sep./Oct. 2006, 8 pages.
Silberstein, "Migraine pathophysiology and its clinical implications," Cephalalgia, 24 Suppl. 2, Feb. 2004, 6 pages.
Silberstein, "Migraine prevention medication reduces resource utilization," Research Submissions: Headache, Mar. 2003, 8 pages.
Silberstein, "Migraine," Lancet, vol. 363, Jan. 2004, 11 pages.
Silberstein, "Migraine: preventive treatment," Current Medical Research and Opinion, vol. 17, Suppl. 1, S87-93, 2001, 7 pages.
Silberstein, "Preventive treatment of headaches," Current Opinion in Neurology, Jun. 2005, 4 pages.
Silberstein, "Preventive treatment of migraine," Review in Neurological Diseases, vol. 2, No. 4, Fall 2005, 9 pages.
Silberstein, "Preventive treatment of migraine," Trends in Pharmacological Sciences, vol. 27, No. 8, Aug. 2006, 6 pages.
Silberstein, "Review of botulinum toxin type A and its clinical applications in migraine headache," Expert Opinion Phermacother, vol. 2 (10), Oct. 2001, 6 pages.
Silberstein, "The International Classification of Headache Disorders, 2nd Edition (ICHD-II)—revision of criteria for 8.2 Medication-overuse headache," Cephalalgia, Jun. 2005, 6 pages.
Silberstein, "Topiramate in migraine prevention," Headache, Apr. 2005, 9 pages.
Silberstein, "Migraine," Discovery Medicine, Jul. 12, 2009, pp. 1.
Simulect® (basiliximab), "Prescribing Information," Novartis Pharmaceuticals Corporation, May 1998, 7 pages.
Sixt et al., "Calcitonin gene-related peptide receptor antagonist olcegepant acts in the spinal trigeminal nucleus," Brain 132:3134-3141, Nov. 2009, 8 pages.
Smith et al., "An immunocytochemical investigation of human trigeminal nucleus caudalis: CGRP, substance P and 5-HT$_{1D}$-receptor immunoreactivities are expressed by trigeminal sensory fibres," Cephalalagia 22:242-432, Jul. 2002, 10 pages.
Smith et al., "Reversal of advanced digoxin intoxication with Fab fragments of digoxin-specific antibodies," N Eng J Med 294(15):797-800, Apr. 8, 1976, 4 pages.
Smith-Gill et al., "Contributions of immunoglobulin heavy and light chains to antibody specificity for lysozyme and two haptens," J Immunol 139(12):4135-4144, Dec. 15, 1987, 10 pages.
Song et al., "Light chain of natural antibody plays a dominant role in protein antigen binding," Biochem Biophys Res Commun 268(2):390-394, Feb. 16, 2000, 5 pages.
Sparey, "Embracing partnerships: the Merck philosophy", Biopartnering Magazine, Spring 2006, 3 pages.
Sprenger and Goadsby, "Migraine pathogenesis and state of pharmacological treatment options," BMC Med 7(71), 5 pages, Nov. 16, 2009, 5 pages.
Stam, "Migraine: new treatment options from molecular biology," Expert Rev Neurotherapeutrics, 5(5), Sep. 2005, 9 pages.
Steiner et al., "BASH Management Guidelines: Guidelines for all Doctors in the Diagnosis and Management of Migraine and Tension-Type Headache (2nd edition)," BASH Management Guidelines, Mar. 2000, 31 pages.

(56) References Cited

OTHER PUBLICATIONS

Steiner et al., "The prevalence and disability burden of adult migraine in England and their relationships to age, gender and ethnicity," Cephalalgia, vol. 23, Sep. 2003, 9 pages.
Sternini, "Enteric and Visceral Afferent CGRP Neurons, Targets of Innercation and Differential Expression Patterns," Annals New York Academy of Sciences 170-185, 1992, 17 pages.
Stjernsward et al., "The World Health Organization Cancer Pain and Palliative Care Program. Past, present, and future," J Pain Symptom Manage 12(2):65-72, Aug. 1996, 8 pages.
Storer et al., "Calcitonin gene-related peptide (CGRP) modulates nociceptive trigeminovascular transmission in the cat," Brit J Pharmacol 142(7):1171-1181, Aug. 2004, 11 pages.
Strecker et al., "Nitric Oxide Releases Calcitonin-Gene-Related Peptide from Rat Dura mater Encephali Promoting Increases in Meningeal Blood Flow," Journal of Vascular Research 39:489-496, Nov.-Dec. 2002, 8 pages.
Strorer and Goadsby, "Topiramate inhibits trigeminovascular neurons in the cat," Cephalalgia 24:1049-1056, Dec. 2004, 8 pages.
Struthers et al., "Human calcitonin gene related peptide: a potent endogenous vasodilator in man," Clinical Science 70:389-393, 1986, 5 pages.
Subramanian, "Antibodies vol. 2—Novel Technologies and Therapeutic Use," Springer Science+Business Media New York, Jan. 2004, 239 pages.
Supowit et al., "Calcitonin Gene-Related Peptide Protects Against Hypertension-Induced Heart and Kidney Damage," Hypertension, vol. 45:109-14, Jan. 2005, 8 pages.
Swillens, "Interpretation of Binding Curves Obtained with High Receptor Concentrations: Practical Aid for Computer Analysis," Molecular Pharmacology 47:1197-1203, 1995, 7 pages.
Synagis® (palivizumab) EMA Scientific Discussion, 2004, 19 pages.
Szabat et al., "Production and characterization of monoclonal antibody against human calcitonin gene-related peptide (CGRP) and its immunohistochemical application to salivary glands," Histochemical Journal 26:317-326, 1994, 10 pages.
Takhshid et al., "Characterization and effects on cAMP accumulation of adrenomedullin and calcitonin gene-related peptide (CGRP) receptors in dissociated rat spinal cord cell culture," Brit J Pharmacol 148(4):459-468, Jun. 2006, 10 pages.
Tamura et al., "Structural correlates of an anti carcinoma antibody: identification of specificity-determining residues (SD Rs) and development of a minimally immunogenic antibody variant by retention ofSDRs only," J Immunol 164(3):1432-1441, Feb. 1, 2000, 11 pages.
Tan et al., "Calcitonin gene-related peptide as an endogenous vasodilator: immunoblockade studies in vivo with an anti-calcitonin gene-related peptide monoclonal antibody and it's Fab' fragment," Clinical Science 89(6):565-573, Dec. 1, 1995, 9 pages.
Tan et al., "Demonstration of the neurotransmitter role of calcitonin gene-related peptides (CGRP) by immunoblockade with anti-CGRP monoclonal antibodies," Brit J Pharmacol 111(3):703-710, Mar. 1994, 8 pages.
Tao and Morrison, "Studies of Aglycosylated Chimeric Mouse-Human Ig:. Role of Carbohydrate in the Structure and Effector Functions Mediated by the Human IgG Constant Region," Journal of Immunology, 143: 2595-2601, No. 8, Oct. 15, 1989, 8 pages.
Tepper et al., "Botulinum neurotoxin type A in the preventive treatment of refractory headache: a review of 100 consecutive cases," Headache 44(8):794-800, Sep. 2004, 8 pages.
Tepper et al., "Mechanisms of Action of the 5-HT 1B/1D Receptor Agonists," Neurological Review, Arch. Neurol. vol. 59, pp. 1084-1088, Jul. 2002, 5 pages.
Terwindt et al., "Hemiplegic and basilar-type migraine: current and future treatment," Headache Currents No. 4:97-99, Jul.-Aug. 2006, 4 pages.
Terwindt et al., "Migraine en cardiovasculair risico," Ned Tijdsch Geneeskd 151(37) 2029-2031, 2007, 3 pages.
Terwindt et al., "The impact of migraine on quality of life in the general population. The GEM study," Neurology vol. 55:624-629, Sep. 2000, 6 pages.
Teva Pharmaceutical Industries, "Teva announces U.S. Approval of AJOVY (fremanezumab-vfrm) injection, the first and only anti-CGRP treatment with both quarterly and monthly dosing for the prevention of migraine in Adults," Teva Pharmaceutical Industries Ltd., available on or before Sep. 14, 2018, 8 pages.
Textbook of Pain Levine et al., Textbook of Pain pp. 45-56, 1994, 17 pages.
Textbook of Pain McCarthy et al., Textbook of Pain pp. 387-395, 1994, 15 pages.
Tfelt-Hansen et al., "Calcitonin gene-related peptide in blood is it increased in the external jugular vein during migraine and cluster headache: A review," Journal of Headache Pain, vol. 10, Jun. 2009, 7 pages.
Tfelt-Hansen et al., "Ergotamine in the acute treatment of migraine—a review and European consensus," Brain 123:9-18, Jan. 2000, 10 pages.
Tfelt-Hansen et al., "Guidelines for controlled trials of drugs in migraine: second edition," Cephalalgia vol. 20:765-786, Nov. 2000, 22 pages.
Troltzsch et al., "The calcitonin gene-related peptide (CGRP) receptor antagonist BIBN4096BS reduces neurogenic increases in dural blood flow," European Journal of Pharmacology 562:103-110, 2007, 8 pages.
Tsai et al., "Cerebral arterial innvervation by nerve fibers containing CGRP: I. Distribution and Origin of CGRP Perivascular Innervation in the Rat," The Journal of Comparative Neurology, vol. 271: 435-444, May 1988, 10 pages.
Tsurushita et al., "Design of Humanized Antibodies: From anti-Tac to Zenapax," Methods 36: 69-83, May 2005, 15 pages.
Tuma, "Phase I Antibodie Risks: Trial Safety Explained," Journal of Natural Cancer Inst. vol. 98(14): 956-98, Jul. 19, 2006, 3 pages.
Tvedskov et al., "No Increase of Calcitonin Gene-Related Peptide in Jugular Blood during Migraine", Annals of Neurobilogy, vol. 58, No. 4, Oct. 2005, 8 pages.
Tvedskov et al., "The prophylactic effect of valproate on glyceryltrinitrate induced migraine," Cephalalgia 24(7):576-585, Jul. 2004, 10 pages.
Tysabri (natalizumab), "Prescribing Information," Biogen Idec Inc., Nov. 2004, 11 pages.
Tysabri® Letter from the Food and Drug Administration, Nov. 2004, 7 pages.
Tzabazis et al., "Antihyperalgesic effect of a recombinant herpes virus encoding antisense for calcitonin gene-related peptide," Anesthesiology 106(6):1196-1203, Jun. 2007, 8 pages.
Uddman et al., "Calcitonin gene-reglated peptide (CGRP) pervascular distribution and vasodilatory effects," Regulatory Peptides, vol. 15, Aug. 1986, 23 pages.
Uddman et al., "Innvervation of the feline cerebral vasculature by nerve fibers containing CGRP," Neuroscience Letters, vol. 62, Nov. 1985, 6 pages.
Urban et al., "Functional Selectivity and Classical Concepts of Quantitative pharmacology," The Journal of Pharmacology and Experimental Therapeutics 320(1):1-13, Jan. 2007, 13 pages.
Vajdos et al., "Comprehensive functional maps of the antigen-binding site of an anti-ErbB2 antibody obtained with shotgun scanning mutagenesis," J Mol Biol 320(2):415-428, Jul. 5, 2002, 14 pages.
Van der Kamp et al., "Interictal cortical hyperexcitability in migraine patients demonstrated with transcranial magnetic stimulation," Journal of the Neurological Sciences, vol. 139:106-110, Jul. 1996, 5 pages.
Van der Schueren, "Reproducibility of the capsaicin-induced dermal blood flow response as assessed by laser Doppler perfusion imaging," British Journal of Clinical Pharmacology 64:580-590, Nov. 2007, 11 pages.
Van Dijk et al., "Human antibodies as next generation therapeutics," Current Opinion in Chemical Biology, vol. 5: 368-374, Aug. 2001, 7 pages.
Van Dijk et al., "No confirmation of visual evoked potential diagnostic test for migraine," Lancet vol. 337 i:517-518, Mar. 2, 1991, 2 pages.

(56) References Cited

OTHER PUBLICATIONS

Van Dijk et al., "Visual evoked potentials and background EEG activity in migraine," Headache 31:392-395, Jun. 1991, 4 pages.
Van Regenmortal et al., "Improving the Quality of BIACORE-Based Affinity Measurements," Dev. Biol. (Basel), 112: 141-151, 2003, 11 pages.
Van Valen et al., "Calcitonin Gene-Related Peptide (CGRP) Receptors are Linked to Cyclic Adenosine Monophosphate Production in SK-N-MC Human Neuroblastoma Cells," Neuroscience Letters 119: 195-198, Nov. 1990, 4 pages.
Van Vliet et al., "Cardiovascular autonomic function tests in cluster headache," Cephalalgia 26:329-331, Mar. 2006, 3 pages.
Van Vliet et al., "Evaluating the IHS criteria for cluster headache—a comparison between patients meeting all criteria and patients failing one criterion," Cephalalgia 26: 241-245, Mar. 2006, 5 pages.
Van Vliet et al., "Features involved in the diagnostic delay of cluster headache," J Neurol Neurosurg Psychiatry vol. 74(8):1123-1125, Aug. 2003, 3 pages.
Van Vliet et al., "Intranasal sumatriptan in cluster headache," Neurology 60:-633, Feb. (2 of 2) 2003, 5 pages.
Van Wijngaarden et al, "Inhibitors of Ocular Neovascularization: Promises and Potential Problems," JAMA, American Medical Association 293(12):1509-1513, Mar. 2005, 5 pages.
Vater and Klussmann, "Toward third-generation aptamers: Spieglemers and their therapeutic prospects," Curr Opin Drug Discov & Devel 6(2):253-261, Mar. 2003, 9 pages.
Vater et al., "Short bioactive Spiegelmers to migraine-associated calcitonin gene-related peptide rapidly identified by a novel approach: tailored-SELEX," Nucleic Acids Res 31(21):e130, Nov. 1, 2003, 7 pages.
Vaughan et al., "Human antibodies with sub-nanomolar affinities isolated from a large non-immunized phage display library," Nat Biotechnol 14(3):309-314, Mar. 1996, 6 pages.
Verge et al., "Differential Influence of Nerve Growth Factor on Neuropeptide Expression in vivo: A Novel Role in Peptide Suppression in Adult Sensory Neurons," J Neuroscience, Mar. 1995, 15(3): 2081-2096.
Verhoeff et al., "Dopamine D2-receptor imaging with 123I-Iodobenzamide SPECT in migraine patients abusing ergotamine: does ergotamine cross blood brain barrier?" Cephalalgia 13:325-329, Oct. 1993, 5 pages.
Verkman, "Drug discovery in academia," Am J Physiol Cell Physiol 286:C465-C47, Mar. 2004, 10 pages.
Vincent et al., "Molecular targets for autoimmune and genetic disorders of neuromuscular transmission," Eur J Biochem 267(23):6717-6728, Dec. 2000, 12 pages.
Visser et al., "311C90, a new central and peripherally acting 5-HT1D receptor agonist in the acute oral treatment of migraine: a double blind, placebo-controlled, dose-range finding study," presented in part at the 10th Migraine Trust, Sep. 5-8, 1994, Neurology, Feb. 1996, 5 pages.
Visser et al., "Clinical trials and therapeutics, Pharmacokinetic and pharmacodynamic profiles of sumatriptan in migraine patients with headache recurrence or no response," Clinical Pharmacology and Therapeutics, vol. 60, No. 4, Oct. 1996, 9 pages.
Visser et al., "Subcutaneous Sumatriptan International Study Group. Treatment of migraine attacks with migraine attacks with subcutaneous sumatriptan: first placebo-controlled study," Cephalalgia 12:308-314, Oct. 1992, 6 pages.
Visser et al., "Sumatriptan in clinical practice: a 2-year review of 453 migraine patients," Neurology 47:46-51, Jul. 1996, 7 pages.
Visser et al., "Sumatriptan non-responders: a survey in 366 migraine patients," Headache vol. 36:471-475, Sep. 1996, 5 pages.
Wacnik et al., "Tumor-induced mechanical hyperalgesia involves CGRP receptors and altered innervation and vascularization of DsRed2 fluorescent hindpaw tumors," Pain 115(1-2):95-106, May 2005, 6 pages.
Waeber et al., "Migraine as an inflammatory disorder", Neurology 64(10 Suppl 2):S9-15, May 2005, 7 pages.

Wang et al., "Monoclonal antibody pharmacokinetics and pharmacodynamics", Clinical Pharmacology and Therapeutics, 84(5), 548-558, Nov. 2008, 11 pages.
Ward et al., "Binding activities of a repertoire of single immunoglobulin variable domains secreted from *Escherichia coli*," Nature 341(6242):544-546, Oct. 12, 1989, 3 pages.
Weir et al., "Formatting antibody fragments to mediate specific therapeutic functions," Biochemical society transations vol. 30, part 4, Aug. 2002, 5 pages.
Welch, "MRI of the occipital cortex, red nucleus, and substantia nigra during visual aura of migraine," Neuology, vol. 51:1465-1469, Nov. 1998, 5 pages.
Werry and Aman, "Practitioner's Guide to Psychoactive Drugs for Children and Adolescents, 2nd Edition," Plenum Publishing Corporation, pp. 42-50, 1999, 11 pages.
Werther et al., "Humanization of an Anti-lymphocyte Function-Associated Antigen (LFA)-1 Monoclonal Antibody and Reengineering of the Humanized Antibody for Binding to Rhesus LFA-1," J. Immunol. 157: 4986-4995, Dec. 1996, 10 pages.
Wicher et al., "Immunogenicity of Three Recombinant Treponema pallidum Antigens Examined in Guinea Pigs," Int. Arch. Allergy Appl. Immunol. 89 128-135, 1989, 8 pages.
Wick et al., "Transient receptor potential vanilloid 1, calcitonin gene-related peptide, and substance p. mediate nociception in acute pancreatitis," Am J Physiol Gastrointest Liver Physiol 290(5):G959-G969, May 2006, 11 pages.
Wiendels and Ferrari, "Treating migraine attacks asap: concept and methodological issues," Progress in Neurotherapeutics and Neuropsychopharmacology, vol. 1 p. 53-61, Jan. 2006, 9 pages.
Wiendels et al., "Chapter 2: Chronic frequent headache in the general population—prevalence and associated factors & Chapter 3: Chronic frequent headaches in the general population—comorbidity and quality of life," Cephalalgia vol. 26:1434-1442, 2006, 161 pages.
Wild et al., "Determination of the Human Cytochrome P450 Isoforms Involved in the Metabolism of Zolmitriptan," Xenobiotica, vol. 29, pp. 847-857, Aug. 1999, 12 pages.
Williamson et al., "Intravital microscope studies on the effects of neurokinin agonists and calcitonin gene-related peptide on dural vessel diameter in the anaesthetized rat," Cephalalgia 17(4):518-524, Jun. 1997, 14 pages.
Williamson et al., "Role of opioid receptors in neurogenic dural vasodilation and sensitization of trigeminal neurons in anaesthetized rats," British Journal of Pharmacology 133 807-814, Jul. 2001, 8 pages.
Williamson et al., "Sumatriptan inhibits neurogenic vasodilation of dural blood vessels in the anaesthetized rat—intravital microscope studies," Cephalalgia 17(4):525-531, Jun. 1997, 12 pages.
Williamson et al., "The Novel Anti-Migraine Agent Rizatriptan Inhibits Neurogenic Dural Vasodilation and Extravasation," European Journal of Pharmacology, vol. 328, pp. 61-64, Jun. 1997, 4 pages.
Wimalawansa et al., "Isolation, Purification, and Characterization of Calcitonin Gene-Related Peptide Receptor," Peptides 14:691-699, 1993, 9 pages.
Wimalawansa, "Cacitonin Gene-Related Peptide and Its Receptors: Molecular Genetics, Physiology, Pathophysiology, and Therapeutic Potentials," Endocrine Reviews 17(5):553-585, Oct. 1996, 53 pages.
Winkler et al., "Changing the antigen binding specificity by single point mutations of an anti-p24 (HIV-1) antibody," J Immunol 165(8):4505-4514, Oct. 15, 2000, 11 pages.
Wisskrichen et al., "Bioactive β-bend structures for the antagonist hα CGRP $_{8-37}$ at the CGRP$_1$ receptor of the rat pulmonary artery," British Journal of Pharmacology 129:1049-+1055, 2000, 7 pages.
Witte, "The madness of migraine," Scientific American Mind 39-43, Dec. 2006-Jan. 2007, 6 pages.
Wong et al., "Monoclonal antibody to rat alpha-CGRP: production, characterization, and in vivo immunoneutralization activity," Hybridoma 12(1):93-106, Feb. 1993, 14 pages.
Wong et al., "Preparation of a monoclonal antibody to rat alpha-CGRP for in vivo immunoneutralization of peptides," Ann N Y Acad Sci 657:525-527, Jun. 30, 1992, 3 pages.

(56) References Cited

OTHER PUBLICATIONS

Woods et al., "Bilateral spreading cerebral hypoperfusion during spontaneous migraine and headache," the New England Journal of Medicine, Brief Report, vol. 331, No. 25, Dec. 1994, 4 pages.
World Health Organization (WHO), "General policies for monoclonal antibodies," INN Working Document 09.251 Revised, Dec. 2009, 4 pages.
World Health Organization (WHO), "WHO Drug Information," WHO Drug Information vol. 30, No. 2, 2016, 187 pages.
World Health Organization, "The use of stems in the selection of international nonproprietary names (INN) for pharmaceutical substances," Programme on International Nonproprietary Names (INN), 2006, 170 pages.
Wright and Morrison, "Effect of Glycosylation on Antibody Function: Implications for Genetic Engineering," Trends Biotechnology 15: 26-32, Jan. 1997, 7 pages.
Wu et al., "Development and potential of non-peptide antagonists for calcitonin-gene-related peptide (CGRP) receptors: evidence for CGRP receptor heterogeneity," Biochem Soc Trans 30(4):468-473, Aug. 2002, 6 pages.
Wu et al., "Humanization of a murine monoclonal antibody by simultaneous optimization of framework and CDR residues," J Mol Biol 294(1):151-162, Nov. 19, 1999, 12 pages.
Wu et al., "Stepwise in vitro Affinity Maturation of Vitaxin, an alphavbeta3-Specific Humanized mAb," Proc. Natl. Acad. Sci. USA 95: 6037-42, May 1998, 6 pages.
Wu et al., "Ultra-Potent Antibodies Against Respiratory Syncytial Virus: Effects of Binding Kinetics and Binding Valence on Viral Neutralization," J. Mol. Biol. 350: 126-144, Jul. 2005, 19 pages.
Wyon et al., "Urinary Excretion of Calcitonin Gene-related Peptide in Males with Hot Flushes after Castration for Carcinoma of the Prostate," Scand J Urol Nephrol 35:92-96, May 2001, 5 pages.
Xu et al., "Essential role of the TNF-TNFR2 cognate interation in mouse dendritic cell-natural killer cell crosstalk," Blood, vol. 109, No. 8, Apr. 2007, 10 pages.
Xu, "Study on the Mechanism of SP and CGRP in the Chronic Pain and Knee Joint," Master Thesis. Guangxi Medical University. May 2005. (In Chinese with Engish abstract), 57 pages.
Yang et al., "CDR Walking Mutagenesis for the Affinity Maturation of a Potent Human Anti-HIV-1 Antibody into the Picomolar Range," J. Mol. Biol. 254: 392-403, Dec. 1995, 12 pages.
Yeomans et al., U.S. Appl. No. 60/711,950, filed Aug. 26, 2005, 47 pages.
Young et al., "Transcranial Doppler: technique and application to headache," Headache, Mar. 1992, 7 pages.
Zanetti and Capra, "The Antibodies vol. 1," Chapters 2, 3, 4, 5, 6, Harwood Academic Publishers, 1995, 137 pages.
Zeller et al., "Cgrp function-blocking antibodies inhibit neurogenic vasodilatation without affecting heart rate or arterial blood pressure in the rat," Brit J Pharmacol 155(7):1093-1103, Dec. 2008, 11 pages.
ZevalinTM (ibritumomab tiuxetan) Prescribing Information, Dec. 21, 2001, 38 pages.
Zhang et al., "Arthritic calcitonin/α calcitonin gene-related peptide knockout mice have reduced nociceptive hypersensitivity," Pain, 2001, 89: 265-273.
Zhang et al., "Rheumatoid factor specificity of a VH3-encoded antibody is dependent on the heavy chain CDR3 region and is independent of protein A binding," J Immunol 161(5):2284-2289, Sep. 1, 1998, 7 pages.
Zhang et al., "Sensitization of calcitonin modifying protein-1 in the trigeminal gene-related peptide receptors by receptor activity-ganglion," J Neurosci 27(10):2693-2703, Mar. 7, 2007, 11 pages.
Zittel et al., "Role of spinal afferents and calcitonin gene-related peptide in the postoperative gastric ileus in anesthetized rats," Ann Surg 219(1):79-87, Jan. 1994, 9 pages.
Zomig (zolmitriptan) tablets and Zomig-ZMT (zolmitriptan) Orally Disintegrating Tablets, "Prescribing Information," AstraZeneca 2000, last revised: Feb. 12, 2001, 28 pages.
Zwetsloot et al., "Blood flow velocities in the vertebrobasilar system during migraine attacks—a transcranial Doppler study," Cephalalgia vol. 12:29-32, Feb. 1992, 4 pages.
Zwetsloot et al., "Blood Flow velocity changes in migraine attacks—a transcranial doppler study," Cephalalgia vol. 11:103-107, May 1991, 5 pages.
Zwetsloot et al., "Lack of asymmetry of middle cerebral artery blood flow velocity in unilateral migraine," Stroke, vol. 24, No. 9, Sep. 1993, 4 pages.
Zwetsloot et al., "Vascular reactivity during migraine attacks: a transcranial Doppler study," Headache, Oct. 1991, 3 pages.
*Eli Lilly and Company* v *Teva Pharmaceauticals International GMBH*, "Declaration of Dr. Andrew Charles," Case No. IPR2018-01711, U.S. Pat. No. 9,884,907, Oct. 1, 2018, 114 pages.
*Eli Lilly and Company* v *Teva Pharmaceauticals International GMBH*, "Declaration of Andrew Charles, M.D.," Case No. IPR2018-01422, U.S. Pat. No. 9,340,614, Aug. 7, 2018, 93 pages.
*Eli Lilly and Company* v *Teva Pharmaceauticals International GMBH*, "Declaration of Andrew Charles, M.D.," IPR2018-01423, U.S. Pat. No. 9,266,951, Aug. 7, 2018, 98 pages.
*Eli Lilly and Company* v *Teva Pharmaceauticals International GMBH*, "Declaration of Andrew Charles, M.D.," Case No. IPR2018-01424, U.S. Pat. No. 9,346,881, Aug. 7, 2018, 99 pages.
*Eli Lilly and Company* v *Teva Pharmaceauticals International GMBH*, "Declaration of Andrew Charles, M.D.," IPR2018-01425, U.S. Pat. No. 9,890,210, Aug. 8, 2018, 93 pages.
*Eli Lilly and Company* v *Teva Pharmaceauticals International GMBH*, "Declaration of Andrew Charles, M.D.," Case No. IPR2018-01426, U.S. Pat. No. 9,890,211, Aug. 8, 2018, 100 pages.
*Eli Lilly and Company* v *Teva Pharmaceauticals International GMBH*, "Declaration of Andrew Charles, M.D.," Case No. IPR2018-01427, U.S. Pat. No. 8,597,649, Aug. 8, 2018, 94 pages.
*Eli Lilly and Company* v *Teva Pharmaceauticals International GMBH*, "Declaration of Dr. Andrew Charles," Case No. IPR2018-01712, U.S. Pat. No. 9,884,908, Oct. 1, 2018, 119 pages.
*Eli Lilly and Company* v *Teva Pharmaceauticals International GMBH*, "Declaration of Andrew Charles, M.D.," IPR2018-01710, U.S. Pat. No. 8,586,045 on Sep. 27, 2018, 113 pages.
*Eli Lilly and Company* v *Teva Pharmaceauticals International GMBH*, "Declaration of Dr. Alain P. Vasserot, Ph.D.," Case No. IPR2018-01711, U.S. Pat. No. 9,884,907, Sep. 27, 2018, 78 pages.
*Eli Lilly and Company* v *Teva Pharmaceauticals International GMBD*, "Declaration of Alain P. Vasserot," Case No. IPR2018-01710, U.S. Pat. No. 8,586,045 on Sep. 9, 2018, 86 pages.
*Eli Lilly and Company* v *Teva Pharmaceauticals International GMBH*, "Declaration of Alain P. Vasserot," Case No. IPR2018-01423, U.S. Pat. No. 9,266,951, Aug. 2018, 80 pages.
*Eli Lilly and Company* v *Teva Pharmaceauticals International GMBH*, "Declaration of Alain P. Vasserot," Case No. IPR2018-01424, U.S. Pat. No. 9,346,881, Aug. 2018, 85 pages.
*Eli Lilly and Company* v *Teva Pharmaceauticals International GMBH*, "Declaration of Alain P. Vasserot," Case No. IPR2018-01425, U.S. Pat. No. 9,890,210, Aug. 2018, 75 pages.
*Eli Lilly and Company* v *Teva Pharmaceauticals International GMBH*, "Declaration of Alain P. Vasserot," Case No. IPR2018-01426, U.S. Pat. No. 9,890,211, Aug. 2018, 93 pages.
*Eli Lilly and Company* v *Teva Pharmaceauticals International GMBH*, "Declaration of Alain P. Vasserot," Case No. IPR2018-01427, U.S. Pat. No. 8,597,649, Aug. 2018, 88 pages.
*Eli Lilly and Company* v *Teva Pharmaceauticals International GMBH.*, "Declaration of Alain P. Vasserot," Case No. IPR2018-01422, U.S. Pat. No. 9,340,614, Aug. 2018, 78 pages.
*Eli Lilly and Company* v *Teva Pharmaceauticals International GMBH*, "Declaration of Dr. Alain P. Vasserot," Case No. IPR2018-01712, U.S. Pat. No. 9,884,908, Sep. 27, 2018, 93 pages.
*Eli Lilly and Company* v *Teva Pharmaceauticals International GMBH*, "Petitioner's Exhibit List as of Oct. 1, 2018," Case No. IPR2018-01711, U.S. Pat. No. 9,884,907, Oct. 1, 2018, 20 pages.
*Eli Lilly and Company* v *Teva Pharmaceauticals International GMBH*, "Petitioner's Exhibit List as of Sep. 28, 2018," Case No. IPR2018-01710, U.S. Pat. No. 8,586,045 on Sep. 28, 2018, 21 pages.

(56) References Cited

OTHER PUBLICATIONS

*Eli Lilly and Company* v *Teva Pharmaceauticals International GMBH,* "Petitioner's Exhibit List as of Aug. 8, 2018," Case No. IPR2018-01425, U.S. Pat. No. 9,890,210, dated Aug. 8, 2018, 20 pages.
*Eli Lilly and Company* v *Teva Pharmaceauticals International GMBH,* "Petitioner's Exhibit List as of Aug. 8, 2018," Case No. IPR2018-01422, U.S. Pat. No. 9,340,614, dated Aug. 8, 2018, 20 pages.
*Eli Lilly and Company* v *Teva Pharmaceauticals International GMBH,* "Petitioner's Exhibit List as of Aug. 8, 2018," Case No. IPR2018-01423, U.S. Pat. No. 9,266,951, dated Aug. 8, 2018, 18 pages.
*Eli Lilly and Company* v *Teva Pharmaceauticals International GMBH,* "Petitioner's Exhibit List as of Aug. 8, 2018," Case No. IPR2018-01424, U.S. Pat. No. 9,346,881, dated Aug. 8, 2018, 19 pages.
*Eli Lilly and Company* v *Teva Pharmaceauticals International GMBH,* "Petitioner's Exhibit List as of Aug. 8, 2018," Case No. IPR2018-01426, U.S. Pat. No. 9,890,211, dated Aug. 8, 2018. 21 pages.
*Eli Lilly and Company* v *Teva Pharmaceauticals International GMBH,* "Petitioner's Exhibit List as of Aug. 8, 2018," Case No. IPR2018-01427, U.S. Pat. No. 8,597,649, dated Aug. 8, 2018, 19 pages.
*Eli Lilly and Company* v *Teva Pharmaceauticals International GMBH,* "Petitioner's Exhibit List of Oct. 1, 2018," Case No. IPR2018-01712, U.S. Pat. No. 9,884,908, Oct. 1, 2018, 21 pages.
*Eli Lilly and Company* v *Teva Pharmaceauticals International GMBH,* "Petition for Inter Parte Review," Case No. IPR2018-01711, U.S. Pat. No. 9,884,907, filed Oct. 1, 2018, 74 pages.
*Eli Lilly and Company* v *Teva Pharmaceauticals International GMBH,* "Petition for Inter Partes Review," Case No. IPR2018-01422, U.S. Pat. No. 9,340,614, dated Aug. 8, 2018, 71 pages.
*Eli Lilly and Company* v *Teva Pharmaceauticals International GMBH,* "Petition for Inter Partes Review," Case No. IPR2018-01423, U.S. Pat. No. 9,266,951, dated Aug. 8, 2018, 76 pages.
*Eli Lilly and Company* v *Teva Pharmaceauticals International GMBH,* "Petition for Inter Partes Review," Case No. IPR2018-01424, U.S. Pat. No. 9,346,881, dated Aug. 8, 2018, 78 pages.
*Eli Lilly and Company* v *Teva Pharmaceauticals International GMBH,* "Petition for Inter Partes Review," Case No. IPR2018-01425, U.S. Pat. No. 9,890,210, dated Aug. 8, 2018, 67 pages.
*Eli Lilly and Company* v *Teva Pharmaceauticals International GMBH,* "Petition for Inter Partes Review," Case No. IPR2018-01426, U.S. Pat. No. 9,890,211, dated Aug. 8, 2018, 77 pages.
*Eli Lilly and Company* v *Teva Pharmaceauticals International GMBH,* "Petition for Inter Partes Review," Case No. IPR2018-01427, U.S. Pat. No. 8,597,649, dated Aug. 8, 2018, 76 pages.
*Eli Lilly and Company* v *Teva Pharmaceauticals International GMBH,* "Petition for Inter Partes Review," Case No. IPR2018-01710, U.S. Pat. No. 8,586,045 on Sep. 28, 2018, 79 pages.
*Eli Lilly and Company* v *Teva Pharmaceauticals International GMBH,* "Petition for Inter Partes Review," Case No. IPR2018-01712, U.S. Pat. No. 9,884,908, Oct. 1, 2018, 79 pages.

NH2-<u>A</u>C<u>D</u>TATCVTHRLA<u>G</u>LLSRSGG<u>V</u>VK<u>N</u>NFVPT<u>N</u>VGS<u>K</u>AF-CONH2
Human α-CGRP (identical to *cynomolgus* α-CGRP)

NH2-<u>A</u>C<u>N</u>TATCVTHRLA<u>G</u>LLSRSGG<u>M</u>VK<u>S</u>NFVPT<u>N</u>VGS<u>K</u>AF-CONH2
Human β-CGRP (identical to *cynomolgus* β-CGRP)

NH2-<u>S</u>C<u>N</u>TATCVTHRLA<u>G</u>LLSRSGG<u>V</u>VK<u>D</u>NFVPT<u>N</u>VGS<u>E</u>AF-CONH2
Rat α-CGRP (identical to mouse and dog α-CGRP)

NH2-<u>S</u>C<u>N</u>TATCVTHRLA<u>G</u>LLSRSGG<u>V</u>VK<u>D</u>NFVPT<u>N</u>VGS<u>K</u>AF-CONH2
Rat β-CGRP

NH2-<u>S</u>C<u>N</u>TATCVTHRLA<u>D</u>LLSRSGG<u>V</u>LK<u>D</u>NFVPT<u>D</u>VGS<u>E</u>AF-CONH2
Mouse β-CGRP NH2-<u>G</u>C<u>N</u>TATCVTHRLA<u>G</u>LLSRSGG<u>M</u>VK<u>S</u>NFVPT<u>N</u>VGS<u>E</u>AF-CONH2
Rabbit CGRP

Figure 8

SEQUENCE LISTING

<160> NUMBER OF SEQ ID NOS: 35

<210> SEQ ID NO 1
<211> LENGTH: 122
<212> TYPE: PRT
<213> ORGANISM: Artificial sequence
<220> FEATURE:
<223> OTHER INFORMATION: Synthetic polypeptide, Antibody G1 heavy chain
      variable region <400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Ala Glu Ile Arg Ser Glu Ser Asp Ala Ser Ala Thr His Tyr Ala Glu
    50                  55                  60

Ala Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Leu Ala Tyr Phe Asp Tyr Gly Leu Ala Ile Gln Asn Tyr Trp
            100                 105                 110

```
Gly Gln Gly Thr Leu Val Thr Val Ser Ser
        115                 120
```

<210> SEQ ID NO 2
<211> LENGTH: 107
<212> TYPE: PRT
<213> ORGANISM: Artificial sequence
<220> FEATURE:
<223> OTHER INFORMATION: Synthetic polypeptide, Antibody G1 light chain
      variable region

<400> SEQUENCE: 2

```
Glu Ile Val Leu Thr Gln Ser Pro Ala Thr Leu Ser Leu Ser Pro Gly
1               5                   10                  15

Glu Arg Ala Thr Leu Ser Cys Lys Ala Ser Lys Arg Val Thr Thr Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Tyr Leu Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Ser Gln Ser Tyr Asn Tyr Pro Tyr
                85                  90                  95

Thr Phe Gly Gln Gly Thr Lys Leu Glu Ile Lys
            100                 105
```

<210> SEQ ID NO 3
<211> LENGTH: 10
<212> TYPE: PRT
<213> ORGANISM: Artificial sequence
<220> FEATURE:
<223> OTHER INFORMATION: Synthetic polypeptide, Antibody G1 CDR H1

<400> SEQUENCE: 3

```
Gly Phe Thr Phe Ser Asn Tyr Trp Ile Ser
1               5                   10
```

<210> SEQ ID NO 4
<211> LENGTH: 19
<212> TYPE: PRT
<213> ORGANISM: Artificial sequence
<220> FEATURE:
<223> OTHER INFORMATION: Synthetic polypeptide, Antibody G1 CDR H2

<400> SEQUENCE: 4

```
Glu Ile Arg Ser Glu Ser Asp Ala Ser Ala Thr His Tyr Ala Glu Ala
1               5                   10                  15

Val Lys Gly
```

<210> SEQ ID NO 5
<211> LENGTH: 11
<212> TYPE: PRT
<213> ORGANISM: Artificial sequence
<220> FEATURE:
<223> OTHER INFORMATION: Synthetic polypeptide, Antibody G1 CDR H3

<400> SEQUENCE: 5

```
Tyr Phe Asp Tyr Gly Leu Ala Ile Gln Asn Tyr
1               5                   10
```

<210> SEQ ID NO 6

```
<211> LENGTH: 11
<212> TYPE: PRT
<213> ORGANISM: Artificial sequence
<220> FEATURE:
<223> OTHER INFORMATION: Synthetic polypeptide, Antibody G1 CDR L1

<400> SEQUENCE: 6

Lys Ala Ser Lys Arg Val Thr Thr Tyr Val Ser
1               5                   10

<210> SEQ ID NO 7
<211> LENGTH: 7
<212> TYPE: PRT
<213> ORGANISM: Artificial sequence
<220> FEATURE:
<223> OTHER INFORMATION: Synthetic polypeptide, Antibody G1 CDR L2

<400> SEQUENCE: 7

Gly Ala Ser Asn Arg Tyr Leu
1               5

<210> SEQ ID NO 8
<211> LENGTH: 9
<212> TYPE: PRT
<213> ORGANISM: Artificial sequence
<220> FEATURE:
<223> OTHER INFORMATION: Synthetic polypeptide, Antibody G1 CDR L3

<400> SEQUENCE: 8

Ser Gln Ser Tyr Asn Tyr Pro Tyr Thr
1               5

<210> SEQ ID NO 9
<211> LENGTH: 366
<212> TYPE: DNA
<213> ORGANISM: Artificial sequence
<220> FEATURE:
<223> OTHER INFORMATION: Synthetic oligonucleotide, Antibody G1 heavy
      chain variable region

<400> SEQUENCE: 9
gaagttcagc tggttgaatc cggtggtggt ctggttcagc caggtggttc cctgcgtctg      60
tcctgcgctg cttccggttt caccttctcc aactactgga tctcctgggt tcgtcaggct     120
cctggtaaag gtctggaatg ggttgctgaa atccgttccg aatccgacgc gtccgctacc     180
cattacgctg aagctgttaa aggtcgtttc accatctccc gtgacaacgc taagaactcc     240
ctgtacctgc agatgaactc cctgcgtgct gaagacaccg ctgttttacta ctgcctggct     300 tactttgact acggtctggc tatccagaac tactggggtc agggtacccct ggttaccgtt     360 tcctcc                                                                  366

<210> SEQ ID NO 10
<211> LENGTH: 321
<212> TYPE: DNA
<213> ORGANISM: Artificial sequence
<220> FEATURE:
<223> OTHER INFORMATION: Synthetic oligonucleotide, Antibody G1 light
      chain variable region

<400> SEQUENCE: 10
gaaatcgttc tgacccagtc cccggctacc ctgtccctgt ccccaggtga acgtgctacc      60
ctgtcctgca aagcttccaa acgggttacc acctacgttt cctggtacca gcagaaaccc     120
ggtcaggctc ctcgtctgct gatctacggt gcttccaacc gttacctcgg tatcccagct     180
```

```
cgtttctccg gttccggttc cggtaccgac ttcaccctga ccatctcctc cctggaaccc    240
gaagacttcg ctgtttacta ctgcagtcag tcctacaact accccctacac cttcggtcag    300 ggtaccaaac tggaaatcaa a                                                321
```

<210> SEQ ID NO 11
<211> LENGTH: 448
<212> TYPE: PRT
<213> ORGANISM: Artificial sequence
<220> FEATURE:
<223> OTHER INFORMATION: Synthetic polypeptide, Antibody G1 heavy chain

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Ala Glu Ile Arg Ser Glu Ser Asp Ala Ser Ala Thr His Tyr Ala Glu
    50                  55                  60

Ala Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Leu Ala Tyr Phe Asp Tyr Gly Leu Ala Ile Gln Asn Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335
```

```
Ile Ser Lys Thr Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 12
<211> LENGTH: 214
<212> TYPE: PRT
<213> ORGANISM: Artificial sequence
<220> FEATURE:
<223> OTHER INFORMATION: Synthetic polypeptide, Antibody G1 light chain

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Lys Arg Val Thr Thr Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Tyr Leu Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Ser Gln Ser Tyr Asn Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 1347
<212> TYPE: DNA
<213> ORGANISM: Artificial sequence
<220> FEATURE:
```

<223> OTHER INFORMATION: Synthetic oligonucleotide, Antibody G1 heavy
      chain

<400> SEQUENCE: 13

| | |
|---|---|
| gaagttcagc tggttgaatc cggtggtggt ctggttcagc aggtggttc cctgcgtctg | 60 |
| tcctgcgctg cttccggttt caccttctcc aactactgga tctcctgggt tcgtcaggct | 120 |
| cctggtaaag gtctggaatg ggttgctgaa atccgttccg aatccgacgc gtccgctacc | 180 |
| cattacgctg aagctgttaa aggtcgtttc accatctccc gtgacaacgc taagaactcc | 240 |
| ctgtacctgc agatgaactc cctgcgtgct gaagacaccg ctgtttacta ctgcctggct | 300 |
| tactttgact acggtctggc tatccagaac tactggggtc agggtaccct ggttaccgtt | 360 |
| tcctccgcct ccaccaaggg cccatctgtc ttcccactgg ccccatgctc ccgcagcacc | 420 |
| tccgagagca gccgcccct gggctgcctg gtcaaggact acttcccaga acctgtgacc | 480 |
| gtgtcctgga actctggcgc tctgaccagc ggcgtgcaca ccttcccagc tgtcctgcag | 540 |
| tcctcaggtc tctactccct cagcagcgtg gtgaccgtgc catccagcaa cttcggcacc | 600 |
| cagacctaca cctgcaacgt agatcacaag ccaagcaaca ccaaggtcga caagaccgtg | 660 |
| gagagaaagt gttgtgtgga gtgtccacct tgtccagccc ctccagtggc cggaccatcc | 720 |
| gtgttcctgt tccctccaaa gccaaggac accctgatga tctccagaac cccagaggtg | 780 |
| acctgtgtgg tggtggacgt gtcccacgag acccagagg tgcagttcaa ctggtatgtg | 840 |
| gacggagtgg aggtgcacaa cgccaagacc aagccaagag aggagcagtt caactccacc | 900 |
| ttcagagtgg tgagcgtgct gaccgtggtg caccaggact ggctgaacgg aaaggagtat | 960 |
| aagtgtaagg tgtccaacaa gggactgcca tccagcatcg agaagaccat ctccaagacc | 1020 |
| aagggacagc caagagagcc acaggtgtat accctgcccc catccagaga ggagatgacc | 1080 |
| aagaaccagg tgtccctgac ctgtctggtg aagggattct atccatccga catcgccgtg | 1140 |
| gagtgggagt ccaacggaca gccagagaac aactataaga ccaccctcc aatgctggac | 1200 |
| tccgacggat ccttcttcct gtattccaag ctgaccgtgg acaagtccag atggcagcag | 1260 |
| ggaaacgtgt tctcttgttc cgtgatgcac gaggccctgc acaaccacta tacccagaag | 1320 |
| agcctgtccc tgtctccagg aaagtaa | 1347 |

<210> SEQ ID NO 14
<211> LENGTH: 645
<212> TYPE: DNA
<213> ORGANISM: Artificial sequence
<220> FEATURE:
<223> OTHER INFORMATION: Synthetic oligonucleotide, Antibody G1 light
      chain

<400> SEQUENCE: 14

| | |
|---|---|
| gaaatcgttc tgacccagtc cccggctacc ctgtccctgt ccccaggtga acgtgctacc | 60 |
| ctgtcctgca aagcttccaa acgggttacc acctacgttt cctggtacca gcagaaaccc | 120 |
| ggtcaggctc ctcgtctgct gatctacggt gcttccaacc gttacctcgg tatcccagct | 180 |
| cgtttctccg gttccggttc cggtaccgac ttcaccctga ccatctcctc cctggaaccc | 240 |
| gaagacttcg ctgtttacta ctgcagtcag tcctacaact ccccctacac cttcggtcag | 300 |
| ggtaccaaac tggaaatcaa acgcactgtg gctgcaccat ctgtcttcat cttccctcca | 360 |
| tctgatgagc agttgaaatc cggaactgcc tctgttgtgt gcctgctgaa taacttctat | 420 |
| ccgcgcgagg ccaaagtaca gtggaaggtg gataacgccc tccaatcgg taactcccag | 480 |
| gagagtgtca cagagcagga cagcaaggac agcacctaca gcctcagcag cacctgacc | 540 |

```
ctgagcaaag cagactacga gaaacacaaa gtctacgcct gcgaagtcac ccatcagggc    600
ctgagttctc cagtcacaaa gagcttcaac cgcggtgagt gctaa                   645
```

<210> SEQ ID NO 15
<211> LENGTH: 37
<212> TYPE: PRT
<213> ORGANISM: Homo sapiens
<220> FEATURE:
<223> OTHER INFORMATION: Polypeptide, Alpha-CGRP
<400> SEQUENCE: 15

```
Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35
```

<210> SEQ ID NO 16
<211> LENGTH: 37
<212> TYPE: PRT
<213> ORGANISM: Homo sapiens
<220> FEATURE:
<223> OTHER INFORMATION: Polypeptide, Beta-CGRP
<400> SEQUENCE: 16

```
Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Ala Phe
        35
```

<210> SEQ ID NO 17
<211> LENGTH: 37
<212> TYPE: PRT
<213> ORGANISM: Rattus norvegicus
<220> FEATURE:
<223> OTHER INFORMATION: Polypeptide, Alpha-CGRP
<400> SEQUENCE: 17

```
Ser Cys Asn Thr Ala Thr Cys Val Thr His Arg Leu Ala Gly Leu Leu
1               5                   10                  15

Ser Arg Ser Gly Gly Val Val Lys Asp Asn Phe Val Pro Thr Asn Val
            20                  25                  30

Gly Ser Glu Ala Phe
        35
```

<210> SEQ ID NO 18
<211> LENGTH: 37
<212> TYPE: PRT
<213> ORGANISM: Rattus norvegicus
<220> FEATURE:
<223> OTHER INFORMATION: Polypeptide, Beta-CGRP
<400> SEQUENCE: 18

```
Ser Cys Asn Thr Ala Thr Cys Val Thr His Arg Leu Ala Gly Leu Leu
1               5                   10                  15

Ser Arg Ser Gly Gly Val Val Lys Asp Asn Phe Val Pro Thr Asn Val
            20                  25                  30

Gly Ser Lys Ala Phe
```

```
<210> SEQ ID NO 19
<211> LENGTH: 115
<212> TYPE: PRT
<213> ORGANISM: Artificial sequence
<220> FEATURE:
<223> OTHER INFORMATION: Synthetic polypeptide, Antibody G2 heavy chain
      variable region

<400> SEQUENCE: 19

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Ser
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Lys Gly Gly Asn Asp Gly Tyr Trp Gly Gln Gly Thr Thr Leu Thr
            100                 105                 110

Val Ser Ser
        115

<210> SEQ ID NO 20
<211> LENGTH: 108
<212> TYPE: PRT
<213> ORGANISM: Artificial sequence
<220> FEATURE:
<223> OTHER INFORMATION: Synthetic polypeptide, Antibody G2 light chain
      variable region

<400> SEQUENCE: 20

Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Ile
            20                  25                  30

Tyr Leu His Trp Tyr Gln Gln Lys Pro Gly Phe Ser Pro Lys Val Leu
        35                  40                  45

Ile Tyr Arg Ala Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Thr Ile Pro
                85                  90                  95

Phe Thr Phe Gly Ser Gly Thr Lys Leu Glu Ile Lys
            100                 105

<210> SEQ ID NO 21
<211> LENGTH: 5
<212> TYPE: PRT
<213> ORGANISM: Artificial sequence
<220> FEATURE:
<223> OTHER INFORMATION: Synthetic polypeptide, Antibody G2 CDR H1

<400> SEQUENCE: 21
```

```
Ser Ser Val Met His
1               5

<210> SEQ ID NO 22
<211> LENGTH: 17
<212> TYPE: PRT
<213> ORGANISM: Artificial sequence
<220> FEATURE:
<223> OTHER INFORMATION: Synthetic polypeptide, Antibody G2 CDR H2

<400> SEQUENCE: 22

Tyr Ile Asn Pro Tyr Asn Asp Gly Thr Lys Tyr Asn Glu Lys Phe Lys
1               5                   10                  15

Gly

<210> SEQ ID NO 23
<211> LENGTH: 6
<212> TYPE: PRT
<213> ORGANISM: Artificial sequence
<220> FEATURE:
<223> OTHER INFORMATION: Synthetic polypeptide, Antibody G2 CDR H3

<400> SEQUENCE: 23

Gly Gly Asn Asp Gly Tyr
1               5

<210> SEQ ID NO 24
<211> LENGTH: 12
<212> TYPE: PRT
<213> ORGANISM: Artificial sequence
<220> FEATURE:
<223> OTHER INFORMATION: Synthetic polypeptide, Antibody G2 CDR L1

<400> SEQUENCE: 24

Ser Ala Ser Ser Ser Ile Ser Ser Ile Tyr Leu His
1               5                   10

<210> SEQ ID NO 25
<211> LENGTH: 7
<212> TYPE: PRT
<213> ORGANISM: Artificial sequence
<220> FEATURE:
<223> OTHER INFORMATION: Synthetic polypeptide, Antibody G2 CDR L2

<400> SEQUENCE: 25

Arg Ala Ser Asn Leu Ala Ser
1               5

<210> SEQ ID NO 26
<211> LENGTH: 9
<212> TYPE: PRT
<213> ORGANISM: Artificial sequence
<220> FEATURE:
<223> OTHER INFORMATION: Synthetic polypeptide, Antibody G2 CDR L3

<400> SEQUENCE: 26

Gln Gln Gly Ser Thr Ile Pro Phe Thr
1               5

<210> SEQ ID NO 27
<211> LENGTH: 345
<212> TYPE: DNA
<213> ORGANISM: Artificial sequence
<220> FEATURE:
<223> OTHER INFORMATION: Synthetic oligonucleotide, Antibody G2 heavy
      chain variable region
```

-continued

```
<400> SEQUENCE: 27
gaggtccagc tgcagcagtc tggacctgag ctggtaaagc ctggggcttc agtgaagatg      60
tcctgcaagg cttctggata cacattcact agctctgtta tgcactgggt gaagcagaag     120
cctgggcagg gccttgagtg gattggatat attaatcctt acaatgatgg tactaagtac     180
aatgagaagt tcaaaggcaa ggccacactg acttcagaca atcctccag cacagcctac      240 atggaactca gcagcctgac ctctgaggac tctgcggtct attactgtgc aaaagggggt     300
aacgatggct actggggcca aggcactact ctcacagtct cctca                     345

<210> SEQ ID NO 28
<211> LENGTH: 324
<212> TYPE: DNA
<213> ORGANISM: Artificial sequence
<220> FEATURE:
<223> OTHER INFORMATION: Synthetic oligonucleotide, Antibody G2 light
      chain variable region

<400> SEQUENCE: 28
gaaattgtgc tcacccagtc tccaaccacc atggctgcat ctcccgggga agatcact       60 atcacctgta gtgccagctc aagtataagt tccatttact tgcattggta tcagcagaag    120
ccaggattct cccctaaagt cttgatttat agggcatcca atctggcttc tggagtccca    180
gctcgcttca gtggcagtgg gtctgggacc tcttactctc tcacaattgg caccatggag    240
gctgaagatg ttgccactta ctactgccag cagggtagta ctataccatt cacgttcggc    300
tcggggacaa agttggaaat aaaa                                           324

<210> SEQ ID NO 29
<211> LENGTH: 216
<212> TYPE: PRT
<213> ORGANISM: Artificial sequence
<220> FEATURE:
<223> OTHER INFORMATION: Synthetic polypeptide, Antibody G2 heavy chain

<400> SEQUENCE: 29

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Ser
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Lys Gly Gly Asn Asp Gly Tyr Trp Gly Gln Gly Thr Thr Leu Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175
```

Tyr Thr Leu Ser Ser Val Thr Val Pro Ser Ser Thr Trp Pro Ser
            180                 185                 190

Glu Thr Val Thr Cys Asn Val Ala His Pro Ala Ser Ser Thr Lys Val
        195                 200                 205

Asp Lys Lys Ile Val Pro Arg Asp
    210                 215

<210> SEQ ID NO 30
<211> LENGTH: 215
<212> TYPE: PRT
<213> ORGANISM: Artificial sequence
<220> FEATURE:
<223> OTHER INFORMATION: Synthetic polypeptide, Antibody G2 light chain

<400> SEQUENCE: 30

Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ile Ser Ser Ile
            20                  25                  30

Tyr Leu His Trp Tyr Gln Gln Lys Pro Gly Phe Ser Pro Lys Val Leu
        35                  40                  45

Ile Tyr Arg Ala Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Thr Ile Pro
                85                  90                  95

Phe Thr Phe Gly Ser Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Arg Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215

<210> SEQ ID NO 31
<211> LENGTH: 648
<212> TYPE: DNA
<213> ORGANISM: Artificial sequence
<220> FEATURE:
<223> OTHER INFORMATION: Synthetic oligonucleotide, Antibody G2 heavy
      chain

<400> SEQUENCE: 31
gaggtccagc tgcagcagtc tggacctgag ctggtaaagc ctggggcttc agtgaagatg      60
tcctgcaagg cttctggata cacattcact agctctgtta tgcactgggt gaagcagaag     120
cctgggcagg gccttgagtg gattggatat attaatcctt acaatgatgg tactaagtac     180

```
aatgagaagt tcaaaggcaa ggccacactg acttcagaca atcctccag cacagcctac      240 atggaactca gcagcctgac ctctgaggac tctgcggtct attactgtgc aaaagggggt      300
aacgatggct actggggcca aggcactact ctcacagtct cctcagccaa aacgacaccc      360
ccatctgtct atccactggc ccctggatct gctgcccaaa ctaactccat ggtgaccctg      420
ggatgcctgg tcaagggcta tttccctgag ccagtgacag tgacctggaa ctctggatcc      480
ctgtccagcg gtgtgcacac cttcccagct gtcctgcagt ctgacctcta cactctgagc      540
agctcagtga ctgtcccctc cagcacctgg cccagcgaga ccgtcacctg caacgttgcc      600
cacccggcca gcagcaccaa ggtggacaag aaaattgtgc ccagggat                  648

<210> SEQ ID NO 32
<211> LENGTH: 648
<212> TYPE: DNA
<213> ORGANISM: Artificial sequence
<220> FEATURE:
<223> OTHER INFORMATION: Synthetic oligonucleotide, Antibody G2 light
      chain

<400> SEQUENCE: 32
gaaattgtgc tcacccagtc tccaaccacc atggctgcat ctcccgggga agatcact       60 atcacctgta gtgccagctc aagtataagt tccatttact tgcattggta tcagcagaag      120
ccaggattct cccctaaagt cttgatttat agggcatcca atctggcttc tggagtccca      180
gctcgcttca gtggcagtgg gtctgggacc tcttactctc tcacaattgg caccatggag      240
gctgaagatg ttgccactta ctactgccag cagggtagta ctataccatt cacgttcggc      300
tcggggacaa agttggaaat aaaacgggct gatgctgcac caactgtatc catcttccca      360
ccatccagtg agcagttaac atctggaggt gcctcagtcg tgtgcttctt gaacaacttc      420
taccccagag acatcaatgt caagtggaag attgatggca gtgaacgaca aaatggtgtc      480
ctgaacagtt ggactgatca ggacagcaaa gacagcacct acagcatgag cagcaccctc      540
acattgacca aggacgagta tgaacgacat aacagctata cctgtgaggc cactcacaag      600
acatcaactt cacccatcgt caagagcttc aacaggaatg agtgttaa                 648

<210> SEQ ID NO 33
<211> LENGTH: 5
<212> TYPE: PRT
<213> ORGANISM: Homo sapiens

<400> SEQUENCE: 33

Gly Ser Lys Ala Phe
1               5

<210> SEQ ID NO 34
<211> LENGTH: 37
<212> TYPE: PRT
<213> ORGANISM: Mus musculus

<400> SEQUENCE: 34

Ser Cys Asn Thr Ala Thr Cys Val Thr His Arg Leu Ala Asp Leu Leu
1               5                   10                  15

Ser Arg Ser Gly Gly Val Leu Lys Asp Asn Phe Val Pro Thr Asp Val
            20                  25                  30

Gly Ser Glu Ala Phe
        35

<210> SEQ ID NO 35
```

```
<211> LENGTH: 37
<212> TYPE: PRT
<213> ORGANISM: Oryctolagus cuniculus

<400> SEQUENCE: 35

Gly Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Glu Ala Phe
            35
```

METHODS OF TREATING FIBROMYALGIA

This application is a continuation of U.S. patent application Ser. No. 15/341,610 filed on Nov. 2, 2016, which is a continuation of U.S. patent application Ser. No. 15/081,681 filed on Mar. 25, 2016 (now abandoned), which is a continuation of U.S. patent application Ser. No. 14/612,110 filed on Feb. 2, 2015 (now U.S. Pat. No. 9,328,167), which is a continuation of U.S. patent application Ser. No. 13/892,121 filed on May 10, 2013 (now abandoned), which is a continuation of U.S. patent application Ser. No. 13/623,206 filed on Sep. 20, 2012 (now abandoned), which is a divisional of U.S. patent application Ser. No. 12/920,621 filed on Sep. 2, 2010 (now U.S. Pat. No. 8,293,239), which is a National Stage Application under 35 U.S.C. § 371 of PCT/IB2009/050852, filed on Mar. 3, 2009, which claims the benefit of U.S. Provisional Patent Application No. 61/033,558, filed on Mar. 4, 2008.

REFERENCE TO SEQUENCE LISTING

The instant application contains a Sequence Listing which has been submitted in ASCII format via EFS-Web and is hereby incorporated by reference in its entirety. The sequence listing contains no new matter. Said ASCII copy, created on May 1, 2018, is named Sequence_Listing.txt and is 28 kilobytes in size.

FIELD OF THE INVENTION

The invention relates to an anti-CGRP antibody for use in the prevention and/or treatment of chronic pain and/or symptoms of chronic pain, and to a method of treating and/or preventing chronic pain and/or symptoms of chronic pain using an anti-CGRP antibody.

BACKGROUND OF THE INVENTION

Chronic pain is a long lasting pain that persists longer than the temporal course of natural healing of the underlying causative injury or disease. It serves no beneficial or protective function and an estimated 2.7 million people in the UK are invalided due to chronic pain conditions.

Cancer pain is one of the most common types of chronic pain and demonstrates nociceptive components due to tumour growth and neuropathic components due to tumour induced nerve damage. It further involves structural damage, nerve entrapment and damage, inflammatory processes which lead to the disruption of normal tissue metabolism, the production of inflammatory prostaglandins and cytokines, and tissue damage.

To date, the main analgesics employed for treatment of chronic pain are opiates and non-steroidal anti-inflammatory drugs (NSAIDS). Both classes of drugs can produce severe side-effects; NSAIDS can cause gastric ulceration and renal damage, opiates can cause nausea, constipation, confusion and dependency problems. Opioids fail to produce pain relief in all individuals suffering chronic pain, even at high doses and development of analgesic resistance to opioids complicates their utility for long term therapy. In particular cancer pain treatment requires the use of unacceptably high levels of opiates bringing with it side-effects and at least 20% of treated patients still have uncontrolled pain.

Accordingly, there is a critical medical need to identify new pharmaceutically active compounds that interfere with key steps of the chronic pain process and particularly for the treatment and/or prevention of chronic nociceptive pain and/or symptoms of chronic nociceptive pain.

Surprisingly we have found that administration of an anti-CGRP antibody is effective, with a peripheral site of action, in the prevention and/or treatment of chronic pain and in particular chronic nociceptive pain such as cancer pain.

CGRP (calcitonin gene-related peptide) is a 37 amino acid neuropeptide which acts as a neurotransmitter in the central nervous system. It binds with high affinity to the CGRP receptor, Calcitonin receptor-like receptor (CRLR), activating adenylate cyclase and protein kinase A production.

Centrally penetrating spinally administered, small molecule selective CGRP antagonists have been shown to be useful in the treatment of neuropathic and nociceptive pain conditions (Adwanikar et al, Pain 2007) suggesting that removal of endogenous CGRP in the spinal cord has an antinociceptive effect. Additionally intrathecal administration of antiserum against CGRP has been shown to reduce nociceptive behaviour in rodent models of arthritis (Kuraishi, Y., et. al Neurosci. lett (1998) 92, 325-329).

Surprisingly we have found that administration of an anti-CGRP antibody is effective, with a peripheral site of action, in the prevention and/or treatment of chronic pain and in particular chronic nociceptive pain when administered peripherally. This peripheral administration route provides a distinct advantage over the requirement to administer antibodies intrathecally or spinally, a more high risk and inconvenient procedure.

BRIEF DESCRIPTION OF THE INVENTION

The present invention provides the use of an anti-CGRP antagonist antibody for the manufacture of a medicament for the prevention and/or treatment of chronic pain and/or symptoms of chronic pain, wherein the medicament is prepared to be peripherally administered.

The present invention further provides a method of prevention and/or treatment of chronic pain and/or symptoms of chronic pain, in an individual, which comprises peripherally administering to said individual a therapeutically effective amount of an anti-CGRP antagonist antibody.

In one embodiment, the anti-CGRP antagonist antibody acts peripherally on administration.

Figure 4:
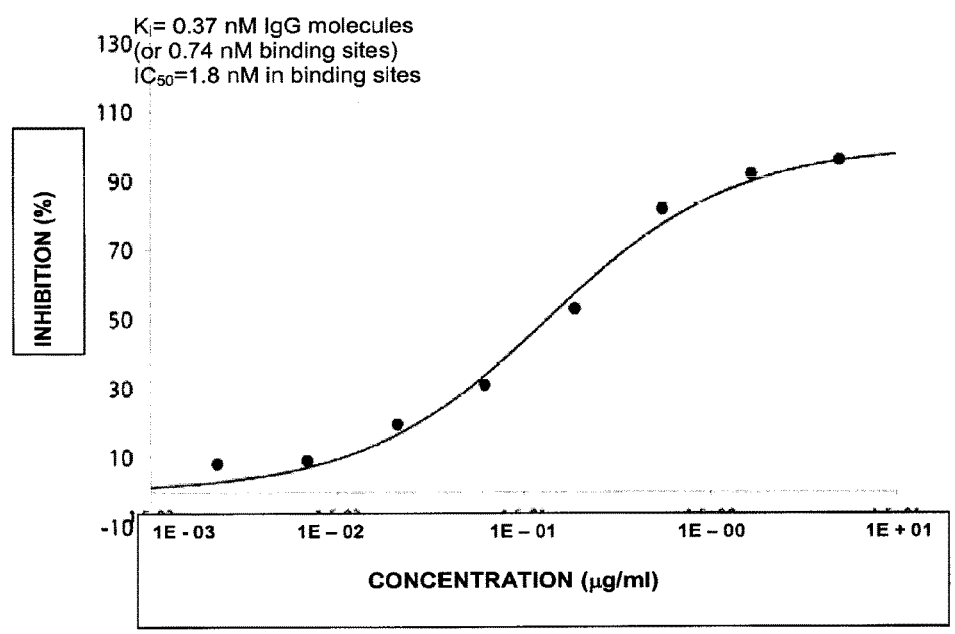

FIG. 4: Binding assay data demonstrating antibody G1 inhibits the binding of α-CGRP to the CGRP1 receptor.

Figure 5A:
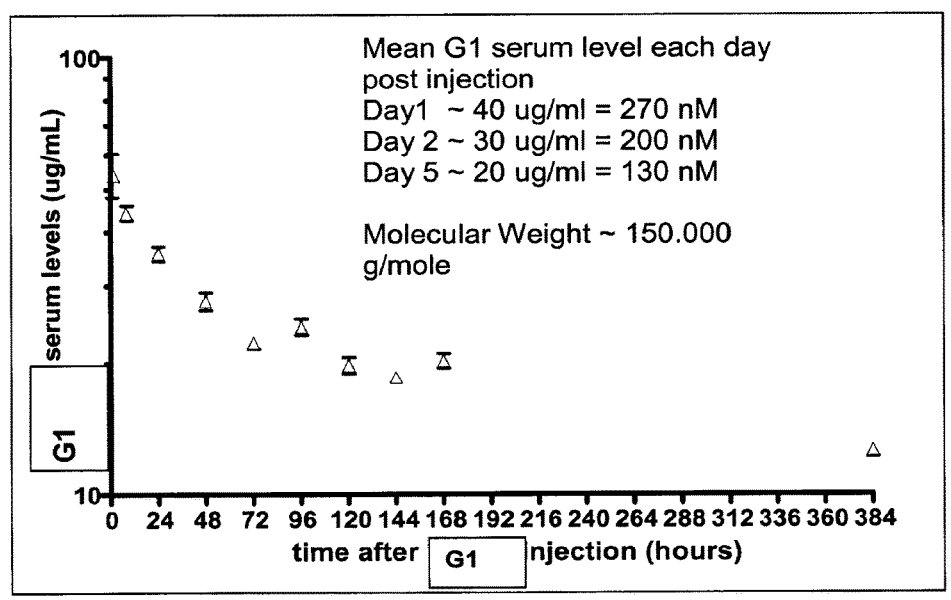

FIG. 5a: serum level of anti-CGRP concentration (ug/ml) vs time after IV administration of 10 mg/kg, measured by anti-IgG ELISA.

Figure 5B:
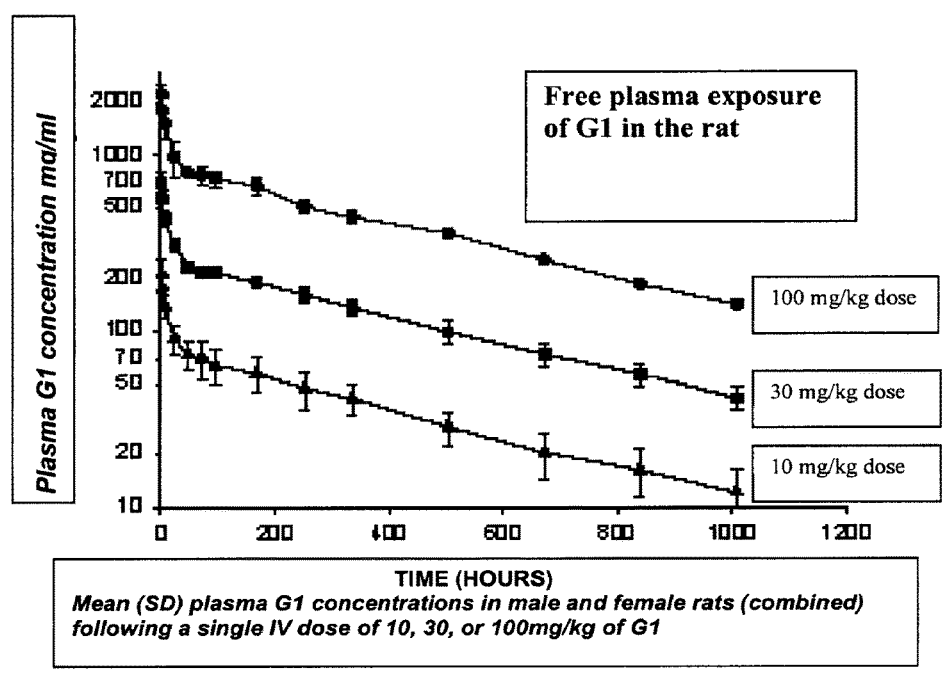

FIG. 5b: serum level of anti-CGRP concentration (ug/ml) vs time after IV administration of 10, 30, 100 mg/kg, measured by anti-IgG ELISA.

Figure 6:
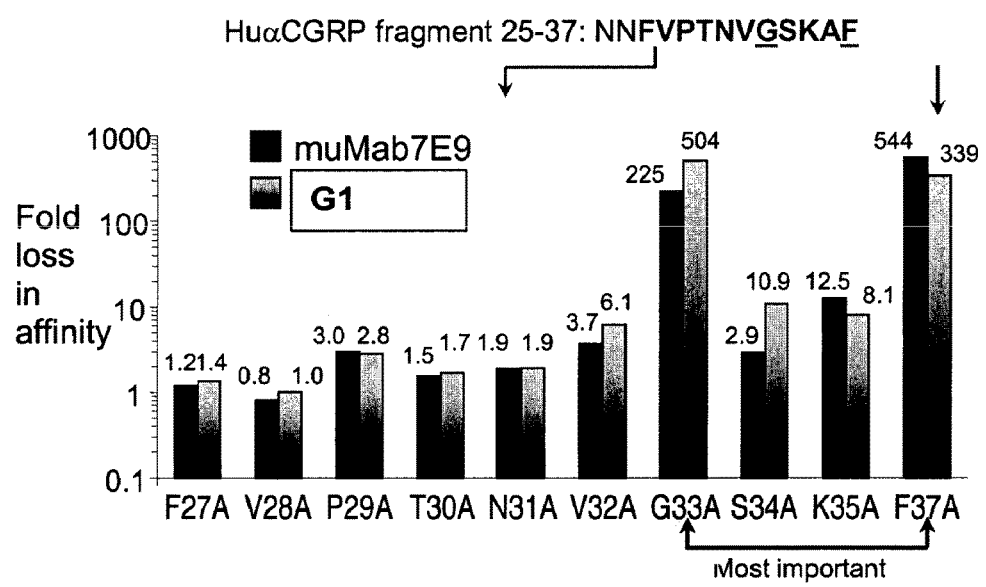

FIG. 6 Alanine scan using a C-terminal CGRP fragment (CGRP 25-37; residues 25-37 of SEQ ID NO: 15). The change in affinity is expressed in fold loss of affinity and which shows that anti-CGRP antibody G1 binds to the C-terminal region of human α-CGRP.

Figure 7:
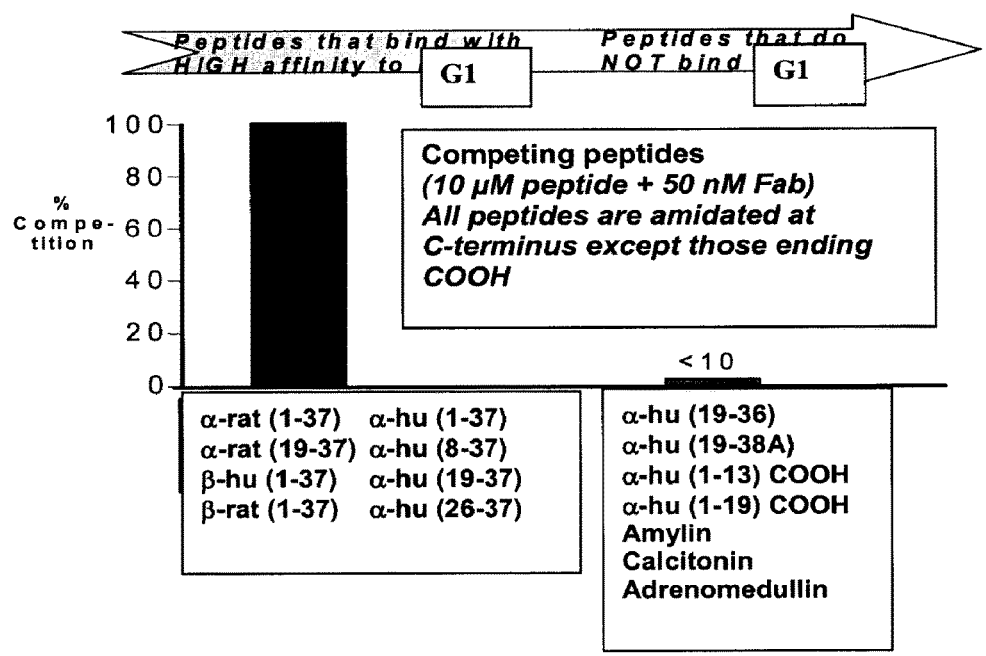

FIG. 7: Solution competition by Biacore: CGRP, CGRP fragments or peptides related in sequence to CGRP were used to determine the specificity of antibody G1.

FIG. 8: CGRP sequences from human, cynomolgus monkey, rat, mouse, dog and rabbit. Non-conserved residues between species are underlined, the epitope of antibody G1 is in bold (SEQ ID NO: 15, 16, 17, 18, and 34-35, respectively, in order of appearance).

Figure 9:
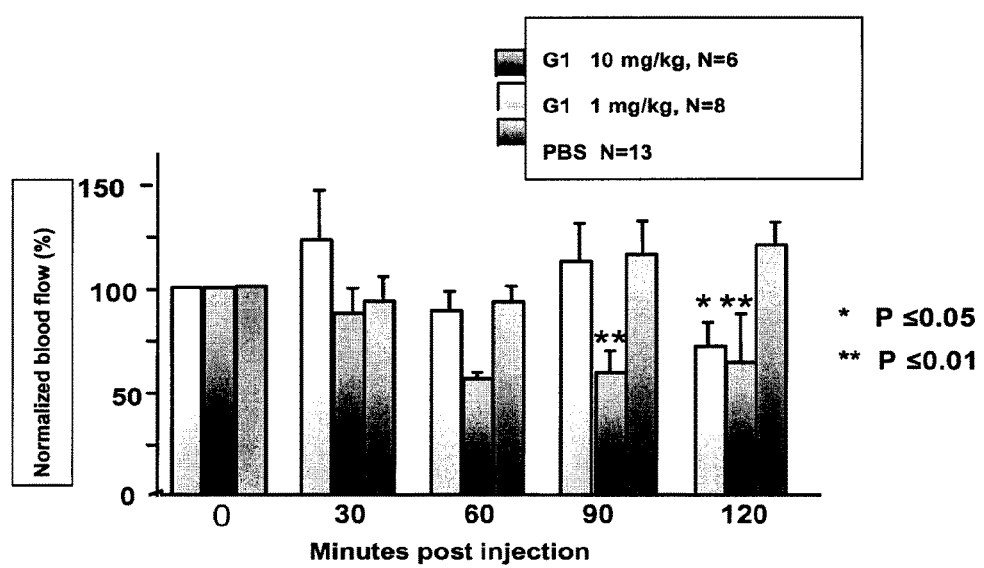

FIG. 9: Data showing G1 inhibits neurogenic flare in the skin starting from 90 min post-treatment. G1 was administered by intravenous administration (1 ml/kg). Data are from 6-8 or 13 rats per group. *p=0.05, **p=0.01 vs vehicle (phosphate buffered saline) treated group at each time point (AVOVA).

Table 1: Kd and IC50 of anti-CGRP antibodies measured at 25° C. against human α-CGRP [muMab7E9=murine precursor of G1. Its $K_D$ for rat β-CGRP=1 nM. RN4901=murine tool, recognising same epitope as G1 but showed same affinities and selectivity in rats (β-CGRP $K_D$=17 nM); G1=antibody humanized from muMab7E9 ($K_D$ for rat β-CGRP=0.1 nM).]

Table 2: G1 binding affinities as determined by Biacore

DESCRIPTION OF THE INVENTION

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

Definitions

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv, dAb), single chain antibodies (ScFv), mutants thereof, chimeric antibodies, diabodies, fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

"Fv" is an antibody fragment that contains a complete antigen-recognition and -binding site. In a two-chain Fv species, this region consists of a dimer of one heavy and one light chain variable domain in tight, non-covalent association. In a single-chain Fv species, one heavy and one light chain variable domain can be covalently linked by a flexible peptide linker such that the light and heavy chains can associate in a dimeric structure analogous to that in a two-chain Fv species. It is in this configuration that the three CDRs of each variable domain interact to define an antigen-binding specificity on the surface of the VH-VL dimer. However, even a single variable domain (or half of a Fv comprising only 3 CDRs specific for an antigen) has the ability to recognize and bind antigen, although generally at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge regions. A F(ab)2 fragment is a bivalent fragment comprising two Fab fragments linked by a disulfide bridge at the hinge region.

An antibody can have one or more binding sites (for combining with antigen). If there is more than one binding site, the binding sites may be identical to one another or may be different. For instance, a naturally-occurring immunoglobulin has two identical binding sites, a single chain antibody or Fab fragment has one binding site, while a "bispecific" or "bifunctional" antibody (diabody) has two different binding sites, in terms of sequence and/or antigen/epitope recognition.

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature.

A "monoclonal antibody" refers to a homogeneous antibody population wherein the monoclonal antibody is comprised of amino acids (naturally occurring and non-naturally occurring) that are involved in the selective binding of an antigen. A population of monoclonal antibodies is highly specific, being directed against a single antigenic site.

The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.).

As used herein, "humanized" antibodies refer to forms of non-human (e.g. murine) antibodies that are specific chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and .biological activity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or has been made using any of the techniques for making human antibodies known in the art or disclosed herein.

This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, PNAS, (USA) 95:6157-6162; Hoogenboom and Winter, 1991, J. Mol. Biol., 227:381; Marks et al., 1991, J. Mol. Biol., 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373.

A single chain antibody (scFc) is an antibody in which VL and VH regions are paired to form a monovalent molecule via a synthetic linker that enables them to be made as a single protein chain (Bird et al Science, 242: 423-426 (1988) and Huston et al., Proc. Natl. Acad. Sci. USA, 85:5879-5883 (1988)).

Diabodies are bivalent, bispecific antibodies in which VH and VL domains are expressed on a single polypeptide chain, but using a linker that is tooshort to allow for pairing between the two domains on the same chain, thereby forcing the domains to pair with complementary domains of another chain and creating two antigen binding sites.

"Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non-human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example.

A "functional Fc region" possesses at least one effector function of a native sequence Fc region. Exemplary "effector functions" include C1q binding; complement dependent cytotoxicity (CDC); Fc receptor binding; antibody-dependent cell-mediated cytotoxicity (ADCC); phagocytosis; down-regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

As used herein "antibody-dependent cell-mediated cytotoxicity" and "ADCC" refer to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998, PNAS (USA), 95:652-656.

As used herein, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods, 202:163 (1996), may be performed.

As used herein, the terms "G1" and "antibody G1" are used interchangeably to refer to an antibody produced by the expression vectors having deposit numbers ATCC-PTA-6867 and ATCC-PTA-6866. The amino acid sequence of the heavy chain and light chain variable regions are shown in SEQ ID Nos. 1 and 2. The CDR portions of antibody G1 (including Chothia and Kabat CDRs) are diagrammatically depicted in FIG. 5 of WO2007/054809, the content of which is herein incorporated by reference in its entirety. The polynucleotides encoding the heavy and light chain variable regions are shown in SEQ ID Nos. 9 and 10. The characterization of antibody G1 is described in the Examples of WO2007/054809, the entire content of which is herein incorporated by reference. G1 is a humanized monoclonal blocking antibody (IgG2) which blocks binding and activity of the neuropeptide CGRP (a and b) and its effect of neurogenic vasodilatation caused by CGRP release. G1 is an IgG2Δa monoclonal anti-CGRP antagonist antibody derived from the murine anti-CGRP antagonist antibody precursor, denoted muMAb7E9 as identified in a screen using spleen cells prepared from a mouse immunized with human and rat CGRP that were fused with murine plasmacytoma cells. G1 was created by grafting the muMAb 7E9 derived CDRs of light and heavy chain into the closest human germ line sequence followed by the introduction of at least 1 mutation into each CDR and 2 framework mutations in $V_H$. Two mutations were introduced into the Fc domain of G1 to suppress human Fc-receptor activation. G1 and muMab7E9 have been shown to recognise the same epitope.

As used herein, the terms "G2" and "antibody G2" are used interchangeably to refer to an anti-rat CGRP mouse monoclonal antibody as described in Wong H C et al. Hybridoma 12:93-106 (1993). The amino acid sequence of the heavy chain and light chain variable regions are shown in SEQ ID Nos. 19 and 20. The polynucleotides encoding the heavy and light chain variable regions are shown in SEQ ID Nos. 27 and 28. The CDR portions of antibody G2 are provided in SEQ ID Nos. 21 to 26. G2 has been shown to recognise the same epitope as G1.

As used herein, "immunospecific" binding of antibodies refers to the antigen specific binding interaction that occurs between the antigen-combining site of an antibody and the specific antigen recognized by that antibody (i.e., the antibody reacts with the protein in an ELISA or other immunoassay, and does not react detectably with unrelated proteins).

An epitope that "specifically binds", or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Chothia et al. (1989) Nature 342:877; Al-lazikani et al (1997) J. Molec. Biol. 273:927-948)). As used herein, a CDR may refer to CDRs defined by either approach or by a combination of both approaches.

A "constant region" of an antibody refers to the constant region of the antibody light chain or the constant region of the antibody heavy chain, either alone or in combination.

As used herein, an "anti-CGRP antagonist antibody" (interchangeably termed "anti-CGRP antibody") refers to an antibody which is able to bind to CGRP and inhibit CGRP biological activity and/or downstream pathway(s). An anti-CGRP antagonist antibody encompasses antibodies that block, antagonize, suppress or reduce (including significantly) CGRP biological activity. For purpose of the present invention, it will be explicitly understood that the term "anti-CGRP antagonist antibody" encompass all the previously identified terms, titles, and functional states and characteristics whereby the CGRP itself, a CGRP biological activity, or the consequences of the biological activity, are substantially nullified, decreased, or neutralized in any meaningful degree.

Examples of anti-CGRP antagonist antibodies are provided herein.

As used herein, "substantially pure" refers to material which is at least 50% pure (i.e., free from contaminants), more preferably at least 90% pure, more preferably at least 95% pure, more preferably at least 98% pure, more preferably at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "treatment" is an approach for obtaining beneficial or desired clinical results. For purposes of this invention, beneficial or desired clinical results include, but are not limited to, one or more of the following: improvement or alleviation of any aspect of chronic pain and/or symptom of chronic pain. For purposes of this invention, beneficial or desired clinical results include, but are not limited to, one or more of the following: including lessening severity, alleviation of pain and/or a symptom associated with chronic pain.

An "effective amount" of drug, compound, or pharmaceutical composition is an amount sufficient to effect beneficial or desired results including clinical results such as alleviation or reduction in pain sensation. An effective amount can be administered in one or more administrations. For purposes of this invention, an effective amount of drug, compound, or pharmaceutical composition is an amount sufficient to treat, ameliorate, reduce the intensity of and/or prevent chronic pain or symptom associated with chronic pain. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

In one embodiment, "prepared for" herein means the medicament is in the form of a dosage unit or the like suitably packaged and/or marked for use in peripheral administration.

"Reducing incidence" of chronic pain and/or a symptom associated with chronic pain means any of reducing severity (which can include reducing need for and/or amount of (e.g., exposure to) other drugs and/or therapies generally used for these conditions), duration, and/or frequency.

"Ameliorating" chronic pain and/or a symptom associated with chronic pain means a lessening or improvement of one or more symptoms of chronic pain and/or symptoms associated with chronic pain as compared to not administering an anti-CGRP antagonist antibody. "Ameliorating" also includes shortening or reduction in duration of a symptom.

"Palliating" chronic pain and/or a symptom associated with chronic pain means lessening the extent of one or more undesirable clinical manifestations of chronic pain in an individual or population of individuals treated with an anti-CGRP antagonist antibody in accordance with the invention.

As used therein, "delaying" the development of chronic pain means to defer, hinder, slow, retard, stabilize, and/or postpone progression of chronic pain and/or a symptom associated with chronic pain. This delay can be of varying lengths of time, depending on the history of the disease and/or individuals being treated. As is evident to one skilled in the art, a sufficient or significant delay can, in effect, encompass prevention, in that the individual does not develop chronic pain. A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

An "individual" or "subject" is a vertebrate, preferably a mammal, more preferably a human. Mammals include, but are not limited to, farm animals (such as cows), sport animals, pets (such as cats, dogs and horses), primates, mice and rats.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "peripherally administered" as used herein refers to the route by which the a substance, medicament and/or anti-CGRP antagonist antibody is to be delivered, in particular it means not centrally, not spinally, not intrathecally, not delivered directly into the CNS. The term refers to administration routes other than those immediately forgoing and includes via a route which is oral, sublingual, buccal, topical, rectal, via inhalation, transdermal, subcutaneous, intravenous, intra-arterial, intramuscular, intracardiac, intraosseous, intradermal, intraperitoneal, transmucosal, vaginal, intravitreal, intra-articular, peri-articular, local or epicutaneous.

The term "acts peripherally" as used herein refers to the site of action of a substance, compound, medicament and/or anti-CGRP antagonist antibody said site being within the peripheral nervous system as opposed to the central nervous system, said compound, medicament and/or anti-CGRP antagonist antibody said being limited by inability to cross the barrier to the CNS and brain when peripherally administered. The term "centrally penetrating" refers to the ability of a substance to cross the barrier to the brain or CNS.

The term "$K_{off}$", as used herein, is intended to refer to the off rate constant for dissociation of an antibody from the antibody/antigen complex.

The term "$K_d$", as used herein, is intended to refer to the dissociation constant of an antibody-antigen interaction.

The present invention is directed to a medicament for the prevention and/or treatment of chronic pain and/or symptoms of chronic pain and methods for prevention and/or treatment of chronic pain and/or symptoms of chronic pain in an individual.

In a first aspect, the invention provides the use of an anti-CGRP antagonist antibody for the manufacture of a medicament for the prevention and/or treatment of chronic pain and/or symptoms of chronic pain, wherein the medicament is prepared for peripheral administration or wherein the medicament is administered peripherally.

In a second aspect, the invention provides an anti-CGRP antagonist antibody for use in the prevention and/or treatment of chronic pain and/or symptoms of chronic pain wherein the antibody is prepared for peripheral administration or wherein the antibody is administered peripherally.

In third aspect, the invention provides the use of an anti-CGRP antagonist antibody for the manufacture of a medicament for ameliorating, controlling, reducing incidence of, or delaying the development or progression of chronic pain and/or symptoms of chronic pain, wherein the medicament is prepared for peripheral administration or wherein the medicament is administered peripherally.

In a fourth aspect, the invention provides a method of preventing and/or treating chronic pain and/or symptoms of chronic pain in an individual, comprising peripheral administration to the individual of an effective amount of an anti-CGRP antagonist antibody.

In a fifth aspect, the invention provides a method of ameliorating, controlling, reducing incidence of, or delaying the development or progression of chronic pain and/or symptoms of chronic pain in an individual, comprising peripheral administration to the individual of an effective amount of an anti-CGRP antagonist antibody.

According to a preferred embodiment of the present invention the individual is preferably a mammal, for example a companion animal such as a horse, cat or dog or a farm animal such as a sheep, cow or pig. Most preferably the mammal is a human.

According to a preferred embodiment of the present invention the medicament and/or anti-CGRP antagonist antibody is prepared for oral, sublingual, buccal, topical, rectal, inhalation, transdermal, subcutaneous, intravenous, intra-arterial, intramuscular, intracardiac, intraosseous, intradermal, intraperitoneal, transmucosal, vaginal, intravitreal, intra-articular, peri-articular, local or epicutaneous administration.

According to a further preferred embodiment the medicament is is prepared for peripheral administration prior to and/or during and/or after the development of chronic pain.

In one embodiment, the anti-CGRP antagonist antibody acts peripherally on administration. In one embodiment, the anti-CGRP antagonist antibody is not administered centrally, spinally or intrathecally.

According to a preferred embodiment of the present invention the chronic pain comprises one or more of chronic nociceptive pain, chronic neuropathic pain, chronic inflammatory pain, fibromyalgia, breakthrough pain and persistent pain. The chronic pain may comprise one or more of hyperalgesia, allodynia, central sensitisation, peripheral sensitisation, disinhibition and augmented facilitation.

According to a further preferred embodiment of the present invention the chronic pain is cancer pain, preferably cancer pain arising from malignancy or from cancer preferably selected from one or more of: adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumours, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, lymphoma, non-Hodgkin's, nervous system tumours, oral cancer, ovarian cancer, pancreatic cancer, prostate cancer, rectal cancer, skin cancer, stomach cancer, testicular cancer, thyroid cancer, urethral cancer, bone cancer, sarcomas cancer of the connective tissue, cancer of bone tissue, cancer of blood-forming cells, cancer of bone marrow, multiple myeloma, leukaemia, primary or secondary bone cancer, tumours that metastasize to the bone, tumours infiltrating the nerve and hollow viscus, tumours near neural structures. Further preferably the cancer pain comprises visceral pain, preferably visceral pain which arises from pancreatic cancer and/or metastases in the abdomen. Further preferably the cancer pain comprises somatic pain, preferably somatic pain due to one or more of bone cancer, metastasis in the bone, postsurgical pain, sarcomas cancer of the connective tissue, cancer of bone tissue, cancer of blood-forming cells of the bone marrow, multiple myeloma, leukaemia, primary or secondary bone cancer.

According to a preferred embodiment of the present invention the anti-CGRP antagonist antibody binds to CGRP, more preferably binds to CGRP and inhibits the ability of CGRP to bind to the CGRP receptor. Preferably the anti-CGRP antagonist antibody binds to both human and rodent CGRP, preferably human and rat CGRP. More preferably the antibody binds to human CGRP, further preferably the anti-CGRP antagonist antibody binds to human α-CGRP or to human α-CGRP and/or β-CGRP.

Most preferably the anti-CGRP antagonist antibody is an antibody that exhibits any one or more of the following functional characteristics: (a) binds to CGRP; (b) blocks CGRP from binding to its receptor(s); (c) blocks or decreases CGRP receptor activation, including cAMP activation; (d) inhibits, blocks, suppresses or reduces CGRP biological activity, including downstream pathways mediated by CGRP signalling, such as receptor binding and/or elicitation of a cellular response to CGRP; (e) prevents, ameliorates, or treats any aspect of chronic pain; (f) increases clearance of CGRP; and (g) inhibits (reduces) CGRP synthesis, production or release.

Antibodies of the invention, including G1 and G2, are known to bind CGRP and remove its biological availability for example in the serum thus preventing CGRP access to the its receptor and downstream cellular responses and biological effects of CGRP such as flare and vasodilation.

In a further preferred embodiment of the invention the anti-CGRP antagonist antibody binds to a fragment of CGRP, more preferably to a fragment of CGRP as well as to the full length CGRP. Preferably, the anti-CGRP antagonist antibody binds to the C-terminal region or fragment of CRGP. The C-terminal region or fragment of CRGP preferably comprises amino acids 19-37 or 25-37 or 29-37 or alternatively 30-37, further alternatively 31-37 of CGRP. In a further embodiment, the C-terminal region or fragment of CRGP preferably comprises amino acids 32-37 most preferably 33 to 37 of CGRP. Preferably the CGRP is either α-CGRP or β-CGRP, further preferably human or rodent, further preferably human or rat, more preferably human, further preferably human α-CGRP or β-CGRP, most preferably human α-CGRP.

In a further preferred embodiment of the invention the anti-CGRP antagonist antibody specifically binds to the amino acid sequence GSKAF (SEQ ID NO: 33). Preferably the sequence GSKAF (SEQ ID NO: 33) of CGRP is the epitope to which the anti-CGRP antagonist antibody binds, preferably at position 33 to 37, most preferably the sequence is GXXXF where X can be any amino acid, preferably at positions 33 to 37 of CGRP, the ends defined by amino acids G33 and F37 of CGRP.

In one embodiment, the present invention provides an anti-CGRP antagonist antibody which specifically binds to an epitope defined by amino acids G33 to F37 of CGRP. The anti-CGRP antagonist antibody may specifically bind to the epitope defined by the amino acid sequence GSKAF (SEQ ID NO: 33). In one embodiment, the present invention provides the use of such an antibody in the uses and methods defined in the various aspects of the present invention.

In one embodiment, the anti-CGRP antagonist antibody inhibits or prevents activation of the CGRP receptor. Preferably the anti-CGRP antibody has an IC50 of between 0.0001 (0.1 nM) to 500 µM. In some preferred embodiments, the IC50 is between 0.0001 µM and, or is at about, any of 250 µM, 100 µM, 50 µM, 10 µM, 1 µM, 500 nM, 250 nM, 100 nM, 50 nM, 20 nM, 15 nM, 10 nM, 5 nM, 1 nM, or 0.5 nM as measured in an in vitro binding assay. In some further preferred embodiments, IC50 is less than any of 500 pM, or 100 pM, or 50 pM, as measured in an in vitro binding assay. In a further more preferred embodiment IC50 is 1.2 nM or 31 nM.

In a further preferred embodiment, the anti-CGRP antagonist antibody used is capable of competing with an antibody herein above described for the binding of CGRP or to a fragment of CGRP, or to a fragment of CGRP as well as the full length CGRP, preferably to the C-terminal region or fragment of CRGP, preferably the C-terminal region or fragment of CRGP comprises amino acids 19-37 or 25-37 or 29-37 or alternatively 30-37, further alternatively 31-37 of CGRP. In a further embodiment, the C-terminal region or fragment of CRGP preferably comprises amino acids 32-37, most preferably 33 to 37 of CGRP.

In a further preferred embodiment, the anti-CGRP antagonist antibody or antigen binding portion thereof as used in the invention is capable of competing with an anti-CGRP antagonist antibody herein above described, in particular G1 or G2 as herein described, for:
(a) the binding of CGRP or a fragment of CGRP, or a fragment of CGRP as well as the full length CGRP, preferably the C-terminal region or fragment of CRGP, preferably the C-terminal region or fragment of CRGP comprising amino acids 19-37 or 25-37 or 29-37 or alternatively 30-37, further alternatively 31-37, preferably amino acids 32-37, most preferably 33 to 37 of CGRP, preferably the CGRP is alpha or beta, preferably beta, more preferably rodent or human, most preferably human.
(b) the binding of the epitope sequence GSKAF (SEQ ID NO: 33), preferably at amino acid position 33 to 37 of CGRP as defined in (a), more preferably to the sequence GXXXF, where X is any amino acid, preferably GXXXF at amino acid position 33 to 37 of CGRP as defined in (a).
(c) the binding as described in (a) or (b) with substantially the same Kd and/or substantially the same $K_{off}$.
(d) binding to CGRP and inhibiting/antagonising CGRP biological activity and/or downstream pathway(s), preferably the CGRP is alpha or beta, preferably beta, more preferably rodent or human, most preferably human.

The anti-CGRP antagonist antibody preferably binds to CGRP, region of CGRP or fragment of CGRP with a binding affinity ($K_d$) of between 0.00001 µM (0.01 nM) to 500 µM. In some preferred embodiments, the binding affinity (Kd) is between 0.00001 µM and, or is at about, any of 250 µM, 100 µM, 50 µM, 10 µM, 1 µM, 500 nM, 250 nM, 100 nM, 50 nM, 20 nM, 15 nM, 10 nM, 5 nM, 1 nM, 0.5 nM, 1 nM, 0.05 nM, or 0.01 nM as measured in an in vitro binding assay. In some further preferred embodiments, binding affinity (Kd) is less than any of 500 pM, or 100 pM, 50 pM, or 10 pM, as measured in an in vitro binding assay. In a further more preferred embodiment binding affinity (Kd) is 0.04 nM or 16 nM.

The anti-CGRP antagonist antibody as used in the present invention may be selected from the group of: monoclonal antibodies, polyclonal antibodies, antibody fragments (e.g., Fab, Fab', F(ab')2, Fv, Fc, ScFv etc.), chimeric antibodies, bispecific antibodies, heteroconjugate antibodies, single chain (ScFv) antibodies, mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The anti-CGRP antagonist antibody may be murine, rat, human, or any other origin (including chimeric or humanized antibodies). In some embodiments, the anti-CGRP antagonist antibody may be humanized but is more preferably human.

Preferably the anti-CGRP antagonist antibody is isolated, further preferably it is substantially pure. Where the anti-CGRP antagonist antibody is an antibody fragment the fragment preferably retains the functional characteristics of the original antibody i.e. the CGRP binding and/or antagonist activity as described in the functional characteristics above.

Examples of anti-CGRP antagonist antibodies are known in the art. Hence according to a preferred embodiment of the present invention the anti-CGRP antagonist antibody as used in the present invention is preferably an anti-CGRP antibody as generally or specifically disclosed in any of (i) WO2007/054809, (ii) WO2007/076336, (iii) Tan et al., Clin. Sci. (Lond). 89:565-73, 1995, (iv) Sigma (Missouri, US), product number C7113 (clone #4901), (v) Plourde et al., Peptides 14:1225-1229, 1993 or which comprises or consists of:
(a) a fragment of said antibody (e.g., Fab, Fab', F(ab')2, Fv, Fc, ScFv etc.),
(b) a light chain of said antibody,
(c) a heavy chain of said antibody,
(d) one or more variable region(s) from a light chain and/or a heavy chain of said antibody,
(e) one or more CDR(s) (one, two, three, four, five or six CDRs) of said antibody,
(f) CDR H3 from the heavy chain of said antibody,
(g) CDR L3 from the light chain of said antibody,
(h) three CDRs from the light chain of said antibody,
(i) three CDRs from the heavy chain of said antibody,
(j) three CDRs from the light chain and three CDRs from the heavy chain, of said antibody,
(k) any one or more of (a) through (j).

According to a preferred embodiment of the present invention the anti-CGRP antagonist antibody is antibody G2 or antibody G1. According to a most preferred embodiment of the present the anti-CGRP antagonist antibody used is the anti-CGRP antibody G1 as specifically disclosed in the patent application WO2007/054809, or comprising its variants shown in Table 6 of WO2007/054809, also including functionally equivalent antibodies to G1, i.e. comprising conservative substitutions of amino acid residues or one or more deletions or additions of amino acids which do not significantly affect their functional characteristics e.g. CRGP binding or antagonist activity and variants which have enhanced or decreased activity and/or binding. As used herein, the terms "G1" and "antibody G1" are used interchangeably to refer to an antibody produced by expression vectors having deposit numbers of ATCC PTA-6867 and ATCC PTA-6866 as disclosed in application WO2007/054809.

According to a further embodiment of the present invention, the anti-CGRP antagonist antibody comprises or consists of a polypeptide selected from: (a) antibody G1 or its variants shown in Table 6 of WO2007/054809; (b) a fragment or a region of antibody G1 or its variants shown in Table 6 of WO2007/054809; (c) a light chain of antibody G1 or its variants shown in Table 6 of WO2007/054809; (d) a heavy chain of antibody G1 or its variants shown in Table 6 of WO2007/054809 (e) one or more variable region(s) from a light chain and/or a heavy chain of antibody G1 or its variants shown in Table 6 of WO2007/054809; (f) one or more CDR(s) (one, two, three, four, five or six CDRs) of antibody G1 or its variants shown in Table 6 of WO2007/054809; (g) CDR H3 from the heavy chain of antibody G1 or its variants shown in Table 6 of WO2007/054809; (h) CDR L3 from the light chain of antibody G1 or its variants shown in Table 6 of WO2007/054809; (i) three CDRs from the light chain of antibody G1 or its variants shown in Table 6 of WO2007/054809; (j) three CDRs from the heavy chain of antibody G1 or its variants shown in Table 6 of WO2007/054809; (k) three CDRs from the light chain and/or three CDRs from the heavy chain, of antibody G1 or its variants shown in Table 6 of WO2007/054809; and (i) an antibody comprising any one of (b) through (k).

The invention also provides polypeptides comprising any one or more of the above. In some embodiments, the at least one, two, three, four, five, or six CDR(s) are at least about 85%, 86%, 87%, 88%, 89%, 90%, 95%, 96%, 97%, 98%, or 99% identical to at least one, two, three, four, five or six CDRs of G1 or its variants shown in Table 6 of WO2007/054809.

Determination of CDR regions is well within the ability of the skilled person. It is understood that in some embodiments, CDRs can be a combination of the Kabat and Chothia CDR. In some embodiments, the CDRs are the Kabat CDRs. In other embodiments, the CDRs are the Chothia CDRs.

The anti-CGRP antagonist antibody preferably comprises or consists of a fragment or a region of the antibody G1 (e.g., Fab, Fab', F(ab')2, Fv, Fc, ScFv etc.) or its variants shown in Table 6 of WO2007/054809. Preferably said fragment or region has the functional characteristics of an anti-CGRP antagonist antibody for example CGRP binding activity and/or antagonist activity and comprises or consists one or more of a light chain, heavy chain, fragment containing one or more variable regions from a light chain and/or a heavy chain, or one or more CDRs from a light chain and/or a heavy chain of the antibody G1.

According to a further preferred embodiment of the invention the anti-CGRP antagonist antibody comprises a light chain variable region, LCVR, comprising a peptide with a sequence selected from the group consisting of SEQ ID NOs: 28-32 and/or a heavy chain variable region, HCVR, comprising a peptide with a sequence selected from the group consisting of SEQ ID NOs: 34-38 of patent application WO2007/076336.

Further preferably the anti-CGRP antagonist antibody comprises an LCVR polypeptide of a SEQ ID NO as shown in Table 1 of patent application WO2007/076336 and further comprises a HCVR polypeptide of a SED ID NO as shown in Table 1 of patent application WO2007/076336.

According to a further embodiment of the invention the anti-CGRP antagonist antibody used comprises a light chain CDR (CDRL) selected from the group consisting of SEQ ID NOs: 8-13 and/or a heavy chain CDR (CDRH) selected from the group consisting of SEQ ID NOs: 14-22 of patent application WO2007/076336.

Methods of making and isolating the anti-CGRP antagonist antibodies of application WO2007/076336 and data demonstrating the CGRP binding and antagonist characterisation of the same are described in application WO2007/076336.

Preferably the anti-CGRP antagonist antibody for use in the present invention comprises a VH domain that is at least 85%, at least 86%, at least 87%, at least 88%, at least 89%, at least 90%, at least 91%, at least 92%, at least 93%, at least 94%, at least 95%, at least 96%, at least 97% at least 98%, at least 99% or 100% identical in amino acid sequence to SEQ ID NO: 1 or SEQ ID NO: 19 presented herein.

Preferably the anti-CGRP antagonist antibody comprises a VL domain that is at least 85%, at least 86%, at least 87%, at least 88%, at least 89%, at least 90%, at least 91%, at least 92%, at least 93%, at least 94%, at least 95%, at least 96%, at least 97% at least 98%, at least 99% or 100% identical in amino acid sequence to SEQ ID NO: 2 or SEQ ID NO: 20 presented herein.

The anti-CGRP antagonist antibody preferably comprises a VH domain and a VL domain that are at least 85%, at least 86%, at least 87%, at least 88%, at least 89%, at least 90%, at least 91%, at least 92%, at least 93%, at least 94%, at least 95%, at least 96%, at least 97% at least 98%, at least 99% or 100% identical in amino acid sequence to SEQ ID NO: 1 and 2 respectively or SEQ ID NO: 19 and 20 presented herein, respectively.

Preferably the anti-CGRP antagonist antibody comprises a VH domain that is at least 90% identical in amino acid sequence to SEQ ID NO: 1 and a VL domain that is at least 90% identical in amino acid sequence to SEQ ID NO: 2 presented herein.

Alternatively, the anti-CGRP antagonist antibody preferably comprises a VH domain that is at least 90% identical in amino acid sequence to SEQ ID NO: 19 and a VL domain that is at least 90% identical in amino acid sequence to SEQ ID NO: 20 presented herein.

The anti-CGRP antagonist antibody preferably comprises at least one CDR selected from the group consisting of: (a). CDR H1 as set forth in SEQ ID NO: 3 or 21; (b). CDR H2 as set forth in SEQ ID NO: 4 or 22; (c). CDR H3 as set forth in SEQ ID NO: 5 or 23; (d). CDR L1 as set forth in SEQ ID NO: 6 or 24; (e) CDR L2 as set forth in SEQ ID NO: 7 or 25; (f). CDR L3 as set forth in SEQ ID NO: 8 or 26; and (g). variants of CDR L1 CDR L2 and CDR H2 as shown in Table 6 of WO2007/054809.

According to a preferred embodiment of the present invention the anti-CGRP antagonist antibody heavy chain constant region may be from any types of constant region, such as IgG, IgM, IgD, IgA, and IgE; and any isotypes, such as IgGI, IgG2, IgG3, and IgG4.

Further preferably the anti-CGRP antagonist antibody comprises a heavy chain produced by the expression vector with ATCC Accession No. PTA-6867. Further preferably the anti-CGRP antagonist antibody comprises a light chain produced by the expression vector with ATCC Accession No. PTA-6866. Further preferably the anti-CGRP antagonist antibody is produced by the expression vectors with ATCC Accession Nos. PTA-6867 and PTA-6866.

Preferably the anti-CGRP antagonist antibody for use in the present invention is antibody G1 or antibody G2 defined herein.

According to a further embodiment of the invention, the anti-CGRP antagonist antibody comprises a modified constant region as for example described in WO2007/054809. Preferably the modified constant region is immunologically inert, including partially immunologically inert, such that it does not trigger complement mediated lysis, does not stimulate antibody-dependent cell mediated cytotoxicity (ADCC), does not activate microglia. Preferably the modified constant region is reduced in one or more of these activities. Most preferably the constant region is modified as described in Eur. J. Immunol. (1999) 29:2613-2624; PCT Application No. PCT/GB99/01441; and/or UK Patent Application No. 9809951.8. According to a preferred embodiment of the invention the anti-CGRP antagonist antibody comprises a human heavy chain IgG2 constant region comprising the following mutations: A330, P331 to S330, S331 (amino acid numbering with reference to the wildtype IgG2 sequence). Eur. J. Immunol. (1999) 29:2613-2624.

Methods of making and isolating the anti-CGRP antagonist antibodies of application WO2007/054809 and data demonstrating the CGRP binding and antagonist characterisation of the same are described in application WO2007/054809. Sequences of SEQ ID No. 1 to 14 of said application are provided herein as SEQ ID No. 1 to 14, respectively.

According to a further embodiment of the present invention the medicament is prepared for peripheral administration between once to 7 times per week, further preferably between once to four times per month, further preferably between once to six times per 6 month period, further preferably once to twelve times per year. Preferably the medicament is prepared to be peripherally administered in a period selected from: once daily, once every two, three, four, five or six days, weekly, once every two weeks, once every three weeks, monthly, once every two months, once every three months, once every four months, once every five months, once every six months, once every seven months, once every eight months, once every nine months, once every ten months, once every eleven months or yearly. According to preferred embodiments the medicament is prepared to be peripherally administered via a route selected from one or more of; orally, sublingually, buccally, topically, rectally, via inhalation, transdermally, subcutaneously, intravenously, intra-arterially or intramuscularly, via intracardiac administration, intraosseously, intradermally, intraperitoneally, transmucosally, vaginally, intravitreally, epicutaneously, intra-articularly, peri-articularly or locally.

According to a further embodiment of the present invention the medicament is prepared for peripheral administration with an antibody concentration of between 0.1 to 200 mg/ml; preferably at about, or between 0.1 and about, any one of 0.5, 1, 5, 10, 15 20, 25, 30, 35, 40, 45, 50, 55, 60, 65, 70, 75, 80, 85, 90, 95, 100, 110, 120, 130, 140, 150, 160, 170, 180, 190 or 200 mg/ml+/−10% error, most preferably at 50 mg/ml.

According to a further embodiment of the present invention the medicament is prepared for peripheral administration with an antibody concentration of between 0.1 to 200 mg/kg of body weight; preferably at about, or between 0.1 and about, any one of 0.5, 1, 5, 10, 15 20, 25, 30, 35, 40, 45, 50, 55, 60, 65, 70, 75, 80, 85, 90, 95, 100, 110, 120, 130, 140, 150, 160, 170, 180, 190 or 200 mg/kg of body weight+/−10% error, most preferably at 10 mg/kg.

According to a preferred embodiment of the present invention the anti-CGRP antagonist antibody has a half-life in-vivo of more than any one of 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208 or 210 days+/−1 day, further preferably more than any one of 7, 8, 9, 10, 11, or 12 months.

Preferably the anti-CGRP antagonist antibody has a half-life in-vivo of more than 6 days.

According to a further preferred embodiment of the present invention, the medicament and/or the anti-CGRP antagonist antibody does not produce effects of central nervous system and/or cognitive impairment. Preferably the medicament and/or the anti-CGRP antagonist antibody does not induce any one or more of the following: amnesia, confusion, depersonalization, hypesthesia, abnormal thinking, trismus, vertigo, akathisia, apathy, ataxia, circumoral paresthesia, CNS stimulation, emotional lability, euphoria, hallucinations, hostility, hyperesthesia, hyperkinesia, hypotonia, incoordination, libido increase, manic reaction, myoclonus, neuralgia, neuropathy, psychosis, seizure, abnormal speech, stupor, suicidal ideation; dizziness, somnolence, Insomnia, anxiety, tremor, depression or paresthesia. Most preferably the medicament and/or the anti-CGRP antagonist antibody does not induce impairment of motor coordination or attention.

According to a further embodiment of the present invention the medicament and/or the anti-CGRP antagonist antibody does not produce respiratory, renal or gastro-intestinal impairment.

According to a further embodiment of the present invention the medicament and/or the anti-CGRP antagonist antibody does not produce effects of physical and/or psychological dependence. Preferably the medicament and/or the anti-CGRP antagonist antibody does not demonstrate affinity for opiate, benzodiazepine, phencyclidine (PCP), or N-methyl-D-aspartic acid (NMDA) receptors, or CNS stimulant, or produce any sedating or euphoric effect.

In one embodiment, the anti-CGRP antagonist antibody, on administration, ameliorates, controls, reduces incidence of, or delays the development or progression of central pain sensation.

In another embodiment the effect of the anti-CGRP antagonist antibody is equal and/or superior to the effects of NSAIDS and/or opiates in the same models of chronic pain. In one embodiment, the anti-CGRP antagonist antibody is effective in treating refractory pain populations.

According to a further aspect of the present invention there is provided the use or method according to any other aspect of the invention wherein the anti-CGRP antagonist antibody is administered separately, sequentially or simultaneously in combination with one or more further pharmacologically active compounds or agents, preferably compounds or agents useful for treating chronic pain. Preferably the additional agent(s) is/are selected from one or more of:

(i) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

(ii) a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac, cyclooxygenase-2 (COX-2) inhibitors, celecoxib; rofecoxib; meloxicam; JTE-522; L-745,337; NS398; or a pharmaceutically acceptable salt thereof;

(iii) a barbiturate sedative, e.g. amobarbital, aprobarbital, butabarbital, butabital, mephobarbital, metharbital, methohexital, pentobarbital, phenobartital, secobarbital, talbutal, theamylal or thiopental or a pharmaceutically acceptable salt thereof;

(iv) a benzodiazepine having a sedative action, e.g. chlordiazepoxide, clorazepate, diazepam, flurazepam, lorazepam, oxazepam, temazepam or triazolam or a pharmaceutically acceptable salt thereof;
(v) an $H_1$ antagonist having a sedative action, e.g. diphenhydramine, pyrilamine, promethazine, chlorpheniramine or chlorcyclizine or a pharmaceutically acceptable salt thereof;
(vi) a sedative such as gluethimide, meprobamate, methaqualone or dichloralphenazone or a pharmaceutically acceptable salt thereof;
(vii) a skeletal muscle relaxant, e.g. baclofen, carisoprodol, chlorzoxazone, cyclobenzaprine, methocarbamol or orphrenadine or a pharmaceutically acceptable salt thereof;
(viii) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinone or cis-4-(phosphonomethyl)-2-piperidinecarboxylic acid or a pharmaceutically acceptable salt thereof;
(ix) an alpha-adrenergic, e.g. doxazosin, tamsulosin, clonidine or 4-amino-6,7-dimethoxy-2-(5-methanesulfonamido-1,2,3,4-tetrahydroisoquinol-2-yl)-5-(2-pyridyl) quinazoline;
(x) a tricyclic antidepressant, e.g. desipramine, imipramine, amytriptiline or nortriptiline; (xi) an anticonvulsant, e.g. carbamazepine or valproate;
(xii) a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-637), 5-[[(2R,3S)-2-[(1R)-1-[3,5-bis (trifluoromethyl)phenyl]ethoxy-3-(4-fluorophenyl)-4-morpholinyl]methyl]-1,2-dihydro-3H-1,2,4-triazol-3-one (MK-869), lanepitant, dapitant or 3-[[2-methoxy-5-(trifluoromethoxy)phenyl]methylamino]-2-phenyl-piperidine (2S, 3S);
(xiii) a muscarinic antagonist, e.g oxybutin, tolterodine, propiverine, tropsium chloride or darifenacin;
(xiv) a COX-2 inhibitor, e.g. celecoxib, rofecoxib or valdecoxib;
(xv) a non-selective COX inhibitor (preferably with GI protection), e.g. nitroflurbiprofen (HCT-1026);
(xvi) a coal-tar analgesic, in particular paracetamol;
(xvii) a neuroleptic such as droperidol;
(xviii) a vanilloid receptor agonist (e.g. resinferatoxin) or antagonist (e.g. capsazepine);
(xix) a beta-adrenergic such as propranolol;
(xx) a local anaesthetic, such as mexiletine;
(xxi) a corticosteriod, such as dexamethasone;
(xxii) a serotonin receptor agonist or antagonist;
(xxiii) a cholinergic (nicotinic) analgesic;
(xxiv) Tramadol (trade mark);
(xxv) a PDEV inhibitor, such as sildenafil, vardenafil or taladafil;
(xxvi) an alpha-2-delta ligand such as gabapentin or pregabalin;
(xxvii) a canabinoid; and
(xxviii) an antidepressant, such as amitriptyline (Elavil), trazodone (Desyrel), and imipramine (Tofranil) or anticonvulsants such as phenytoin (Dilantin) or carbamazepine (Tegretol).

According to a further aspect of the present invention there is provided a pharmaceutical composition for the prevention and/or treatment of chronic pain and/or symptoms of chronic pain or for ameliorating, controlling, reducing incidence of, or delaying the development or progression of chronic pain and/or symptoms of chronic pain in an individual, comprising an anti-CGRP antagonist antibody and a pharmaceutically acceptable carrier and/or an excipient, wherein the composition is prepared to be peripherally administered.

According to a further aspect of the present invention there is provided a kit comprising:
(a) a pharmaceutical composition as defined above; and
(b) instructions for the peripheral administration of an effective amount of said pharmaceutical composition to an individual for the prevention and/or treatment of chronic pain and/or symptoms of chronic pain or for ameliorating, controlling, reducing incidence of, or delaying the development or progression of chronic pain and/or symptoms of chronic pain.

The kit may include one or more containers containing an anti-CGRP antagonist antibody or polypeptide described herein and instructions for use in accordance with any of the methods and uses of the invention. The kit may further comprise a description of selecting an individual suitable for treatment based on identifying whether that individual has chronic pain or is at risk of having chronic pain. The instructions for the peripheral administration of the pharmaceutical composition may include information as to dosage, dosing schedule and routes of administration for the intended treatment.

Preferred features of each aspect of the invention apply equally to each other aspect mutatis mutandis.

EXAMPLES

The present invention is now described with reference to the following Examples which are intended to illustrate but not to limit the invention.

The following examples and figures are made with reference to antibody G1, an anti-human CGRP human monoclonal antibody; and to antibody G2, an anti-rat CGRP mouse monoclonal antibody (Wong H C et al. Hybridoma 12:93-106 (1993)).

Example 1: Set Up of the Rodent Cancer Mechanistic Pain Model

Tumour cells used are syngeneic MRMT-1 rat mammary gland carcinoma cells donated from the Novartis Institute (London). The cells are cultured in RPMI 1640 (Gibco) with 10% foetal bovine serum (FCS), 1% L-glutamine 2% penicillin/streptomycin (Gibco). Two brief washes are carried out with 0.1% w/v trypsin to release those cells which adhere to the flask, and then quenched with an equal volume of 10% FCS, followed by centrifugation of the solution for 3 minutes at 1200 rpm. The pellet is washed and resuspended in Hanks medium, and the concentration of cells calculated using a Haemocytometer, with trypan blue staining to determine the number of dead MRMT-1 cells. The final concentration of $3 \times 10^3$ cells was then obtained by diluting the solution according to the number of cells seen. The final solution was kept on ice until time of injection.

Male Sprague-Dawley rats weighing close to 170 g at time of surgery were used to generate the cancer model. Anaesthesia was induced in the rats using halothane or isoflurane (1.5-2%) 66% $N_2O$ and 33% $O_2$, the leg was shaved over the appropriate area and disinfected with chlorhexidine (Animalcare Ltd, UK.). A small incision in order to expose the anterior-medial surface of the distal end of the tibia was made. A hole was bored in the periosteum using a 0.7 mm dental drill, through which a 2 cm polythene tubing was fed 1 cm into the intra-medullar cavity of the tibia. Using a Hamilton syringe the pre-prepared 10 µl of $3 \times 10^3$ MRMT-1 cells were injected through the tubing into the cavity. The tubing was then removed and the hole plugged using bone restorative material (IRM, Dentsply USA). The wound was then irrigated with 0.9% saline and closed with a metal clip. The sham animals were operated upon using the same procedure but injected with 10 µl of Hank's solution alone. The animals were placed in a thermoregulated recovery box until such time that they were able to be placed back in their housing cages.

Example 2: Assessment of Rodent Anti-CGRP Antibody G2 in the Cancer Pain Model

Testing behaviour towards mechanical stimuli uses von Frey filaments (North Coast Medical Inc., USA) to the plantar surface of both the ipsilateral and contralateral hindpaw. The rats were placed in a Perspex cubicle with a mesh floor and allowed to acclimatise for 10 minutes. Each von Frey was applied 10 times to each hindpaw alternating between the ipsilateral and contralateral, for duration of 2-3 seconds each time. Von Frey Filaments used have bending forces of 1, 5, 9 and 15 g, and a period of 5 minutes was left between ascending von Frey forces. A nocifensive response (a lift) is defined as a brisk withdrawal of the hindpaw and the number of lifts for each paw at each von Frey are recorded (maximum of 10) and expressed as a percentage response. An assessment of the efficacy of rodent anti-CGRP antibody G2 in attenuating hypersensitivity to a wide variety of static mechanical, cooling and integrated stimuli was carried out as well as the background basal pain behaviours in this validated model of cancer induced bone pain. The responses measured are attenuated by standard analgesic treatments such as morphine and gabapentin. All measures were made by the same scientist in a blind fashion—blinded to the identity of the compound/control and to the treatment of the animal.

Figure 1:
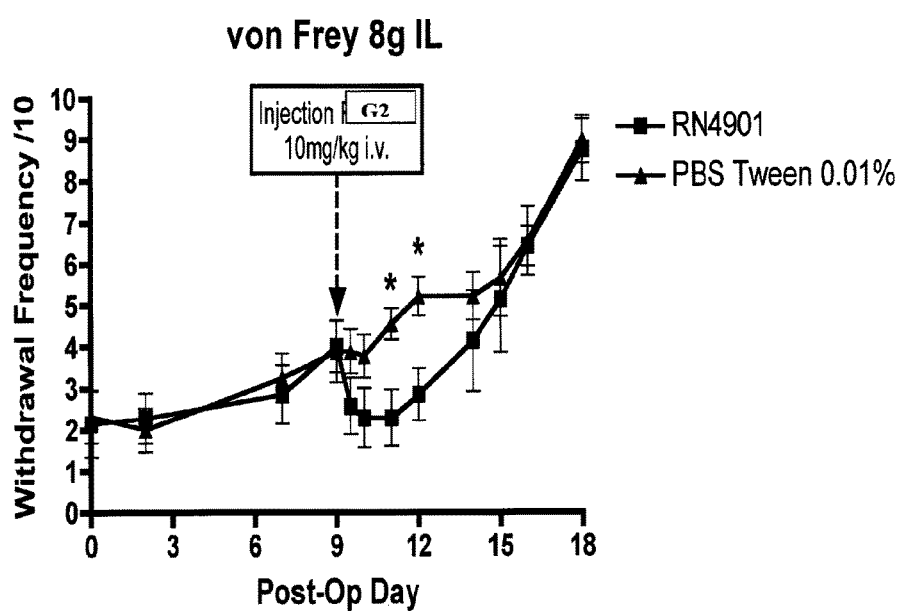
FIG. 1. Effect of antibody G2 on mechanical hypersensitivity to 8 gram von Frey stimuli in a bone cancer pain model. MRMT-1 injected rats were treated with antibody G2 or vehicle (PBS+0.01% Tween20) at day 9 post surgery. Groups were healthy throughout the post-operative period at all times, shown by increasing post-operative weight gain (data not shown). Data are mean±SEM of 7-9 rats per group. *p<0.05 versus vehicle treated group at each time point.

G2-was given IV at 10 mg/kg at day 9 and rats were tested at 2 hrs and then on days 10, 11, 12 and then 14-18 days post treatment (FIG. 1).

G2 had marked effect on the behavioural responses to the higher intensity mechanical stimuli. Withdrawal frequencies to von Frey 8 g were reduced two hours after injection and were significantly reduced over that seen in the vehicle treated group on days 11 and 12 (days 2 and 3 after injection, p=0.0164 and 0.0311, respectively). In fact, the G2 treated animals now had pain scores similar to the baseline values. By day 14 (day 5 post-G2 injection) there was no discernible difference between the G2 and vehicle-treated groups. Both groups reached a similar level of hypersensitivity to von Frey 8 g by day 18 after MRMT-1 injection (day 9 post-treatment).

Figure 2:
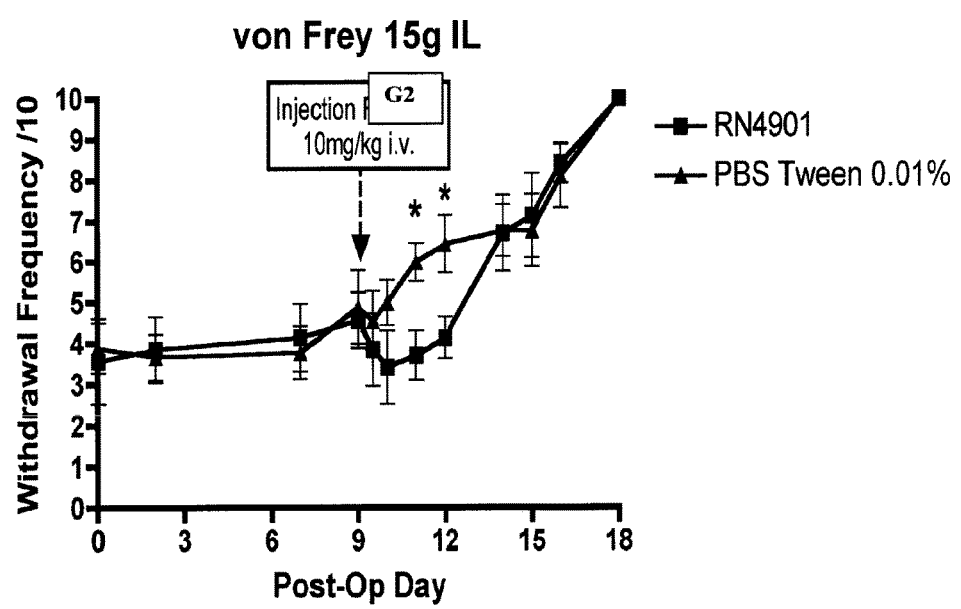
FIG. 2. Effect of antibody G2 on mechanical hypersensitivity to 15 gr von Frey stimuli in the bone cancer pain model. MRMT-1 injected rats were treated with G2 or vehicle (PBS+0.01% Tween20) at day 9 post surgery. Data are mean±SEM of 7-9 rats per group. *p<0.05 versus vehicle treated group at each time point.

A similar reversal in hypersensitivity to von Frey 15 g was also apparent. A reduction in hypersensitivity to von Frey 15 g from vehicle treated group was evident at 2 hours post-injection with significance seen at 2 and 3 days after drug administration (p=0.02 and 0.03 respectively). The reductions were lost by 6 days after G2 administration and both groups now reached similar maximal withdrawal frequencies by 18 days post MRMT-1 injection (FIG. 2).

The results indicate that G2 reduces noxious pain experienced in the metastatic bone cancer rat model.

Example 3: Rota Rod Test for Motor Impairment

A further end point tested in the bone cancer pain model was ambulation (by rotarod). The test is to obtain a measurement of locomotor impairment comparing antibody treated with control animals, each subjected to the same test under the same conditions. The rota rod test consists of 4 rotateable drums divided by flanges with a motor-driven drum accelerated (Ugo Basile, Comerio, VA, Italy). For a given trial, a rat is placed on the rotating rod and the rotation speed is accelerated from 4 to 16 rpm in 2 min. The time of maximal performance is typically set at 120 sec. Each animal generally receives three trials per day, at 1 hr intervals, for several consecutive days post-surgery. The latency to fall off the rod is represented as mean of the three trials.

Figure 3:
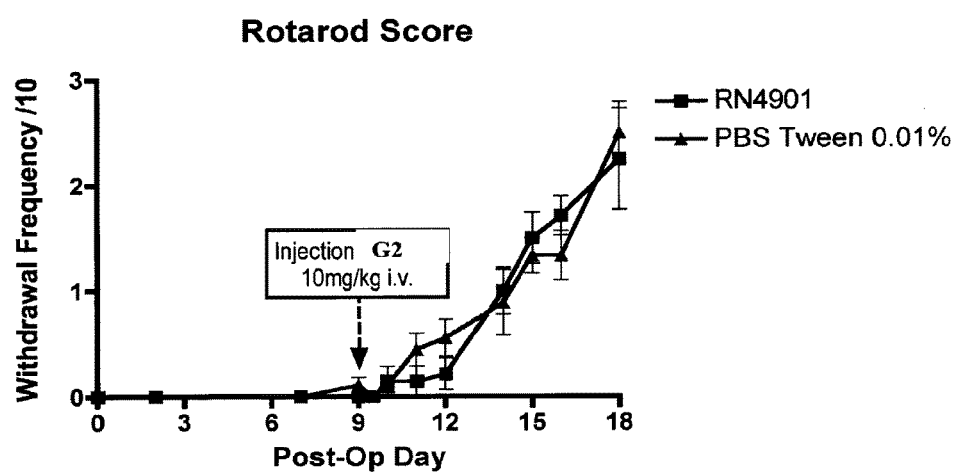
FIG. 3. Effect of antibody G2 on ambulation measured by rota rod. Two end points were explored. The latency to fall as measurements of compound induced impairments in motor co-ordination (A), and rota rod score, as measurements of ambulation evoked pain (B) in the bone cancer pain model. MRMT-1 injected rats were treated with antibody G2 or vehicle (PBS+0.01% Tween20) at day 9 post surgery. Data are mean±SEM of 7-9 rats per group. *p<0.05 versus vehicle treated group at each time point.

No differences were found between the antibody G2 group and the vehicle group in the latency to fall from the rotarod during forced ambulation (FIG. 3). This suggests that G2 does not impair pathways involved in motor co-ordination, or attention and points to a lack of CNS side-effects produced by the antibody.

Example 4: Binding Assay

A binding assay was performed to measure the $IC_{50}$ of anti-CGRP antibody G1 and G2 in blocking human α-CGRP from binding to the CGRP1-receptor in SK-N-MC cells. Dose response curves were plotted and $K_i$ values were determined using the equation: $K_i=IC_{50}/(1+([ligand]/K_D)$; FIG. 4, where the equilibrium dissociation constant $K_D=8$ pM for human α-CGRP to CGRP1-receptor as present in SK-N-MC cells. The reported $IC_{50}$ value (in terms of IgG molecules) was converted to binding sites so that it could be compared with the affinities ($K_D$) determined by Biacore, using N-biotinylated human and rat α-CGRPs were captured on individual flow cells at low levels (typically 100 response units) to provide the reaction surfaces, while an unmodified flow cell served as a reference channel. G1 was titrated over the chip surface Binding affinities were deduced from the quotient of the kinetic rate constants ($K_D=k_{off}/k_{on}$) see Table 1.

TABLE 1

|  | G2 | Mouse Mab 7E9 | G1 |
| --- | --- | --- | --- |
| KD (nM), α-Hu | 17 | 1.0 | 0.04 |
| IC50 (nM) α-Hu | 37 | 2.6 | 1.2 |
| KD (nM) α-Rat | 1.0 | 58 | 1.2 |

| N-biotin-CGRP on chip | °C. | $k_{on}$ (1/Ms) | $K_{off}$ (1/s) | $T_{1/2}$ (h) | $K_D$ (nM) |
| --- | --- | --- | --- | --- | --- |
| α-human | 25 | $1.86 \times 10^5$ | $7.80 \times 10^{-5}$ | 24.68 | 0.042 |
| α-human | 37 | $5.87 \times 10^5$ | $3.63 \times 10^{-5}$ | 5.30 | 0.063 |
| β-human | 37 | $4.51 \times 10^5$ | $6.98 \times 10^{-5}$ | 2.76 | 0.155 |
| α-rat | 25 | $5.08 \times 10^4$ | $6.18 \times 10^{-5}$ | 3.12 | 1.22 |
| α-rat | 37 | $1.55 \times 10^5$ | $3.99 \times 10^{-4}$ | 0.48 | 2.57 |
| β-rat | 37 | $5.16 \times 10^5$ | $7.85 \times 10^{-5}$ | 2.45 | 0.152 |

Binding affinity of G1 for human α and β CGRP was equivalent (Kd=0.155 and 0.152 nM respectively). Binding affinity of G2 for rat α and β CGRP was equivalent (16 and 17 nM, respectively). Additionally G1 binding affinity is 40-fold more potent in human than rat for α-CGRP (Kd=0.042 and 1.22 nM, respectively) and equi-potent in human and rat for β-CGRP (Kd=0.155 and 0.152 nM, respectively). Antibody G1 also demonstrated good cross species selectivity and binds rat α-CGRP with the same affinity as antibody G2 (around 1.2 nM) Table 2.

G1 binds human and cynomolgus monkey α- and β-CGRP with high affinity ($K_D$=63 and 155 pM, respectively). G1 displays species selectivity for human/cyno CGRP and binds α- and β-CGRP from other species e.g. rat with lower affinity ($K_D$=2.57 nM and 152 pM, respectively).

Example 5: Half-Life of Anti-CGRP In-Vivo

Serum measurements of anti-CGRP in rat, FIG. 5, indicate that the half life is of the order of 7 days. The antibody is peripherally restricted having a molecular weight of around 150,000, FIGS. 5a, 5b, i.e. it does not cross into the central nervous system or cross the blood brain barrier.

Example 6: Selectivity of Anti-CGRP Antibody

We determined the specificity of antibody G1 to human or rat CGRP by using the Biacore chip to "probe" the free concentration of a premixed complex of mAb+peptide. As expected when we pre-incubated antibody G1 with human or rat CGRP the response was fully blocked. In contrast pre-incubating G1, with an excess of amylin, calcitonin or adrenomedullin was comparable to the control response (G1 plus buffer) demonstrating that G1 did not form a complex with these peptides (FIG. 7).

Example 7: Identification of Antibody G1 Binding Epitope

Interaction analysis was conducted at 25° C. on a Biacore 3000™ system equipped with streptavidin-coated (SA) sensor chips (Biacore AB, Uppsala, Sweden) using a standard Biacore running buffer (HBS-P). First we confirmed that an N-biotinylated 25-37 human α-CGRP fragment bound with the same affinity to antibody G1, as full-length N-biotinylated human α-CGRP. Each amino acid between position 27-37 was then mutated individually to alanine and expressed the fold loss in affinity compared to the wild-type fragment. N-biotinylated fragments were captured on individual flow cells at low levels (typically 100 response units) to provide the reaction surfaces, while an unmodified flow cell served as a reference channel. Purified Fab fragments of antibody G1 were generated. Fab fragments were titrated over the chip using 1 µM as the top concentration of a two-fold dilution series. Association and dissociation phases were monitored at 100 µl/min for 1 minute and 5 minutes respectively. Surfaces were regenerated with a mixture of 35% ethanol+25 mM NaOH+0.5M NaCl.

The alanine scan results show that antibody G1 binds to the C-terminal region of human α-CGRP, particularly residues 25 to 37, and shows specific binding to a region (i.e. loss of affinity is markedly increased when the specific binding region is mutated) which can be defined as the epitope and which lies within the last 5 C-terminal amino acids, i.e. from G33A to F37A. Most profound changes in affinity are caused through the G33A and F37A mutation (FIG. 6). C-terminal Phe is important for selectivity of antibody G1 for CGRP vs related peptides and gene family members (FIG. 8).

Thus, in one embodiment, the present invention provides an anti-CGRP antagonist antibody which specifically binds to an epitope defined by amino acids G33 to F37 of CGRP. The anti-CGRP antagonist antibody may specifically bind to the epitope defined by the amino acid sequence GSKAF (SEQ ID NO: 33), more specifically to the epitope of CGRP is defined as GXXXF where X can be any amino acid, the G33 and F37 being the most important residues of the epitope for defining high affinity binding of the anti-CGRP antagonist antibody.

Example 8: Analysis of Indicators of Physical or Psychological Dependence

Neither antibody G1 nor antibody G2 demonstrate CNS penetration. Additionally long term observation of animals (rats) dosed with either antibody to levels used in the previous examples did not reveal adverse CNS events such as sedation or stimulation/euphoric behaviour in comparison to control animals. These observations indicate an absence of dependency risk for the antibodies and hence a significantly improved safety of the antibodies over current opiates used in current pain therapies.

Example 9: Analysis of Indicators of Gastro-Intestinal Adverse Effects

A 1 month in-vivo rat study with antibody G2 and 1 week comparative study with antibody G1 demonstrated that no adverse gastro intestinal effects were observed on behaviour, food intake, stool production or histopathology in comparison to control animals. These observations indicate an absence of gastrointestinal risk for the antibodies and hence a significantly improved safety of the antibodies over current NSAIDs used in current pain therapies.

Example 10; G1 and G2 as Anti-CGRP Antagonist Antibodies

A known consequence of CGRP biological activity is the generation neurogenic flare when delivered in vivo. G1 and G2 are demonstrated to be anti-CGRP antagonist antibodies in that they prevent the development of neurogenic flare in vivo.

Using a neurogenic skin flare rat model the efficacy of G1 was tested for its ability to block CGRP effect in vivo. The saphenous nerve in the rat is electrically stimulated causing CGRP release from nerve endings and leading to vasodilation, the resulting changes in blood flow can be measured using laser Dopler methods.

Changes in blood flow parameters were expressed as the area under the curve (AUC, change in arbitrary Doppler flux units multiplied by time). CGRP receptor antagonist $CGRP_{8-37}$ (400 nmol/kg, i.v.) was used as a positive control to validate the specificity of the model (data not shown). To determine the effect of G1 prior to dosing for each animal, the baseline blood flow response to stimulation was established with two saphenous nerve stimulations each 30 minutes apart. Rats were treated with G1 after the blood flow response of the second stimulation had returned to baseline levels (approximately 10 minutes post stimulation) and an additional four stimulations at 30 minute intervals were performed.

Results (FIG. 9) demonstrated that in vehicle treated animals no significant change in blood flow response was but rats treated with G1 showed a significant decrease in blood flow response starting at 90 and 120 minutes post dose for 10 mg/kg and 1 mg/kg, respectively. Similar activity was achieved using D2. Additionally in further neurogenic flare and vasodilatation model tests G1 showed marked effect at 7 days post IV dosing (predicted $ED_{50}$=6 ug/ml in saphenous nerve stimulation model). The conclusions form the tests done is that G1 and G2 demonstrate anti-CGRP antagonist activity. Similar CGRP function-blocking ability for the antibodies is also shown in the publication, Zeller J, et. al. Br J Pharmacol. 2008 December; 155(7):1093-103. Epub 2008 Sep. 8.

The following materials have been deposited with the American Type Culture Collection, 10801 University Boulevard, Manassas. Va. 20100-2209, USA (ATCC):

| Material | Antibody No. | ATCC Accession No. | Date of Deposit |
| --- | --- | --- | --- |
| pDb.CGRP.hFcGI | G1 heavy chain | PTA-6867 | Jul. 15, 2005 |
| pEb.CGRP.hKGI | G1 light chain | PTA-6866 | Jul. 15, 2005 |

Vector pEb.CGRP.hKGI is a polynucleotide encoding the G1 light chain variable region and the light chain kappa constant region; and vector pDb.CGRP.hFcGI is a polynucleotide encoding the G1 heavy chain variable region and the heavy chain IgG2 constant region containing the following mutations: A330P331 to S330S331 (amino acid numbering with reference to the wildtype IgG2 sequence, see Eur. J. Immunol., 1999,29:2613-2624).

Below are given antibody sequences useful for practising the present invention.
Antibody Sequences
Antibody G1 Heavy Chain Variable Region Amino Acid Sequence (SEQ ID NO:1)

EVQLVESGGGLVQPGGSLRLSCAASGFTFSNYWISWVRQAPGKGLEWVAE

IRSESDASATHYAEAVKGRFTISRDNAKNSLYLQMNSLRAEDTAVYYCLA

YFDYGLAIQNYWGQGTLVTVSS

Antibody G1 Light Chain Variable Region Amino Acid Sequence (SEQ ID NO:2)

EIVLTQSPATLSLSPGERATLSCKASKRVTTYVSWYQQKPGQAPRLLIYG

ASNRYLGIPARFSGSGSGTDFTLTISSLEPEDFAVYYCSQSYNYPYTFGQ

GTKLEIK

Antibody G1 CDR H1 (Extended CDR) (SEQ ID NO:3)
  GFTFSNYWIS
Antibody G1 CDR H2 (extended CDR) (SEQ ID NO:4)
  EIRSESDASATHYAEAVKG
Antibody G1 CDR H3 (SEQ ID NO:5)
  YFDYGLAIQNY
Antibody G1 CDR L1 (SEQ ID NO:6)
  KASKRVTTYVS
Antibody G1 CDR L2 (SEQ ID NO:7)
  GASNRYL
Antibody G1 CDR L3 (SEQ ID NO:8)
  SQSYNYPYT
Antibody G1 Heavy Chain Variable Region Nucleotide Sequence (SEQ ID NO:9)

GAAGTTCAGCTGGTTGAATCCGGTGGTGGTCTGGTTCAGCCAGGTGGTTC

CCTGCGTCTGTCCTGCGCTGCTTCCGGTTTCACCTTCTCCAACTACTGGA

TCTCCTGGGTTCGTCAGGCTCCTGGTAAAGGTCTGGAATGGGTTGCTGAA

ATCCGTTCCGAATCCGACGCGTCCGCTACCCATTACGCTGAAGCTGTTAA

AGGTCGTTTCACCATCTCCCGTGACAACGCTAAGAACTCCCTGTACCTGC

AGATGAACTCCCTGCGTGCTGAAGACACCGCTGTTTACTACTGCCTGGCT

TACTTTGACTACGGTCTGGCTATCCAGAACTACTGGGGTCAGGGTACCCT

GGTTACCGTTTCCTCC

Antibody G1 Light Chain Variable Region Nucleotide Sequence (SEQ ID NO:10)

GAAATCGTTCTGACCCAGTCCCCGGCTACCCTGTCCCTGTCCCCAGGTGA

ACGTGCTACCCTGTCCTGCAAAGCTTCCAAACGGGTTACCACCTACGTTT

CCTGGTACCAGCAGAAACCCGGTCAGGCTCCTCGTCTGCTGATCTACGGT

GCTTCCAACCGTTACCTCGGTATCCCAGCTCGTTTCTCCGGTTCCGGTTC

CGGTACCGACTTCACCCTGACCATCTCCTCCCTGGAACCCGAAGACTTCG

CTGTTTACTACTGCAGTCAGTCCTACAACTACCCCTACACCTTCGGTCAG

GGTACCAAACTGGAAATCAAA

Antibody G1 Heavy Chain Full Antibody Amino Acid Sequence (Including Modified IgG2 as Described Herein) (SEQ ID NO:11)

EVQLVESGGGLVQPGGSLRLSCAASGFTFSNYWISWVRQAPGKGLEWVAE

IRSESDASATHYAEAVKGRFTISRDNAKNSLYLQMNSLRAEDTAVYYCLA

YFDYGLAIQNYWGQGTLVTVSSASTKGPSVFPLAPCSRSTSESTAALGCL

VKDYFPEPVTVSWNSGALTSGVHTFPAVLQSSGLYSLSSVVTVPSSNFGT

QTYTCNVDHKPSNTKVDKTVERKCCVECPPCPAPPVAGPSVFLFPPKPKD

TLMISRTPEVTCVVVDVSHEDPEVQFNWYVDGVEVHNAKTKPREEQFNST

FRVVSVLTVVHQDWLNGKEYKCKVSNKGLPSSIEKTISKTKGQPREPQVY

TLPPSREEMTKNQVSLTCLVKGFYPSDIAVEWESNGQPENNYKTTPPMLD

SDGSFFLYSKLTVDKSRWQQGNVFSCSVMHEALHNHYTQKSLSLSPGK

Antibody G1 Light Chain Full Antibody Amino Acid Sequence (SEQ ID NO:12)

EIVLTQSPATLSLSPGERATLSCKASKRVTTYVSWYQQKPGQAPRLLIYG

ASNRYLGIPARFSGSGSGTDFTLTISSLEPEDFAVYYCSQSYNYPYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Antibody G1 Heavy Chain Full Antibody Nucleotide Sequence (Including Modified IgG2 as Described Herein) (SEQ ID NO:13)

GAAGTTCAGCTGGTTGAATCCGGTGGTGGTCTGGTTCAGCCAGGTGGTTC

CCTGCGTCTGTCCTGCGCTGCTTCCGGTTTCACCTTCTCCAACTACTGGA

TCTCCTGGGTTCGTCAGGCTCCTGGTAAAGGTCTGGAATGGGTTGCTGAA

ATCCGTTCCGAATCCGACGCGTCCGCTACCCATTACGCTGAAGCTGTTAA

AGGTCGTTTCACCATCTCCCGTGACAACGCTAAGAACTCCCTGTACCTGC

AGATGAACTCCCTGCGTGCTGAAGACACCGCTGTTTACTACTGCCTGGCT

```
TACTTTGACTACGGTCTGGCTATCCAGAACTACTGGGGTCAGGGTACCCT

GGTTACCGTTTCCTCCGCCTCCACCAAGGGCCCATCTGTCTTCCCACTGG

CCCCATGCTCCCGCAGCACCTCCGAGAGCACAGCCGCCCTGGGCTGCCTG

GTCAAGGACTACTTCCCAGAACCTGTGACCGTGTCCTGGAACTCTGGCGC

TCTGACCAGCGGCGTGCACACCTTCCCAGCTGTCCTGCAGTCCTCAGGTC

TCTACTCCCTCAGCAGCGTGGTGACCGTGCCATCCAGCAACTTCGGCACC

CAGACCTACACCTGCAACGTAGATCACAAGCCAAGCAACACCAAGGTCGA

CAAGACCGTGGAGAGAAAGTGTTGTGTGGAGTGTCCACCTTGTCCAGCCC

CTCCAGTGGCCGGACCATCCGTGTTCCTGTTCCCTCCAAAGCCAAAGGAC

ACCCTGATGATCTCCAGAACCCCAGAGGTGACCTGTGTGGTGGTGGACGT

GTCCCACGAGGACCCAGAGGTGCAGTTCAACTGGTATGTGGACGGAGTGG

AGGTGCACAACGCCAAGACCAAGCCAAGAGAGGAGCAGTTCAACTCCACC

TTCAGAGTGGTGAGCGTGCTGACCGTGGTGCACCAGGACTGGCTGAACGG

AAAGGAGTATAAGTGTAAGGTGTCCAACAAGGGACTGCCATCCAGCATCG

AGAAGACCATCTCCAAGACCAAGGGACAGCCAAGAGAGCCACAGGTGTAT

ACCCTGCCCCCATCCAGAGAGGAGATGACCAAGAACCAGGTGTCCCTGAC

CTGTCTGGTGAAGGGATTCTATCCATCCGACATCGCCGTGGAGTGGGAGT

CCAACGGACAGCCAGAGAACAACTATAAGACCACCCCTCCAATGCTGGAC

TCCGACGGATCCTTCTTCCTGTATTCCAAGCTGACCGTGGACAAGTCCAG

ATGGCAGCAGGGAAACGTGTTCTCTTGTTCCGTGATGCACGAGGCCCTGC

ACAACCACTATACCCAGAAGAGCCTGTCCCTGTCTCCAGGAAAGTAA
```

Antibody G1 Light Chain Full Antibody Nucleotide Sequence (SEQ ID NO:14)

```
GAAATCGTTCTGACCCAGTCCCCGGCTACCCTGTCCCTGTCCCCAGGTGA

ACGTGCTACCCTGTCCTGCAAAGCTTCCAAACGGGTTACCACCTACGTTT

CCTGGTACCAGCAGAAACCCGGTCAGGCTCCTCGTCTGCTGATCTACGGT

GCTTCCAACCGTTACCTCGGTATCCCAGCTCGTTTCTCCGGTTCCGGTTC

CGGTACCGACTTCACCCTGACCATCTCCTCCCTGGAACCCGAAGACTTCG

CTGTTTACTACTGCAGTCAGTCCTACAACTACCCCTACACCTTCGGTCAG

GGTACCAAACTGGAAATCAAACGCACTGTGGCTGCACCATCTGTCTTCAT

CTTCCCTCCATCTGATGAGCAGTTGAAATCCGGAACTGCCTCTGTTGTGT

GCCTGCTGAATAACTTCTATCCGCGCGAGGCCAAAGTACAGTGGAAGGTG

GATAACGCCCTCCAATCCGGTAACTCCCAGGAGAGTGTCACAGAGCAGGA

CAGCAAGGACAGCACCTACAGCCTCAGCAGCACCCTGACCCTGAGCAAAG

CAGACTACGAGAAACACAAAGTCTACGCCTGCGAAGTCACCCATCAGGGC

CTGAGTTCTCCAGTCACAAAGAGCTTCAACCGCGGTGAGTGCTAA
```

Amino acid sequence comparison of human and rat CGRP (human α-CGRP (SEQ ID NO:15); human β-CGRP (SEQ ID NO:16); rat α-CGRP (SEQ ID NO:17); and rat β-CGRP (SEQ ID NO:18)):

NH₂-ACDTATCVTHRLAGLLSRSGGVVKNNFVPT-NVGSKAF-CONH₂ (SEQ ID NO:15)
NH₂-ACNTATCVTHRLAGLLSRSGGMVKSNFVPT-NVGSKAF-CONH₂ (SEQ ID NO:16)
NH₂-SCNTATCVTHRLAGLLSRSGGVVKDNFVPT-NVGSEAF-CONH₂ (SEQ ID NO:17)
NH₂-SCNTATCVTHRLAGLLSRSGGVVKDNFVPT-NVGSKAF-CONH₂ (SEQ ID NO:18)

Antibody G2 Heavy Chain Variable Region Amino Acid Sequence (SEQ ID NO:19)

```
EVQLQQSGPELVKPGASVKMSCKASGYTFTSSVMHWVKQKPGQGLEWIGY

INPYNDGTKYNEKFKGKATLTSDKSSTAYMELSSLTSEDSAVYYCAKGG

NDGYWGQGTTLTVSS
```

Antibody G2 Light Chain Variable Region Amino Acid Sequence (SEQ ID NO:20)

```
EIVLTQSPTTMAASPGEKITITCSASSSISSIYLHWYQQKPGFSPKVLIY

RASNLASGVPARFSGSGSGTSYSLTIGTMEAEDVATYYCQQGSTIPFTFG

SGTKLEIK
```

Antibody G2 CDR H1 (Extended CDR) (SEQ ID NO:21)
 SSVMH
Antibody G2 CDR H2 (Extended CDR) (SEQ ID NO:22)
 YINPYNDGTKYNEKFKG
Antibody G2 CDR H3 (SEQ ID NO:23)
 GGNDGY
Antibody G2 CDR L1 (SEQ ID NO:24)
 SASSSISSIYLH
Antibody G2 CDR L2 (SEQ ID NO:25)
 RASNLAS
Antibody G2 CDR L3 (SEQ ID NO:26)
 QQGSTIPFT Antibody G2 Heavy Chain Variable Region Nucleotide Sequence (SEQ ID NO:27)

```
GAGGTCCAGCTGCAGCAGTCTGGACCTGAGCTGGTAAAGCCTGGGGCTTC

AGTGAAGATGTCCTGCAAGGCTTCTGGATACACATTCACTAGCTCTGTTA

TGCACTGGGTGAAGCAGAAGCCTGGGCAGGGCCTTGAGTGGATTGGATAT

ATTAATCCTTACAATGATGGTACTAAGTACAATGAGAAGTTCAAAGGCAA

GGCCACACTGACTTCAGACAAATCCTCCAGCACAGCCTACATGGAACTCA

GCAGCCTGACCTCTGAGGACTCTGCGGTCTATTACTGTGCAAAAGGGGGT

AACGATGGCTACTGGGGCCAAGGCACTACTCTCACAGTCTCCTCA
```

Antibody G2 Light Chain Variable Region Nucleotide Sequence (SEQ ID NO:28)

```
GAAATTGTGCTCACCCAGTCTCCAACCACCATGGCTGCATCTCCCGGGGA

GAAGATCACTATCACCTGTAGTGCCAGCTCAAGTATAAGTTCCATTTACT

TGCATTGGTATCAGCAGAAGCCAGGATTCTCCCCTAAAGTCTTGATTTAT

AGGGCATCCAATCTGGCTTCTGGAGTCCCAGCTCGCTTCAGTGGCAGTGG

GTCTGGGACCTCTTACTCTCTCACAATTGGCACCATGGAGGCTGAAGATG

TTGCCACTTACTACTGCCAGCAGGGTAGTACTATACCATTCACGTTCGGC

TCGGGGACAAAGTTGGAAATAAAA
```

Antibody G2 Heavy Chain Full Antibody Amino Acid Sequence (not Including Fc Domain) (SEQ ID NO:29)

EVQLQQSGPELVKPGASVKMSCKASGYTFTSSVMHWVKQKPGQGLEWIGY

INPYNDGTKYNEFKGKATLTSDKSSSTAYMELSSLTSEDSAVYYCAKGG

NDGYWGQGTTLTVSSAKTTPPSVYPLAPGSAAQTNSMVTLGCLVKGYFPE

PVTVTWNSGSLSSGVHTFPAVLQSDLYTLSSSVTVPSSTWPSETVTCNVA

HPASSTKVDKKIVPRD

Antibody G2 Light Chain Full Antibody Amino Acid Sequence (SEQ ID NO:30)

EIVLTQSPTTMAASPGEKITITCSASSSISSIYLHWYQQKPGFSPKVLIY

RASNLASGVPARFSGSGSGTSYSLTIGTMEAEDVATYYCQQGSTIPFTFG

SGTKLEIKRADAAPTVSIFPPSSEQLTSGGASVVCFLNNFYPRDINVKWK

IDGSERQNGVLNSWTDQDSKDSTYSMSSTLTLTKDEYERHNSYTCEATHK

TSTSPIVKSFNRNEC

Antibody G2 Heavy Chain Full Antibody Nucleotide Sequence (not Including Fc Domain) (SEQ ID NO:31)

GAGGTCCAGCTGCAGCAGTCTGGACCTGAGCTGGTAAAGCCTGGGGCTTC

AGTGAAGATGTCCTGCAAGGCTTCTGGATACACATTCACTAGCTCTGTTA

TGCACTGGGTGAAGCAGAAGCCTGGGCAGGGCCTTGAGTGGATTGGATAT

ATTAATCCTTACAATGATGGTACTAAGTACAATGAGAAGTTCAAAGGCAA

GGCCACACTGACTTCAGACAAATCCTCCAGCACAGCCTACATGGAACTCA

GCAGCCTGACCTCTGAGGACTCTGCGGTCTATTACTGTGCAAAGGGGGT

AACGATGGCTACTGGGGCCAAGGCACTACTCTCACAGTCTCCTCAGCCAA

AACGACACCCCCATCTGTCTATCCACTGGCCCCTGGATCTGCTGCCCAAA

CTAACTCCATGGTGACCCTGGGATGCCTGGTCAAGGGCTATTTCCCTGAG

CCAGTGACAGTGACCTGGAACTCTGGATCCCTGTCCAGCGGTGTGCACAC

CTTCCCAGCTGTCCTGCAGTCTGACCTCTACACTCTGAGCAGCTCAGTGA

CTGTCCCCTCCAGCACCTGGCCCAGCGAGACCGTCACCTGCAACGTTGCC

CACCCGGCCAGCAGCACCAAGGTGGACAAGAAAATTGTGCCCAGGGAT

Antibody G2 Light Chain Full Antibody Nucleotide Sequence (SEQ ID NO:32)

GAAATTGTGCTCACCCAGTCTCCAACCACCATGGCTGCATCTCCCGGGGA

GAAGATCACTATCACCTGTAGTGCCAGCTCAAGTATAAGTTCCATTTACT

TGCATTGGTATCAGCAGAAGCCAGGATTCTCCCCTAAAGTCTTGATTTAT

AGGGCATCCAATCTGGCTTCTGGAGTCCCAGCTCGCTTCAGTGGCAGTGG

GTCTGGGACCTCTTACTCTCTCACAATTGGCACCATGGAGGCTGAAGATG

TTGCCACTTACTACTGCCAGCAGGGTAGTACTATACCATTCACGTTCGGC

TCGGGGACAAAGTTGGAAATAAAACGGGCTGATGCTGCACCAACTGTATC

CATCTTCCCACCATCCAGTGAGCAGTTAACATCTGGAGGTGCCTCAGTCG

TGTGCTTCTTGAACAACTTCTACCCCAGAGACATCAATGTCAAGTGGAAG

ATTGATGGCAGTGAACGACAAAATGGTGTCCTGAACAGTTGGACTGATCA

GGACAGCAAAGACAGCACCTACAGCATGAGCAGCACCCTCACATTGACCA

AGGACGAGTATGAACGACATAACAGCTATACCTGTGAGGCCACTCACAAG

ACATCAACTTCACCCATCGTCAAGAGCTTCAACAGGAATGAGTGTTAA

---

The invention claimed is:

1. A method of treatment of fibromyalgia and/or symptoms of fibromyalgia in an individual, the method comprising administering to the individual a therapeutically effective amount of an anti-CGRP antagonist antibody, wherein the anti-CGRP antagonist antibody comprises the following complementarity determining regions (CDRs):
   (a) CDR H1 as set forth in SEQ ID NO: 3;
   (b) CDR H2 as set forth in SEQ ID NO: 4;
   (c) CDR H3 as set forth in SEQ ID NO: 5;
   (d) CDR L1 as set forth in SEQ ID NO: 6;
   (e) CDR L2 as set forth in SEQ ID NO: 7; and
   (f) CDR L3 as set forth in SEQ ID NO: 8.

2. The method according to claim 1, wherein the anti-CGRP antagonist antibody is administered peripherally.

3. The method according to claim 1, wherein the anti-CGRP antagonist antibody is administered subcutaneously or intravenously.

4. The method according to claim 1, wherein the anti-CGRP antagonist antibody acts peripherally on administration.

5. The method according to claim 1, wherein the anti-CGRP antagonist antibody:
   (i) is a human antibody,
   (ii) is a humanized antibody,
   (iii) is a monoclonal antibody,
   (iv) binds CGRP with a Kd of 50 nM or less (as measured by surface plasmon resonance at 37° C.); and/or
   (v) has a half-life in-vivo of at least 7 days.

6. The method according to claim 1, wherein the anti-CGRP antibody comprises a VH domain that is at least 90% identical in amino acid sequence to SEQ ID NO: 1.

7. The method according to claim 1, wherein the anti-CGRP antibody comprises a VL domain that is at least 90% identical in amino acid sequence to SEQ ID NO: 2.

8. The method according to claim 1, wherein the anti-CGRP antibody comprises a VH domain that is at least 90% identical in amino acid sequence to SEQ ID NO: 1 and a VL domain that is at least 90% identical in amino acid sequence to SEQ ID NO: 2.

9. The method according to claim 1, wherein the anti-CGRP antibody comprises a heavy chain produced by the expression vector with ATCC Accession No. PTA-6867.

10. The method according to claim 1, wherein the anti-CGRP antibody comprises a light chain produced by the expression vector with ATCC Accession No. PTA-6866.

11. The method according to claim 1, wherein the anti-CGRP antibody is produced by the expression vectors with ATCC Accession Nos. PTA-6867 and PTA-6866.

12. The method according to claim 1, wherein the anti-CGRP antagonist antibody is administered by subcutaneous or intravenous injection one time per month.

13. The method according to claim 1, wherein the anti-CGRP antagonist antibody does not produce CNS impairment of motor coordination or attention.

14. The method according to claim 1, wherein the anti-CGRP antagonist antibody is not administered centrally, spinally or intrathecally.

15. The method according to claim 1, wherein the anti-CGRP antagonist antibody is not a centrally, spinally or intrathecal penetrating molecule.

16. The method according to claim 1, wherein the anti-CGRP antibody is administered separately, sequentially or simultaneously in combination with one or more further pharmacologically active compounds.

17. The method according to claim 16, wherein the one or more further pharmacologically active compounds is/are selected from;
   (i) an opioid analgesic;
   (ii) a nonsteroidal antiinflammatory drug;
   (iii) a barbiturate sedative;
   (iv) a benzodiazepine having a sedative action;
   (v) an $H_1$ antagonist having a sedative action;
   (vi) a sedative;
   (vii) a skeletal muscle relaxant;
   (viii) an NMDA receptor antagonist;
   (ix) an alpha-adrenergic;
   (x) a tricyclic antidepressant;
   (xi) an anticonvulsant;
   (xii) a tachykinin antagonist;
   (xiii) a muscarinic antagonist;
   (xiv) a COX-2 inhibitor;
   (xv) a non-selective COX inhibitor;
   (xvi) a coal-tar analgesic;
   (xvii) a neuroleptic;
   (xviii) a vanilloid receptor agonist;
   (xix) a beta-adrenergic;
   (xx) a local anaesthetic;
   (xxi) a corticosteroid;
   (xxii) a serotonin receptor agonist or antagonist;
   (xxiii) a cholinergic analgesic;
   (xxiv) Tramadol;
   (xxv) a PDEV inhibitor;
   (xxvi) an alpha-2-delta ligand; and
   (xxvii) a canabinoid.

18. The method of claim 17, wherein the corticosteroid is dexamethasone.

* * * * *